US011039961B2

(12) United States Patent
Long et al.

(10) Patent No.: US 11,039,961 B2
(45) Date of Patent: Jun. 22, 2021

(54) METHOD AND APPARATUS FOR ADVANCING AND FOLDING AN ABSORBENT ARTICLE

(71) Applicant: The Procter & Gamble Company, Cincinnati, OH (US)

(72) Inventors: Michael Devin Long, Springfield Township, OH (US); Todd M. Fegelman, Wyoming, OH (US); Matthew Alexander Gittings, Cincinnati, OH (US); Tanner Laurie Williams, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 633 days.

(21) Appl. No.: 15/461,557

(22) Filed: Mar. 17, 2017

(65) Prior Publication Data

US 2017/0266059 A1 Sep. 21, 2017

Related U.S. Application Data

(60) Provisional application No. 62/310,007, filed on Mar. 18, 2016.

(51) Int. Cl.
*A61F 13/15* (2006.01)
*A61F 13/496* (2006.01)

(52) U.S. Cl.
CPC .. *A61F 13/15747* (2013.01); *A61F 13/15804* (2013.01); *A61F 13/496* (2013.01)

(58) Field of Classification Search
CPC .......... A61F 13/15747; A61F 13/15804; A61F 13/496
See application file for complete search history.

(56) References Cited

U.S. PATENT DOCUMENTS

| 881,640 A | 3/1908 | Wimmel |
| 2,075,189 A | 10/1935 | Galligan et al. |

(Continued)

FOREIGN PATENT DOCUMENTS

| EP | 1 581 159 A1 | 7/2004 |
| EP | 2 275 064 | 1/2011 |

(Continued)

OTHER PUBLICATIONS

PCT International Search Report, dated Jun. 8, 2017, 12 pages.
PCT International Search Report, dated Jul. 11, 2017, 14 pages.
All Office Actions; U.S. Appl. No. 15/461,553.

*Primary Examiner* — Thanh K Truong
*Assistant Examiner* — Katie L Gerth
(74) *Attorney, Agent, or Firm* — Jay A. Krebs

(57) ABSTRACT

A method and apparatus to transfer and fold a partially folded absorbent article. The transfer apparatus includes a frame that is rotatable about a first axis of rotation and a transfer member that is rotatable about a second axis of rotation. The transfer member includes a receiving surface. While advancing absorbent article, the transfer member rotates the absorbent article about the second axis of rotation. The partially folded absorbent article is transferred to a folding apparatus. The folding apparatus advances the partially folded absorbent article such that the end regions of the belt of the partially folded absorbent article are directed away from the folding apparatus. The end regions are engaged by a folding assembly. The folding assembly guides and/or pushes the end regions toward the central region of the belt and/or the chassis to form a folded absorbent article.

6 Claims, 30 Drawing Sheets

(56) References Cited

U.S. PATENT DOCUMENTS

| | | |
|---|---|---|
| 3,025,199 A | 3/1962 | Harwood |
| 3,368,562 A | 2/1968 | Vogt |
| 3,794,033 A | 2/1974 | Ryan |
| 3,848,594 A | 11/1974 | Buell |
| 3,860,003 A | 1/1975 | Buell |
| 3,911,173 A | 10/1975 | Sprague, Jr. |
| 3,939,837 A | 2/1976 | Taylor |
| 3,963,029 A | 6/1976 | Brooks |
| 4,107,364 A | 8/1978 | Sisson |
| 4,209,563 A | 6/1980 | Sisson |
| 4,216,773 A | 8/1980 | Ryan |
| 4,515,595 A | 5/1985 | Kievit et al. |
| 4,573,986 A | 3/1986 | Minetola et al. |
| 4,610,678 A | 9/1986 | Weisman et al. |
| 4,662,875 A | 5/1987 | Hirotsu et al. |
| 4,673,402 A | 6/1987 | Weisman et al. |
| 4,681,581 A | 7/1987 | Coates |
| 4,695,278 A | 9/1987 | Lawson |
| 4,699,622 A | 10/1987 | Toussant et al. |
| 4,704,115 A | 11/1987 | Buell |
| 4,785,996 A | 11/1988 | Ziecker et al. |
| 4,795,454 A | 1/1989 | Dragoo |
| 4,802,884 A | 2/1989 | Fröidh et al. |
| 4,834,735 A | 5/1989 | Alemany et al. |
| 4,834,741 A | 5/1989 | Sabee |
| 4,842,666 A | 6/1989 | Werenicz |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,946,527 A | 8/1990 | Battrell |
| 4,963,140 A | 10/1990 | Robertson et al. |
| 5,151,092 A | 9/1992 | Buell et al. |
| 5,181,915 A | 1/1993 | Smith |
| 5,221,274 A | 6/1993 | Buell et al. |
| 5,242,436 A | 9/1993 | Weil et al. |
| 5,330,458 A | 7/1994 | Buell et al. |
| 5,499,978 A | 3/1996 | Buell et al. |
| 5,507,736 A | 4/1996 | Clear et al. |
| 5,562,646 A | 10/1996 | Goldman et al. |
| 5,591,152 A | 1/1997 | Buell et al. |
| 5,599,335 A | 2/1997 | Goldman et al. |
| 5,628,097 A | 5/1997 | Benson et al. |
| 5,669,894 A | 9/1997 | Goldman et al. |
| 5,916,661 A | 6/1999 | Benson et al. |
| 5,919,334 A | 7/1999 | Niedermeyer |
| 6,050,984 A | 4/2000 | Fujioka et al. |
| 6,065,521 A | 5/2000 | Tharpe, Jr. et al. |
| 6,107,539 A | 8/2000 | Palumbo et al. |
| 6,165,160 A | 12/2000 | Suzuki et al. |
| 6,432,098 B1 | 8/2002 | Kline et al. |
| 6,458,065 B1 | 10/2002 | Niedermeyer |
| 6,461,471 B1 | 10/2002 | Tharpe, Jr. et al. |
| 6,497,032 B2 | 12/2002 | Maxton et al. |
| 6,513,221 B2 | 2/2003 | Vogt et al. |
| 6,514,187 B2 | 2/2003 | Coenen et al. |
| 6,523,035 B1 | 2/2003 | Fleming et al. |
| 6,545,197 B1 | 4/2003 | Muller et al. |
| 6,551,431 B2 | 4/2003 | Lee |
| 6,562,167 B2 | 5/2003 | Coenen et al. |
| 6,596,107 B2 | 7/2003 | Stopher |
| 6,596,113 B2 | 7/2003 | Csida et al. |
| 6,626,881 B2 | 9/2003 | Shingu et al. |
| 6,635,135 B2 | 10/2003 | Kuen et al. |
| 6,699,166 B2 * | 3/2004 | Walter ............ A61F 13/15634 493/446 |
| 6,702,798 B2 | 3/2004 | Christoffel et al. |
| 6,743,321 B2 | 6/2004 | Guralski et al. |
| 6,748,996 B2 | 6/2004 | Nakakado et al. |
| 6,776,316 B2 | 8/2004 | Van Eperen et al. |
| 6,790,798 B1 | 9/2004 | Suzuki et al. |
| 6,821,370 B2 | 11/2004 | Tomsovic et al. |
| 6,854,624 B2 | 2/2005 | Vogt et al. |
| 6,884,209 B2 | 4/2005 | Roozrokh |
| 6,979,380 B2 | 12/2005 | Thorson et al. |
| 7,144,357 B2 | 12/2006 | Yamamoto et al. |
| 7,156,939 B2 | 1/2007 | Vogt et al. |
| 7,163,528 B2 | 1/2007 | Christon et al. |
| 7,175,584 B2 | 2/2007 | Maxton et al. |
| 7,220,335 B2 | 5/2007 | Van Gompel et al. |
| 7,285,178 B2 | 10/2007 | Mischler et al. |
| 7,318,798 B2 | 1/2008 | Yamamoto et al. |
| 7,322,925 B2 | 1/2008 | Couillard et al. |
| 7,384,386 B2 | 6/2008 | Sosalla |
| 7,387,148 B2 | 6/2008 | Vogt et al. |
| 7,390,373 B2 | 6/2008 | Karlsson et al. |
| 7,419,562 B2 | 9/2008 | Van Gompel et al. |
| 7,431,791 B2 | 10/2008 | Heller et al. |
| 7,500,941 B2 | 3/2009 | Coe |
| 7,507,224 B2 | 3/2009 | Datta et al. |
| 7,569,039 B2 | 8/2009 | Matsuda et al. |
| 7,658,813 B2 | 2/2010 | Petersen |
| 7,682,349 B2 | 3/2010 | Popp et al. |
| 7,740,732 B2 | 6/2010 | Umebayashi et al. |
| 7,780,156 B2 | 8/2010 | Schmitz |
| 8,007,622 B2 | 8/2011 | Heller et al. |
| 8,039,685 B2 | 10/2011 | Mason et al. |
| 8,069,988 B2 | 12/2011 | Snell |
| 8,105,304 B2 | 1/2012 | Uda |
| 8,207,395 B2 | 6/2012 | Soerens et al. |
| 8,273,003 B2 | 9/2012 | Umebayashi et al. |
| 8,317,022 B2 | 11/2012 | Hagner et al. |
| 8,323,167 B2 | 12/2012 | Berggren et al. |
| 8,342,333 B2 | 1/2013 | Snell |
| 8,361,048 B2 | 1/2013 | Kuen et al. |
| 8,382,928 B2 | 2/2013 | Umebayashi |
| 8,409,066 B2 | 4/2013 | Allen et al. |
| 8,439,814 B2 | 5/2013 | Piantoni et al. |
| 8,440,039 B2 | 5/2013 | Nakakado |
| 8,454,782 B2 | 6/2013 | Ostertag |
| 8,459,457 B2 | 6/2013 | Hagner et al. |
| 8,585,666 B2 | 11/2013 | Weisman et al. |
| 8,585,671 B2 | 11/2013 | Faulks et al. |
| 8,607,959 B2 | 12/2013 | Papsdorf et al. |
| 8,617,341 B2 | 12/2013 | Schneider |
| 8,657,729 B2 | 2/2014 | Yamamoto |
| 8,672,824 B2 | 3/2014 | Soblone et al. |
| 8,696,343 B2 | 4/2014 | Yamamoto |
| 8,720,666 B2 | 5/2014 | Papsdorf et al. |
| 8,764,721 B2 | 7/2014 | Van Gompel et al. |
| 8,815,037 B2 | 8/2014 | Bäck et al. |
| 8,820,513 B2 | 9/2014 | Papsdorf et al. |
| 8,821,360 B2 | 9/2014 | Umebayashi |
| 8,833,542 B2 | 9/2014 | Papsdorf et al. |
| 8,864,733 B2 | 10/2014 | Koenig et al. |
| 8,939,957 B2 | 1/2015 | Raycheck et al. |
| 8,945,078 B2 | 2/2015 | Takino |
| 8,955,670 B2 | 2/2015 | Murakami et al. |
| 9,066,833 B2 | 6/2015 | Gassner et al. |
| 9,072,632 B2 | 7/2015 | LaVon et al. |
| 9,108,819 B2 | 8/2015 | Murakami et al. |
| 9,150,321 B2 | 10/2015 | Schneider et al. |
| 9,168,183 B2 | 10/2015 | Yamamoto |
| 9,289,329 B1 | 3/2016 | Schaap |
| 9,314,380 B2 | 4/2016 | Yamamoto et al. |
| 2002/0148557 A1 | 10/2002 | Heller et al. |
| 2003/0225390 A1* | 12/2003 | Vogt ................. A61F 13/15747 604/391 |
| 2004/0097895 A1 | 5/2004 | Busam et al. |
| 2004/0158212 A1 | 8/2004 | Ponomarenko et al. |
| 2004/0193135 A1 | 9/2004 | Van Gompel |
| 2005/0107764 A1 | 5/2005 | Matsuda et al. |
| 2005/0256494 A1 | 11/2005 | Datta |
| 2006/0157188 A1 | 7/2006 | Thorson et al. |
| 2006/0218700 A1 | 10/2006 | Uda |
| 2006/0241561 A1 | 10/2006 | De Angelis |
| 2007/0043331 A1 | 2/2007 | Haruki et al. |
| 2007/0107918 A1* | 5/2007 | Coe .................. A61F 13/15747 172/695 |
| 2008/0141839 A1 | 6/2008 | Van Gompel et al. |
| 2009/0299321 A1 | 12/2009 | Uda |
| 2009/0312730 A1 | 12/2009 | LaVon et al. |
| 2011/0030886 A1 | 2/2011 | Van Gompel et al. |
| 2011/0100526 A1 | 5/2011 | Umebayashi |

(56) References Cited

U.S. PATENT DOCUMENTS

| | | |
|---|---|---|
| 2011/0132976 A1 | 6/2011 | Drewnowski et al. |
| 2011/0139336 A1 | 6/2011 | Sakaguchi |
| 2011/0155304 A1 | 6/2011 | Sakaguchi et al. |
| 2011/0167765 A1 | 7/2011 | Yamamoto |
| 2011/0247747 A1 | 10/2011 | Schneider et al. |
| 2011/0251038 A1 | 10/2011 | LaVon et al. |
| 2011/0282315 A1 | 11/2011 | Gustin Bergström et al. |
| 2012/0061015 A1 | 3/2012 | LaVon et al. |
| 2012/0061016 A1 | 3/2012 | LaVon et al. |
| 2012/0078210 A1 | 3/2012 | Corlett |
| 2012/0108410 A1 | 5/2012 | Perego et al. |
| 2012/0152436 A1 | 6/2012 | Schneider |
| 2012/0157282 A1 | 6/2012 | Schneider |
| 2012/0157287 A1* | 6/2012 | Yamamoto ........ A61F 13/15747 493/423 |
| 2012/0172828 A1 | 7/2012 | Koenig et al. |
| 2012/0202664 A1* | 8/2012 | Brown .............. A61F 13/15772 493/8 |
| 2012/0225764 A1 | 9/2012 | Ogasawara |
| 2012/0277702 A1 | 11/2012 | Raycheck et al. |
| 2012/0316047 A1 | 12/2012 | Sablone et al. |
| 2012/0330262 A1 | 12/2012 | Lawson et al. |
| 2012/0330263 A1 | 12/2012 | Lawson et al. |
| 2012/0330264 A1 | 12/2012 | Lawson et al. |
| 2013/0000555 A1 | 1/2013 | Pavol et al. |
| 2013/0030400 A1 | 1/2013 | Hashino et al. |
| 2013/0060222 A1 | 3/2013 | Gerstle et al. |
| 2013/0123730 A1 | 5/2013 | Corlett |
| 2013/0130879 A1 | 5/2013 | Schoon et al. |
| 2013/0130880 A1 | 5/2013 | Sieck et al. |
| 2013/0211363 A1 | 8/2013 | LaVon et al. |
| 2013/0218117 A1 | 8/2013 | Snell |
| 2013/0244853 A1 | 9/2013 | Rosani et al. |
| 2013/0255861 A1 | 10/2013 | Schneider et al. |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2013/0270066 A1 | 10/2013 | Schneider |
| 2014/0031780 A1 | 1/2014 | Vogt et al. |
| 2014/0039442 A1 | 2/2014 | Popp et al. |
| 2014/0112751 A1 | 4/2014 | Schneider |
| 2014/0113793 A1 | 4/2014 | Schneider et al. |
| 2014/0128830 A1 | 5/2014 | Veith et al. |
| 2014/0221185 A1 | 8/2014 | Yamamoto |
| 2014/0318695 A1* | 10/2014 | LaVon .............. A61F 13/15699 156/227 |
| 2015/0158672 A1 | 6/2015 | Lenser et al. |
| 2015/0158673 A1 | 6/2015 | Lenser |
| 2015/0202092 A1 | 7/2015 | McCabe et al. |
| 2015/0209190 A1 | 7/2015 | Sablone et al. |
| 2016/0242968 A1 | 8/2016 | Wada |
| 2017/0266058 A1 | 9/2017 | Long |

FOREIGN PATENT DOCUMENTS

| | | |
|---|---|---|
| EP | 2 403 458 B1 | 10/2013 |
| EP | 2 926 785 A1 | 12/2013 |
| WO | WO 2003/003959 A1 | 1/2003 |
| WO | WO 2011/091843 A1 | 8/2011 |
| WO | WO 2012/008261 A1 | 1/2012 |
| WO | WO 2012/095739 A1 | 7/2012 |
| WO | WO 2014/075872 A1 | 5/2014 |
| WO | WO 2014/178305 A1 | 11/2014 |

* cited by examiner

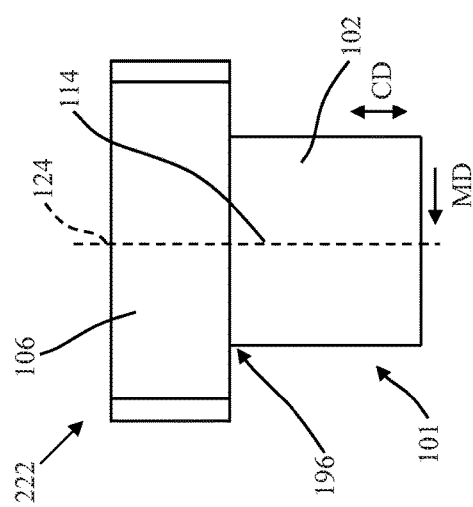
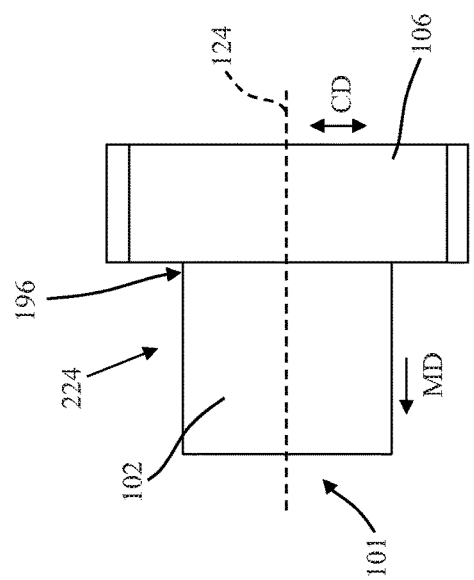

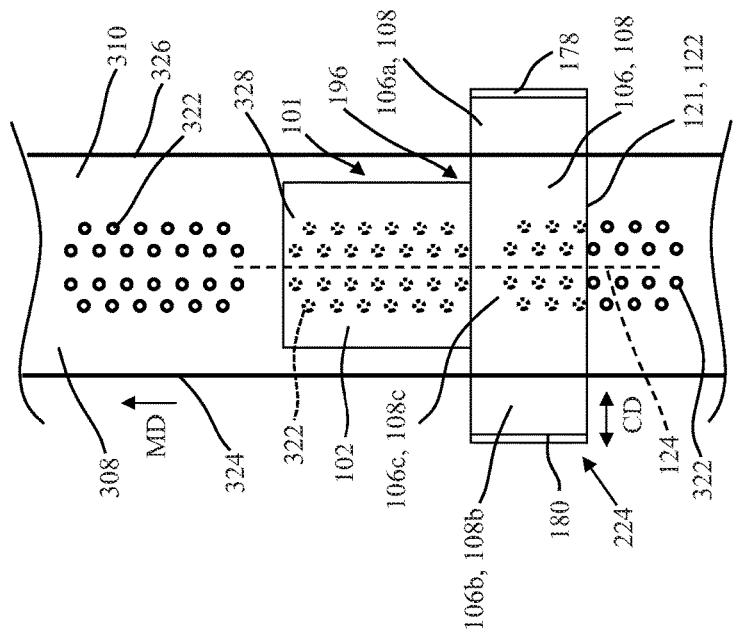
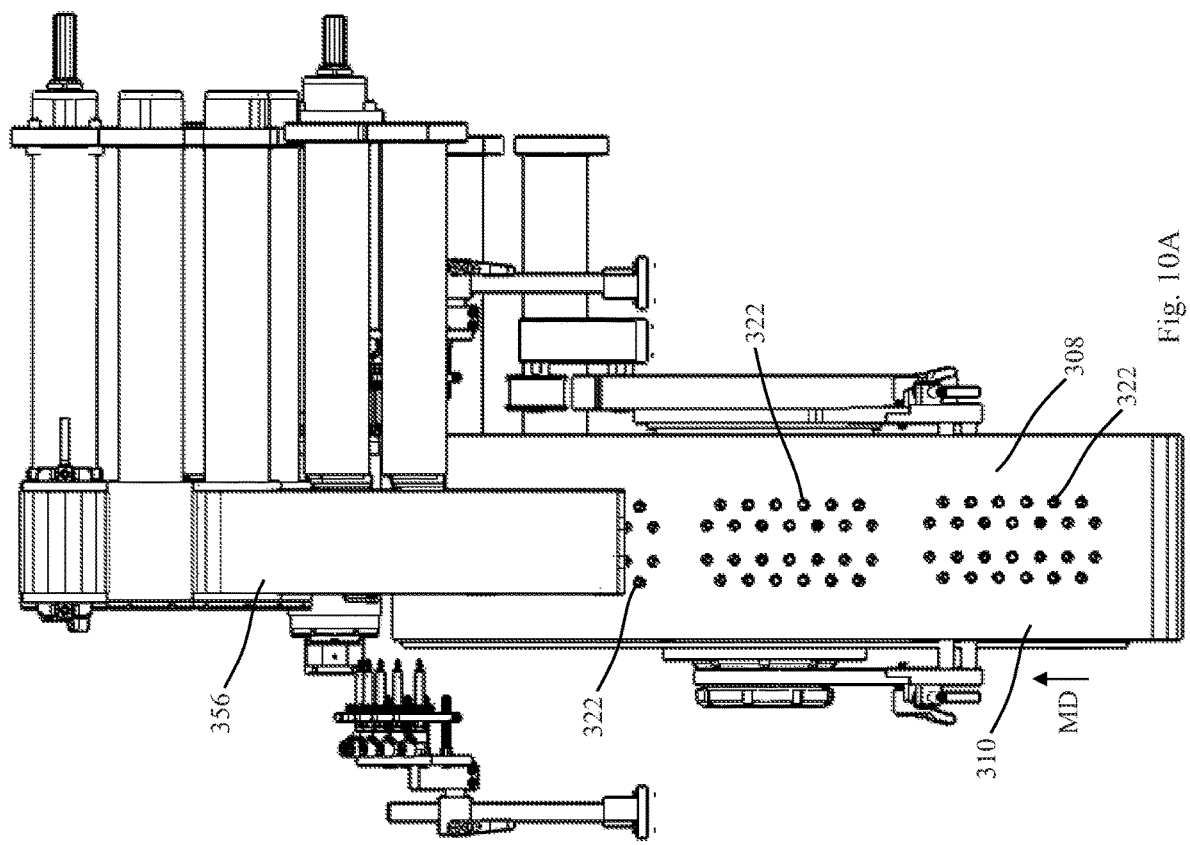
Fig. 10B
Fig. 10A

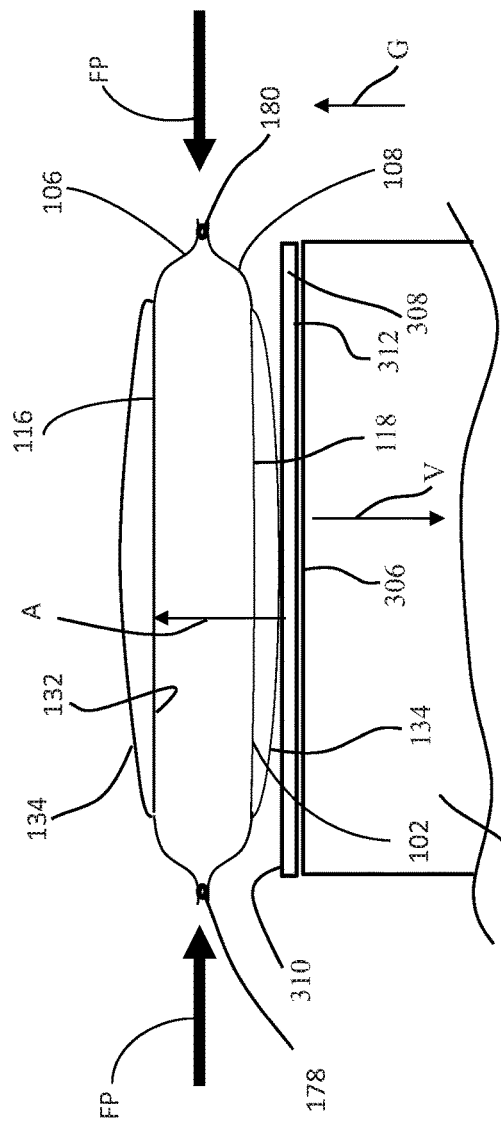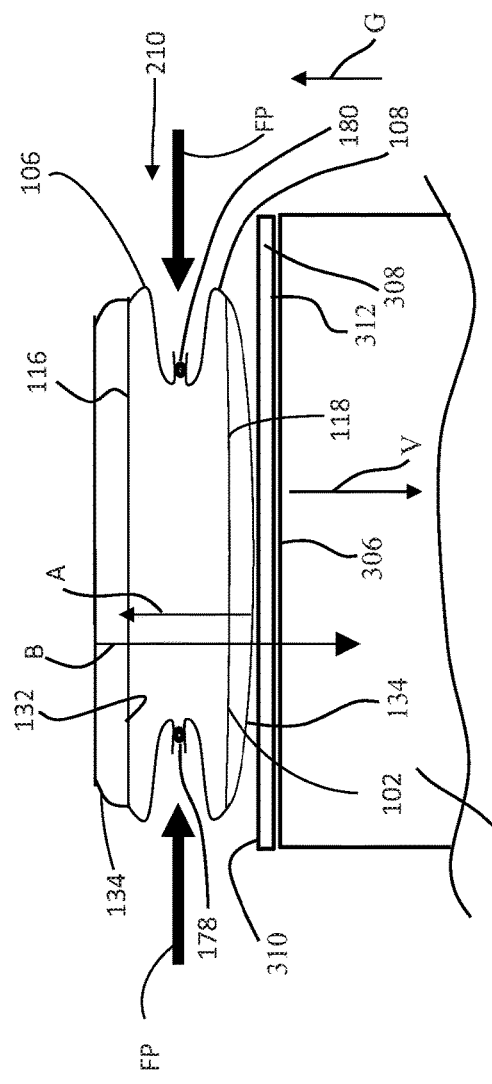

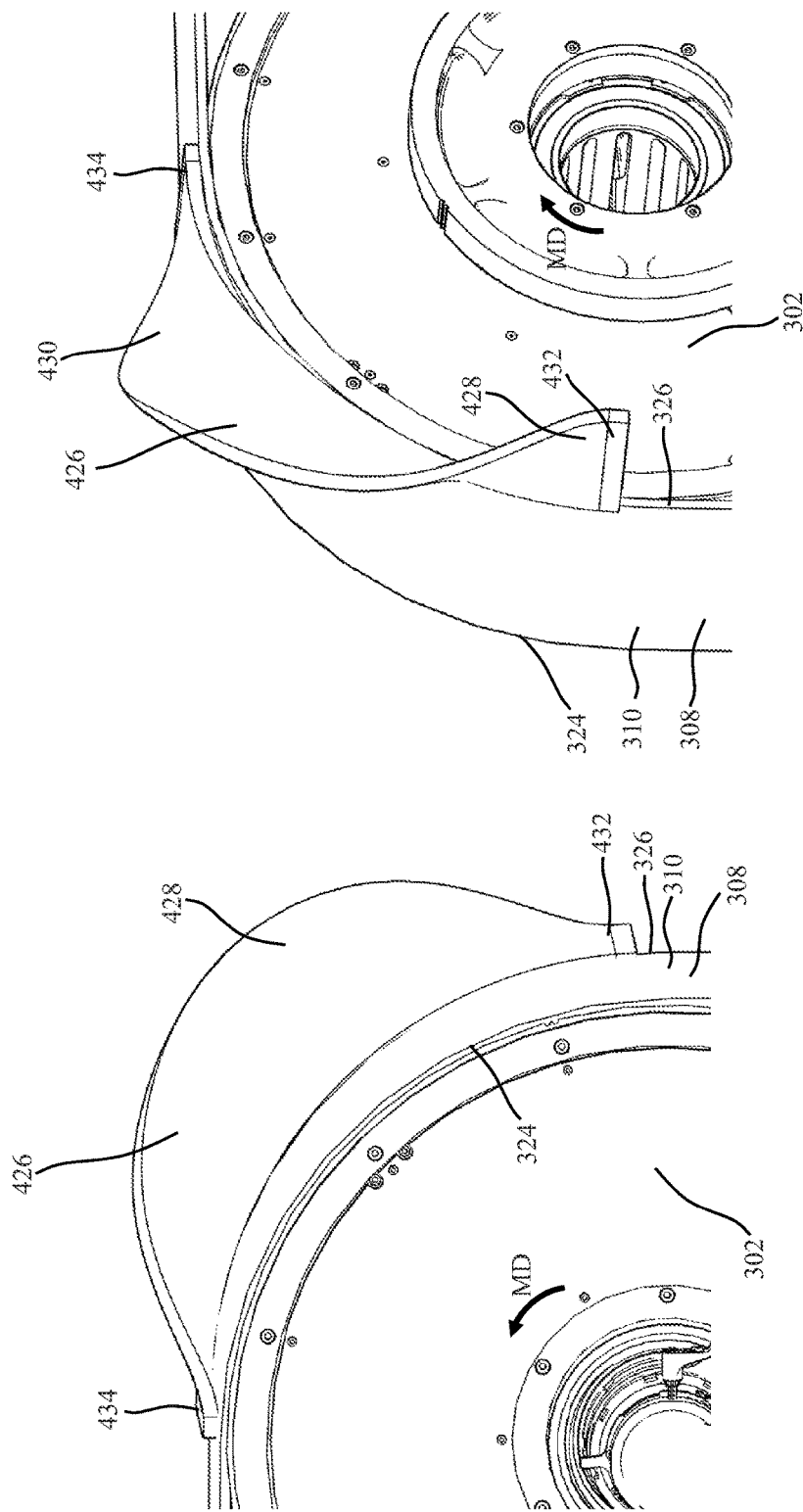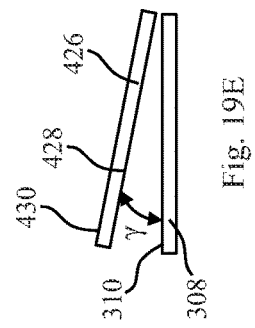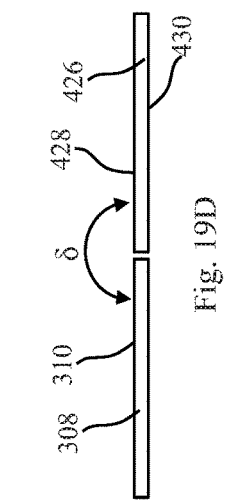

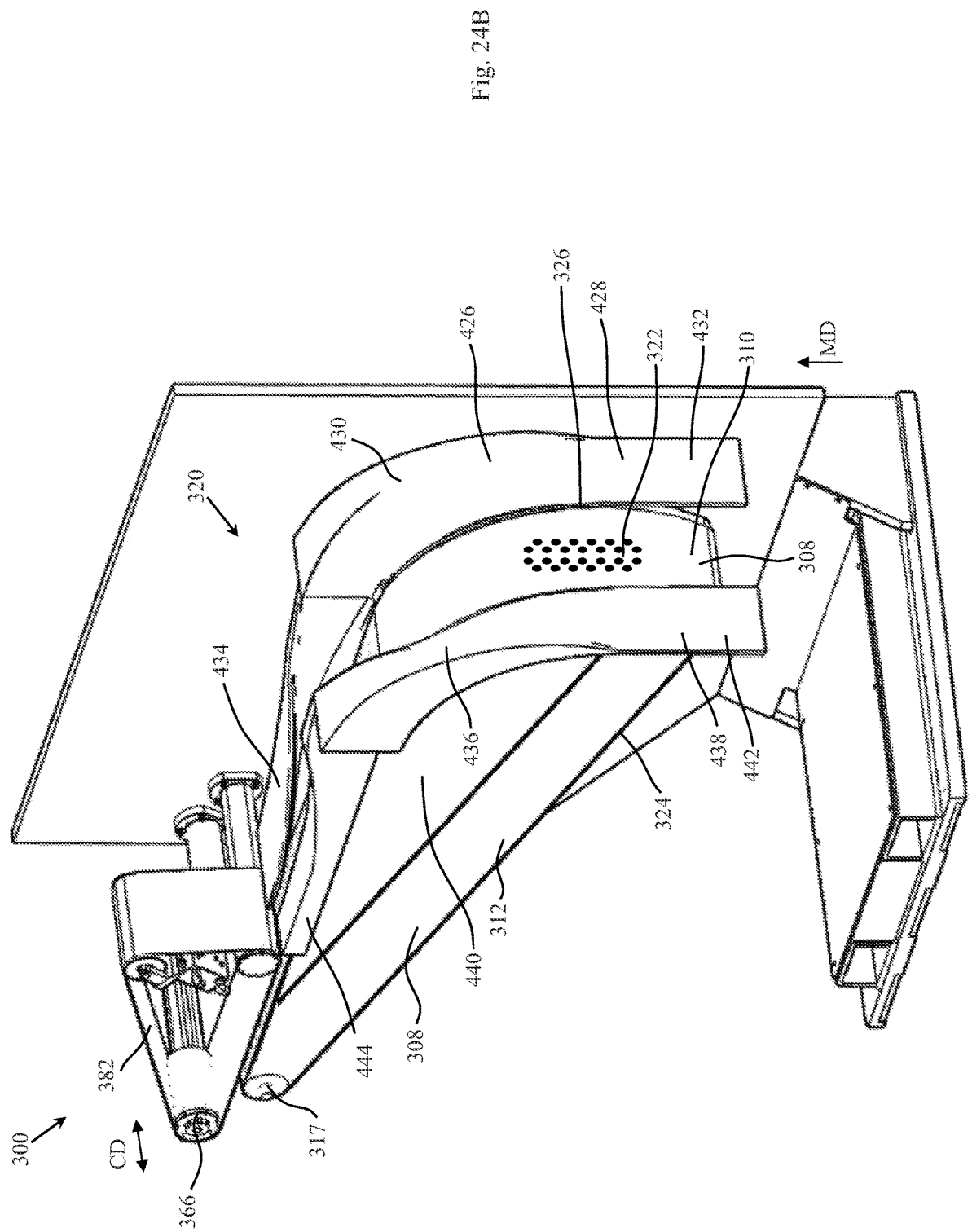

METHOD AND APPARATUS FOR ADVANCING AND FOLDING AN ABSORBENT ARTICLE

FIELD

The present disclosure relates to methods and apparatuses for manufacturing absorbent articles, and more particularly, methods and apparatuses for advancing and folding an absorbent article.

BACKGROUND

Along an assembly line, various types of articles, such as, diapers, may be assembled by adding components to and/or otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. In some cases, individual components created from advancing web or webs are combined with other individual components created from other advancing web or webs. Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing webs and component parts are subjected to a final knife cut to separate the webs into discrete diapers or other absorbent articles.

After the final knife cut, absorbent articles may undergo a folding process to bring front and rear waist regions together. In some processes, the folded absorbent articles may be rotated prior to packaging. For example, in some processes, the folded absorbent article may advance in a sideways orientation and may be rotated about 90 degrees to a desired orientation for packaging. Some processes for rotating a folded absorbent article may hold the front waist region of the absorbent article while the rear waist region is unrestricted from movement. Other processes may hold the rear waist region of the folded absorbent article, while the front waist region is unrestricted from movement. As a result, the unrestricted rear waist region of the folded absorbent article may be pulled away from the front waist region. Consequently, an absorbent article that is not fully folded, such as instances where the front waist region is not contacting the rear waist region, may get stuck in downstream processing and/or may cause the folded absorbent articles to be improperly packaged. Therefore, it would be beneficial to provide a process and apparatus for guiding and folding an absorbent article without also impeding the advancement of the absorbent article.

Further, folding of absorbent articles has traditionally taken place on relatively flat, linear stretches in the manufacturing process. Folding in this manner requires that the manufacturers first get the areas to be folded under control, usually by stretching these portions in a direction parallel to the flat, linear surface on which the absorbent article traverse. Subsequently, the process is required to move these portions to be folded from this stretched, parallel state to a folded state. This has traditionally required multiple devices, such as two of more conveyors, and vacuum to pull portions of the absorbent article into position for folding. Thus, this has been a relatively intricate process that requires a substantial amount of equipment and a substantial portion or footprint of the manufacturing process line. Therefore, it would be beneficial to provide a process and apparatus that permits folding the absorbent article in a relatively smaller footprint and takes advantage of the traversal of the absorbent article to aid in folding the absorbent article.

SUMMARY

Aspects of the present disclosure may include a method of transferring and folding discrete absorbent articles. In some embodiments, an apparatus for folding an absorbent article may include a drum including a fluid chamber and an outer circumferential drum surface surrounding a central longitudinal drum axis. The drum may be configured to rotate about the central longitudinal drum axis. The apparatus may also include a carrier member disposed on a portion of the outer circumferential drum surface. The carrier member may define a plurality of apertures. The plurality of apertures may be disposed over the fluid chamber of the drum. A first group of fluid nozzles may be positioned adjacent a first side of the drum, and a second group of fluid nozzles may be positioned adjacent the second side of the drum. The first group of fluid nozzles may be configured to engage a first end region of a belt of an absorbent article. The first end region of the belt extends in a first direction away from the central longitudinal drum axis. The second group of fluid nozzles may be configured to engage the second end region of the belt of the absorbent article. The second end region of the belt extends in the first direction away from the central longitudinal drum axis. The first end region of the belt may be folded onto a central region of the absorbent article and the second end region of the belt may be folded onto a central region of the absorbent article to form a folded absorbent article. A second carrier member positioned in facing relationship with the carrier member. The second carrier member may be configured to engage and transfer the folded absorbent article.

In some other embodiments, an apparatus for folding an absorbent article may include a drum including a fluid chamber and an outer circumferential drum surface surrounding a central longitudinal drum axis. The drum may be configured to rotate about the central longitudinal drum axis. The apparatus may also include a carrier member disposed on a portion of the outer circumferential drum surface. The carrier member may define a plurality of apertures. The plurality of apertures may be disposed over the fluid chamber of the drum. A first group of fluid nozzles may be positioned adjacent a first side of the drum and a first plow may be positioned adjacent the second side of the drum. The first group of fluid nozzles may be configured to engage a first end region of a belt of an absorbent article. The first end region of the belt extends in a first direction away from the central longitudinal drum axis. The first plow may be configured to engage the second end region of the belt of the absorbent article. The second end region of the belt extends in the first direction away from the central longitudinal drum axis. The first end region of the belt may be folded onto a central region of the absorbent article and the second end region of the belt may be folded onto a central region of the absorbent article to form a folded absorbent article. Further, a second carrier member may be positioned in facing relationship with the carrier member. The second carrier member may be configured to engage and transfer the folded absorbent article.

In some embodiments, an apparatus for folding an absorbent article may include a drum including a fluid chamber and an outer circumferential drum surface surrounding a central longitudinal drum axis. The drum may be configured to rotate about the central longitudinal drum axis. The apparatus may also include a carrier member disposed on a portion of the outer circumferential drum surface. The carrier member may define a plurality of apertures. The plurality of apertures may be disposed over the fluid chamber of the drum. A first plow may be positioned adjacent a first side of the drum, and a second plow positioned adjacent the second side of the drum. The first plow may be configured to engage a first end region of a belt of an absorbent article. The first end region of the belt extends in a first direction away from the central longitudinal drum axis. The second plow may be configured to engage the second end region of the belt of the absorbent article. The second end region of the belt extends in the first direction away from the central longitudinal drum axis. The first end region of the belt may be folded onto a central region of the absorbent article and the second end region of the belt may be folded onto a central region of the absorbent article to form a folded absorbent article. Further, a second carrier member may be positioned in facing relationship with the carrier member. The second carrier member may be configured to engage and transfer the folded absorbent article.

BRIEF DESCRIPTION OF THE DRAWINGS

FIG. 8A is a schematic, plan view of a partially folded diaper pant in a first orientation in accordance with one non-limiting embodiment of the present disclosure;

FIG. 8B is a schematic, plan view of a partially folded diaper pant in a second orientation in accordance with one non-limiting embodiment of the present disclosure;

FIG. 10A is a schematic, end view of a folding apparatus in accordance with one non-limiting embodiment of the present disclosure;

FIG. 10B is a schematic, top view of a portion of a carrier member with an absorbent article disposed thereon in accordance with one non-limiting embodiment of the present disclosure;

FIG. 12E is a schematic, sectional view of a folded diaper pant positioned on a carrier member in accordance with one non-limiting embodiment of the present disclosure;

FIG. 12F is a schematic, sectional view of a folded diaper pant positioned on a carrier member in accordance with one non-limiting embodiment of the present disclosure;

FIG. 19B is a schematic, perspective view of an arced plow positioned adjacent the drum in accordance with one non-limiting embodiment of the present disclosure;

FIG. 19C is a schematic, perspective view of an arced plow positioned adjacent the drum in accordance with one non-limiting embodiment of the present disclosure;

FIG. 19D is a schematic, end view of the position of an arced plow with respect to the carrier member in accordance with one non-limiting embodiment of the present disclosure;

FIG. 19E is a schematic, end view of the position of an arced plow with respect to the carrier member in accordance with one non-limiting embodiment of the present disclosure;

FIG. 24B is a schematic, perspective view of a folding device in accordance with one non-limiting embodiment of the present disclosure.

DETAILED DESCRIPTION

Figure 1:
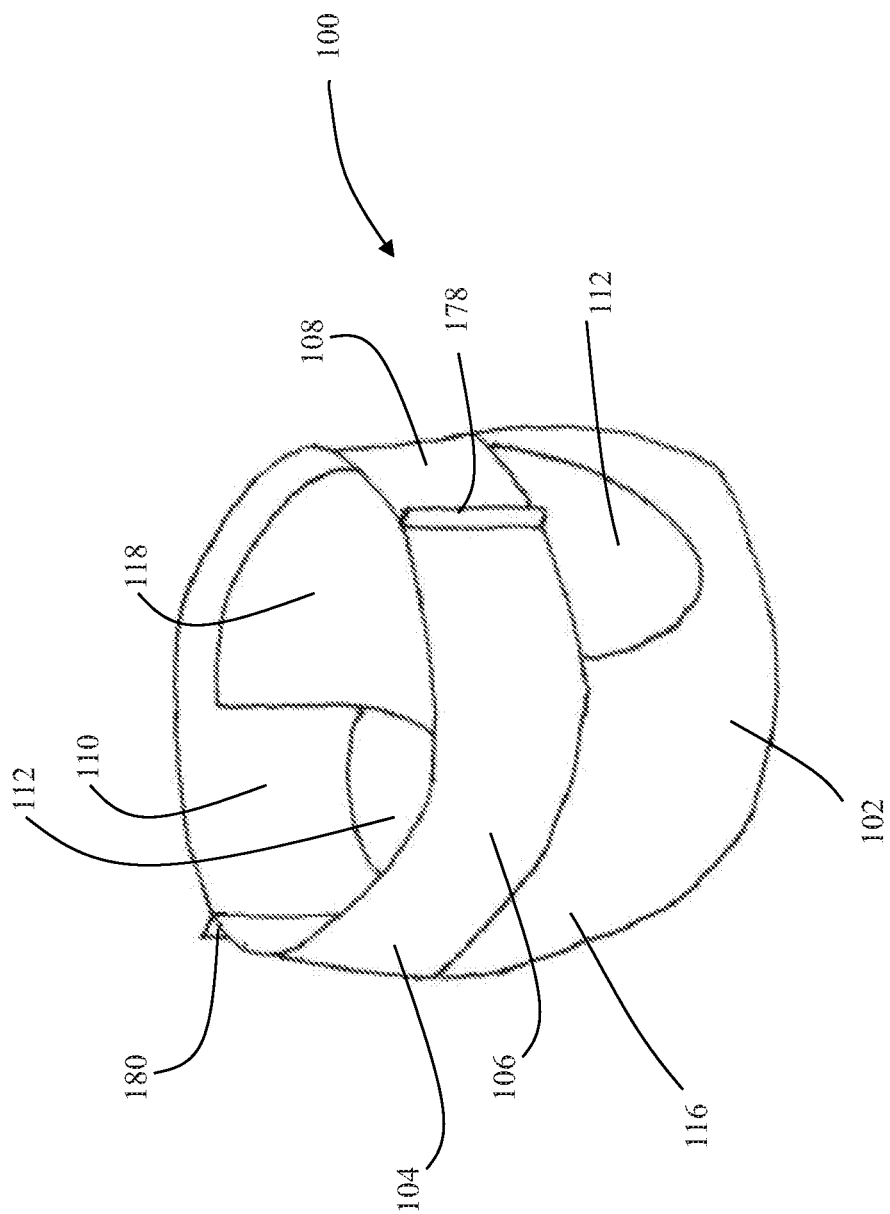
FIG. 1 is a schematic, perspective view of a diaper pant.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Joined" is used herein to encompass configurations whereby an element is directly secured to another element by affixing the element directly to the other element, and configurations whereby an element is indirectly secured to another element by affixing the element to intermediate member(s) which in turn are affixed to the other element.

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. $\frac{1}{10}$ or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is not parallel with, and usually perpendicular to, the machine direction.

"Pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed).

"Pre-fastened" refers herein to pant diapers manufactured and provided to consumers in a configuration wherein the front waist region and the back waist region are fastened or connected to each other as packaged, prior to being applied to the wearer. As such pant diapers may have a continuous perimeter waist opening and continuous perimeter leg openings designed for infant or adult wearers. As discussed in more detail below, a diaper pant can be preformed by various techniques including, but not limited to, joining together portions of the diaper using refastenable and/or permanent closure members (e.g., seams, heat bonds, pressure welds, adhesives, cohesive bonds, mechanical fasteners, etc.). In addition, pant diapers can be preformed anywhere along the circumference of the waist region (e.g., side fastened or connected, front waist fastened or connected, rear waist fastened or connected).

Aspects of the present disclosure involve methods and apparatuses for manufacturing absorbent articles, and more particularly, methods and apparatuses for controlling and folding an advancing absorbent article. As discussed in more detail below, in a converting process, partially folded absorbent articles may be transferred onto a transfer apparatus. The transfer apparatus may be adapted to rotate and reorient the partially folded absorbent articles. During the rotating and reorienting process, the partially folded absorbent articles may be subjected to centrifugal force, which may be referred to as inertial forces or forces resulting from centripetal acceleration, and/or gravitational forces. The converting apparatus may include a guide member that is located adjacent to the transfer apparatus and that is configured to control the movement of the advancing, partially folded absorbent articles.

The discrete absorbent article may include a chassis having longitudinally opposing first waist and second waist regions separated by a crotch region. The discrete absorbent article may be folded in a U-shape to bring the first waist region into a facing relationship with the second waist region to form a partially folded absorbent article. A ring-like elastic belt may connect the first waist region and the second waist region. The ring-like elastic belt may include a first elastic belt and a second elastic belt. The first and second elastic belts may each be defined by a first end region and a second end region laterally separated by a central region. The first end regions of the first and second elastic belts may be joined to form a first side seam and the second end regions of the first and second elastic belts may be joined to form a second side seam.

A converting apparatus of the present disclosure includes a transfer apparatus for advancing and orienting a partially folded absorbent article. The transfer apparatus includes a frame and a plurality of transfer members rotatably connected with the frame. The frame is rotatable about a first axis of rotation and the transfer members are rotatable about a second axis of rotation. The first axis of rotation extends in a different direction than the second axis of rotation. The first axis of rotation may be orthogonal to the second axis of rotation. The transfer members may define a receiving surface. The converting apparatus also includes a guide member located adjacent to the frame and forming a gap there between. The guide member may include a guide surface that is in a facing relationship with a receiving surface of the transfer member.

In operation, the first waist region of the folded absorbent article may be transferred from a first carrier apparatus to the transfer apparatus. The folded absorbent article may advance onto the receiving surface of the transfer member. The transfer apparatus advances the folded absorbent article in a machine direction about the first axis of rotation. The transfer member may concurrently rotate the folded absorbent article about the second axis of rotation. The transfer apparatus advances the folded absorbent article through a gap between the receiving surface and the guide surface.

The guide member operates to limit movement of the second waist region caused by centrifugal and/or gravitational forces that may act on the advancing folded absorbent article as the absorbent articles advance in the machine direction about the first axis of rotation. It is to be appreciated that limiting the movement of the second waist region may assist in advancing the absorbent article and also control the desired orientation of the partially folded absorbent article.

In some exemplary configurations, the guide surface of the guide member may have a curved shape that corresponds with the curved shape of the receiving surface. In addition, the guide surface may converge toward the receiving surface of the transfer member as the absorbent article advances in the machine direction. The folded absorbent article then advances from the transfer apparatus to a folding apparatus.

The folding apparatus may be used to fold the partially folded absorbent article to form a folded absorbent article. More specifically, portions of the first and second end regions of the first and second elastic belts, including the first and second side seams, may be folded onto the chassis of the absorbent article and/or the central region of the belt. It is to be appreciated that the first and second end regions may be folded such that both the first and second end regions are disposed on the chassis and/or the central region of the belt, or the first and second end regions may be folded in an overlapping configuration. As the absorbent article traverses about the folding apparatus, the first end region and the second end region of the belt is pulled away from the chassis and/or the central region of the belt by centrifugal and/or gravitational force. A folding assembly may be configured to engage and fold the first end region and the second end region when the first and second end regions are extended away from the chassis and/or the central region of the belt. The folding assembly folds the first and second end regions of the belt forming a folded absorbent article. The folded absorbent article may then be advanced to one or more additional processes.

As previously mentioned, the processes and apparatuses discussed herein may be used to guide and fold an advancing absorbent article. To help provide additional context to the subsequent discussion, the following provides a general description of absorbent articles in the form of diaper pants, which may be worn by children or adults, that may be guided in accordance with the methods and apparatuses disclosed herein. While the present disclosure relates to advancing absorbent articles in the form of diaper pants, it is to be appreciated that the methods and apparatuses disclosed herein may be used with various types of absorbent articles in folded, partially folded, or unfolded configurations. Furthermore, the methods and apparatuses disclosed herein may be used to guide partially assembled diaper components and/or diaper chassis in a variety of converting operations.

FIGS. 1, 2A, 3, and 4 illustrate an example of an absorbent article 100, such as a diaper, that may be assembled with the methods and apparatuses discussed herein. In particular, FIG. 1 shows a perspective view of an absorbent article 100 in a pre-fastened configuration, and FIG. 2A shows a plan view of the absorbent article 100 with the portion of the diaper that faces away from a wearer oriented towards the viewer. The absorbent article 100 shown in FIGS. 1 and 2A includes a chassis 102 and a ring-like elastic belt 104. As discussed below in more detail, a first belt 106 and a second belt 108, which are both elastic, are connected together to form the ring-like elastic belt 104.

The chassis 102 includes a first waist region 116, a second waist region 118, and a crotch region 120 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the absorbent article 100 and chassis 102 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

Figure 4:
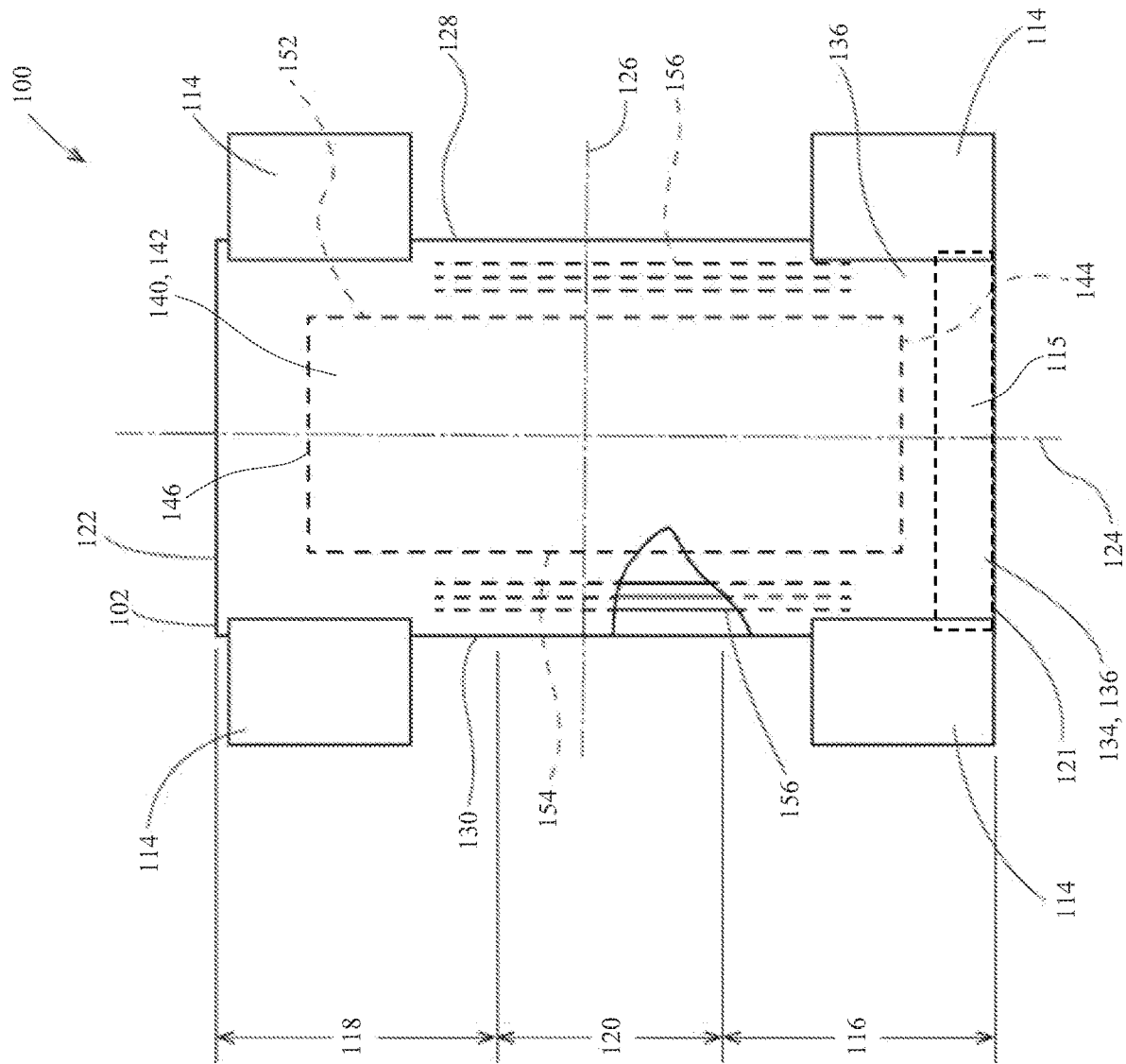
FIG. 4 is a partially cut-away, plan view of an absorbent article.

As shown in FIGS. 1, 2A, and 4 the absorbent article 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the absorbent article 100 may also include other features, such as a waistband, leg elastics, and/or leg cuffs to enhance the fit around the legs of the wearer.

The periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. When the absorbent article 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. Moreover, the crotch region 120 may be generally positioned between the legs of the wearer with the absorbent core 142 extending from the front waist region 116 through the crotch region 120 to the back waist region 118. The chassis 102 may have opposing longitudinal edges that are oriented generally parallel to the longitudinal centerline 124. However, for better fit, longitudinal edges 128, 130 may be curved or angled to produce, for example, an "hourglass" shape diaper when viewed in a plan view, such as disclosed in U.S. Pat. No. 8,939,957 and U.S. Patent Publication No. 2012/0277702.

It is also to be appreciated that a portion or the whole of the absorbent article 100 may also be made laterally extensible. The additional extensibility may help allow the absorbent article 100 to conform to the body of a wearer during movement by the wearer. The additional extensibility may also help, for example, allow the diaper 100, including a chassis 102 having a particular size before extension, to extend in the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper 100 may include a backsheet 136. The backsheet 136 may also define the outer surface 134 of the chassis 102. The backsheet 136 may be impervious or at least partially impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles that contact the diaper 100, such as bedsheets, clothes, and undergarments. The backsheet 136 may also include a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also include an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

In one embodiment, an adhesive may be applied to the garment-facing exterior of the backsheet for the purpose of holding the absorbent article in place by adhering to the wearer's underwear. Such adhesive may be especially desirable for use with adult incontinence and feminine hygiene type absorbent articles.

Also described above, the absorbent article 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets, and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916, 661; 6,545,197; and 6,107,539.

In some embodiments, the topsheet may comprise graphics such that depth perception is created as described in U.S. Pat. No. 7,163,528.

The absorbent article 100 may also include an absorbent assembly 140 that is joined to the chassis 102. The absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673, 402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprise primarily absorbent gelling material in amounts of at least about 60%, 70%, 80%, 85%, 90%, 95%, or even about 100%, where the remainder of the core may comprise a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

The absorbent article 100 may also include elasticized leg cuffs 156. It is to be appreciated that the leg cuffs 156 may be and are sometimes also referred to as leg bands, side flaps, barrier cuffs, elastic cuffs, or gasketing cuffs. The elasticized leg cuffs 156 may be configured in various ways to help reduce the leakage of body exudates in the leg regions. For example, in some embodiments, a gasketing leg cuff 160 may be positioned adjacent to the side edge 130, 128 of the chassis 102 and a barrier leg cuff 158 may be positioned between a gasketing leg cuff 160 and the longitudinal axis 124 of the absorbent article 100. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730 A1; and U.S. Patent Publication No. 2013/0255865 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, the absorbent article may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2A, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, a portion of the first end region 106a of the first elastic belt 106 is connected with a portion of the first end region 108a of the second elastic belt 108 at first side seam 178, and a portion of the second end region 106b of the first elastic belt 106 is connected with a portion of the second end region 108b of the second elastic belt 108 at second side seam 180 to define the ring-like elastic belt 104 as well as the waist opening 110 and leg openings 112.

As shown in FIGS. 2A, 2B, and 2C, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; discrete strands; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2A, 2B, and 2C, the belt elastic material may include a plurality of elastic strands 168 that may be referred to herein as outer, waist elastics 170 and inner, waist elastics 172.

Figure 2:
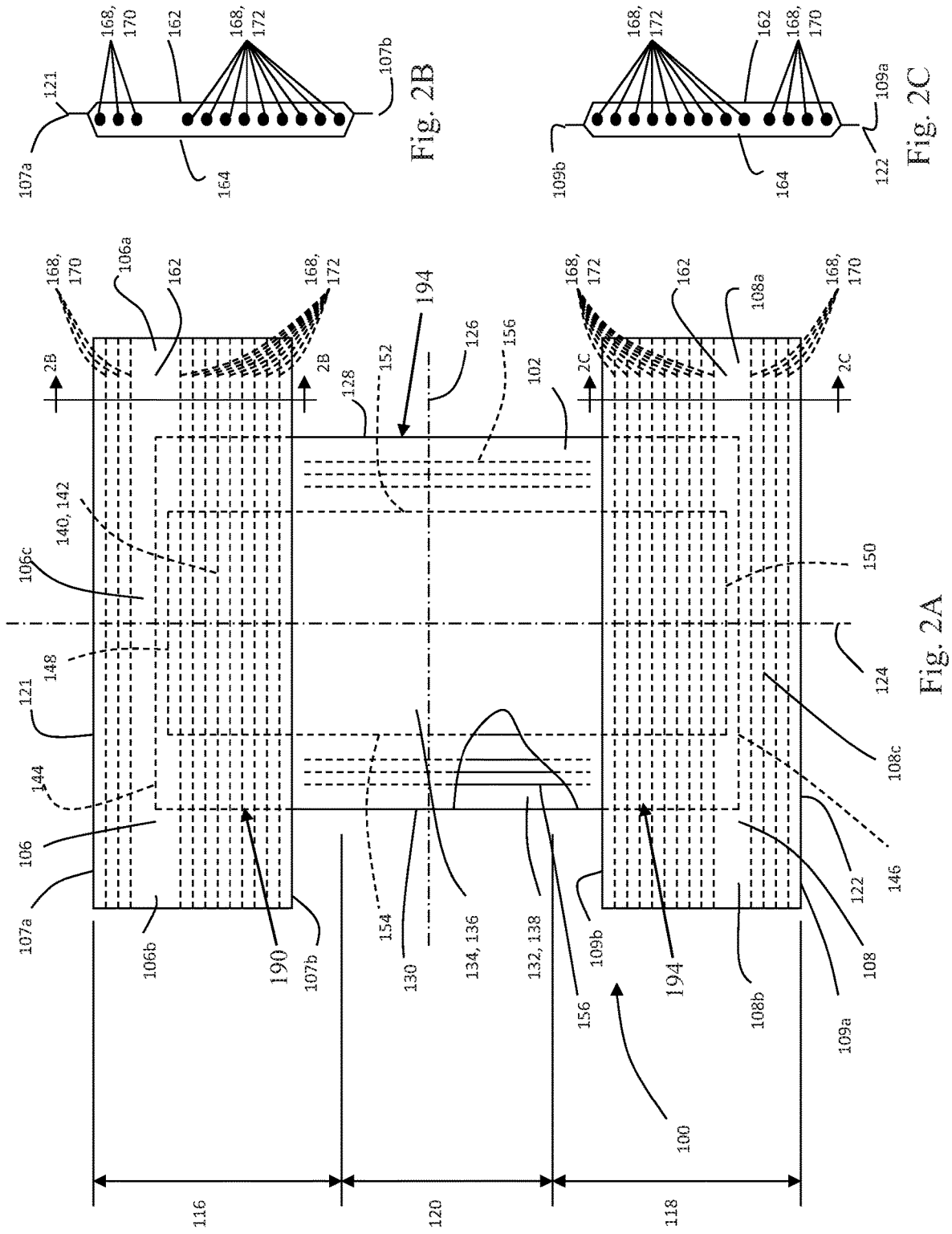
FIG. 2A is a partially cut-away, plan view of a diaper pant.
FIG. 2B is a cross-sectional view of the diaper pants of FIG. 2A taken along line 2B-2B.
FIG. 2C is a cross-sectional view of the diaper pants of FIG. 2A taken along line 2C-2C.

As shown in FIG. 2A, the outer, waist elastics 170 extend continuously laterally into and between the first and second opposing end regions 106a, 106b and across the central region 106c of the first elastic belt 106 and into and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 may not extend across the entirety of the central regions 106c, 108c of the first and second elastic belts 106, 108. Thus, for example, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2A.

Figure 3:
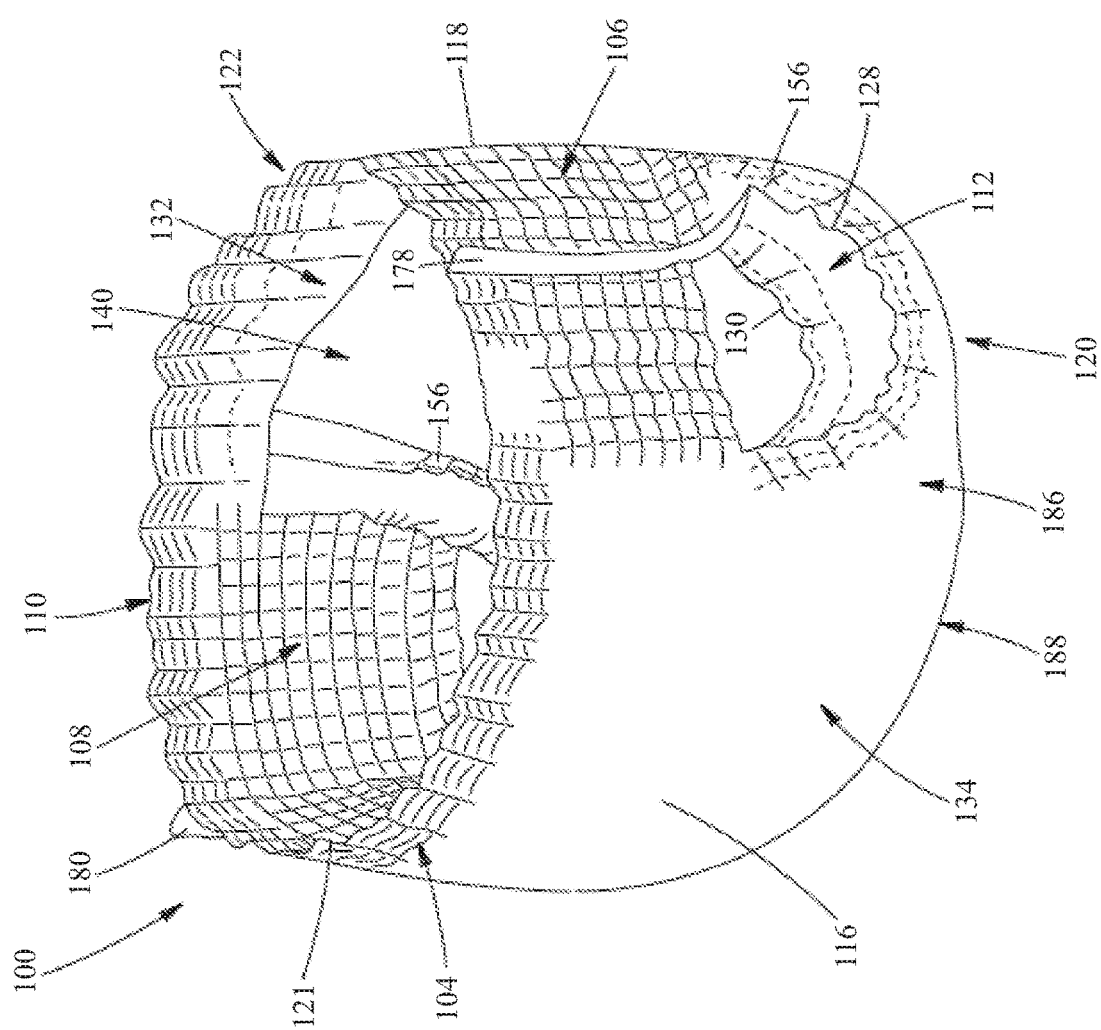
FIG. 3 is a schematic, perspective view of an absorbent article.

In some embodiments, as illustrated in FIG. 3, the absorbent article 100, which may be referred to herein as a diaper pant, comprises an absorbent main body 188, also referred to herein as chassis 102, to cover the crotch region of the wearer and a belt 104 extending transversely about the waist opening 110. The absorbent article 100 may also comprise an outer cover layer 186 to cover the main body 188. The belt 104 defines the waist opening 110. The belt 104, the main body 188 and/or the outer cover layer 186 jointly define the leg opening 112. One or more of the belt layers may extend from a first waist edge 121 in a first waist region 116 through the crotch region to a longitudinally opposing second waist edge 122 in a second waist region 118 and may form a portion or the whole of the outer surface of the absorbent article 100.

The absorbent main body 188, also referred to as a chassis 102, absorbs and contains body exudates disposed on the main body 188. In the embodiment shown in FIG. 2A, the main body 188 has a generally rectangular shape having a longitudinal centerline 124, a transverse centerline 126, left and right longitudinally extending side edges 128, 130 and front and back transversely extending end edges 144, 146. The main body 188 also has waist panels (i.e., a front waist panel 190 positioned in the front waist region 116 of the absorbent article 100 and a back waist panel 192 positioned in the back waist region 118) and a crotch panel 194 in the crotch region 30 between the front and back waist panels 190, 192.

The absorbent articles 100 may comprise first and second belts 106, 108 intended to encircle at least a portion of the waist of the wearer, the first and second belt portions 106, 108 being connected by a main body 188 forming the crotch region 120 of the absorbent article 100. The first and second belts 106 and 108 may be formed from a first belt layer forming a portion of the outer surface of the absorbent article, the first belt layer 106 may be formed of two longitudinally spaced webs of material. The first and second belts 106 and 108 may also comprise a second belt layer forming a portion of the inner surface of the absorbent article 100, the second belt layer may also be formed of two longitudinally spaced webs of material. The second belt layer may also be discontinuous and spaced apart in a transverse direction. The first and second belt layers may be formed of substantially the same material or may comprise different materials. The first and second belt layers may be formed from nonwovens, films, foams, elastic nonwoven, or combinations thereof. The first and second belts 106, 108 may also comprise an elastomeric material disposed between the first and second belt layers. The elastomeric material may comprise one or more elastic strands, elastomeric films, elastomeric ribbons, elastomeric nonwovens, elastomeric filaments, elastomeric adhesives, elastomeric foams, scrims or combinations thereof. A portion of the elastomeric material may be directly combined with the outer cover layer 186. The first and second belts 106, 108 may overlap at least a portion of the main body and one or both of the belt portions may be disposed on the outer surface of the main body or alternatively on the inner surface of the main body. A portion of the second belt layer and/or a portion of the first belt layer may be directly attached to the outer cover layer 186. Alternatively, the first belt and second belt 106, 108 may comprise longitudinally spaced webs of material forming a first surface of the belt wherein the webs are folded along the waist edge, or alternatively the leg opening edge, of the belt to wrap the elastomeric material and form at least a portion of the second surface of the belt. In other words, at least a portion of the inner surface and outer surface of each of the belt portions may be formed from a single web of material. It is to be appreciated that the outer cover layer 186, main body 188, and first and second belts 106, 108 may be configured in a number of ways such as disclosed in U.S. Pat. No. 9,072,632.

In some embodiment, as illustrated in FIG. 4, the article 100 may comprise an elasticized waistband 115. The elasticized waistband may provide improved fit and containment and may be configured to elastically expand and contract laterally to dynamically fit a wearer's waist. The elasticized waistband may extend longitudinally outwardly from the waist edge of the absorbent article 100 toward the edge of the absorbent core 200. In one embodiment, the absorbent article 100 may have two elasticized waistbands, one positioned in the back waist region 118 and one positioned in the front waist region 116, although other embodiments may be constructed with a single elasticized waistband. The elasticized waistband may be constructed in a number of different configurations including those described in U.S. Pat. Nos. 4,515,595 and 5,151,092. Further, the waistband may be constructed as disclosed in U.S. Publication Nos. 2012/0330262; 2012/0330263; and 2012/0330264 such that the waistband works in combination with the leg cuffs to provide improved fit and containment.

In some embodiments, the elasticized waistbands may comprise materials that have been "prestrained" or "mechanically prestrained" (i.e., subjected to some degree of localized pattern mechanical stretching to permanently elongate the material). In some embodiments, the materials may be prestrained using suitable deep embossing techniques. In other embodiments, the materials may be prestrained by directing the material through an incremental mechanical stretching system as described in U.S. Pat. No. 5,330,458. The materials may then be allowed to return to their substantially untensioned condition, thus forming a zero strain stretch material that is extensible, at least up to the point of initial stretching. Examples of zero strain materials are disclosed in U.S. Pat. Nos. 2,075,189; 3,025,199; 4,107,364; 4,209,563; 4,834,741; and 5,151,092. The waistband may be any shape and size that allows the absorbent article to fit the wearer as desired about the waist region.

In some embodiments, the waistband may be positioned between the side panels 114 and/or the back ears and/or front ears. In other embodiments the waistband may be positioned such that a portion of the waistband overlaps a portion of the side panels 114 and/or the back ears and/or the front ears.

In some embodiments, the absorbent article 100 may comprise side panels 114. The side panels 114 may be discrete from or integral with the chassis 100. A discrete side panel is formed as a separate element that is joined to the chassis 100. In some embodiments, this includes a plurality of side panels, e.g. FIG. 4 (also referred to as ear panels or side flaps) being joined to the side edges 128, 130 of the chassis in the front and/or rear waist regions 118 and 116. The side panel may be attached to the garment facing surface 132, the body facing surface 132, or between the garment facing surface 132 and the body facing surface 132, such as between the topsheet 138 and the backsheet 136. In some embodiments, the waistbands 112 can overlap the side panels to create a continuous belt-like structure (not shown).

In some embodiments, the side panels in the back waist region may connect with the garment facing surface of the absorbent article in the front waist region to form a waist circumference that may encircle the wearer during wear of the absorbent article. In other embodiments, the side panels disposed in the back waist region may connect with the side panels disposed in the front waist region at a seam, which forms a waist circumference that may encircle the wearer during wear of the absorbent article. The seam may be an overlapping seam or a butt seam. Further, in some embodiments, the seam may be refastenable, such that the side panels may be detached and reattached, or permanent, such that the seam may not be detached and reattached.

The side panels may comprise an inner nonwoven layer and an outer nonwoven layer and elastic elements, such as elastic strands or a film, therebetween. The inner and outer nonwoven layers may be joined using adhesive or thermoplastic bonds. Various suitable side panel configurations can be found in U.S. Pub. No. 2013/0211363.

An integral side panel is a portion, one or more layers, of the chassis that projects laterally outward from the longitudinal edge. The integral flap may be formed by cutting the chassis to include the shape of the flap projection.

While many of the embodiments illustrated in this application having belt-like side flaps are pant articles, taped articles may have belt-like side flaps disposed in one or both waist regions as well. The side panels may be any shape that allows the absorbent article to fit the wearer as desired about the waist region and the leg openings.

The absorbent article may also include a fastening system. When fastened, the fastening system interconnects the front waist region 116 and the rear waist region 118 resulting in a waist circumference that may encircle the wearer during wear of the absorbent article. This may be accomplished by ears or side panels 114, for example. The ears or side panels 114 in the back waist region interconnect with ears or side panels 114 in the front waist region or by the flaps or side panels in the back waist region interconnecting with the chassis 100 in the front waist region. The fastening system may comprises a fastener such as tape tabs, hook and loop fastening components, interlocking fasteners such as tabs and slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system may also provide a means for holding the article in a disposal configuration as disclosed in U.S. Pat. No. 4,963,140. The fastening system may also include primary and secondary fastening systems, as disclosed in U.S. Pat. No. 4,699,622. The fastening system may be constructed to reduce shifting of overlapped portions or to improve fit as disclosed in U.S. Pat. Nos. 5,242,436; 5,499,978; 5,507,736; and 5,591,152.

Particularly regarding feminine hygiene products, which are considered to be absorbent articles, one suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m$^2$ to about 35 g/m$^2$. The backsheet can be typically positioned adjacent the outer-facing surface of the absorbent core and can be joined thereto. For example, the backsheet may be secured to the absorbent core by a uniform continuous layer of adhesive, a patterned layer of adhesive, or an array of separate lines, spirals, or spots of adhesive. Illustrative, but nonlimiting adhesives, include adhesives manufactured by H. B. Fuller Company of St. Paul, Minn., U.S.A., and marketed as HL-1358J. An example of a suitable attachment device including an open pattern network of filaments of adhesive is disclosed in U.S. Pat. No. 4,573,986. Another suitable attachment device including several lines of adhesive filaments swirled into a spiral pattern is illustrated by the apparatus and methods discussed in U.S. Pat. Nos. 3,911,173; 4,785,996; and 4,842,666. Alternatively, the attachment device may include heat bonds, pressure bonds, ultrasonic bonds, dynamic mechanical bonds, or any other suitable attachment device or combinations of these attachment devices.

Further, the absorbent article, such as a feminine hygiene product, may comprise "wings" (not shown) intended to wrap the edges of the wearer's undergarments in the crotch region and/or affix the article to the undergarment to avoid poor folding and premature detachment. Exemplary absorbent articles comprising wings are disclosed in U.S. Pat. No. 8,039,685.

It is to be appreciated that the features of the absorbent article described herein may be excluded or combined to form various embodiments of an absorbent article.

As previously mentioned, the methods according to the present disclosure may be utilized to assemble discrete absorbent articles 100 and/or various components of absorbent articles 100. Although the following methods may be provided in the context of absorbent articles 100, as shown in FIGS. 1, 2, and 4, it is to be appreciated that the methods and apparatuses herein may be used with various process configurations and/or absorbent articles, such as for example, disclosed in U.S. Pat. Nos. 7,569,039 and 9,072,632; U.S. Patent Publication Nos. 2005/0107764 A1, 2012/0061016 A1, and 2012/0061015 A1; 2013/0255861 A1; 2013/0255862 A1; 2013/0255863 A1; 2013/0255864 A1; and 2013/0255865 A1; and U.S. Patent Application Ser. Nos. 62/136,003 filed on Mar. 20, 2015 entitled "DISPOSABLE ABSORBENT ARTICLES AND ARRAYS OF SAID ARTICLES COMPRISING VISUAL CHARACTERISTICS"; Ser. No. 14/996,683 filed on Jan. 15, 2016 entitled "ADULT DISPOSABLE ABSORBENT ARTICLES AND ARRAYS OF SAID ARTICLES COMPRISING ABSORBENT CORES HAVING CHANNELS"; and 62/286,662 filed on Jan. 25, 2016 entitled "ABSORBENT ARTICLES COMPRISING SPACERS."

Figure 5:
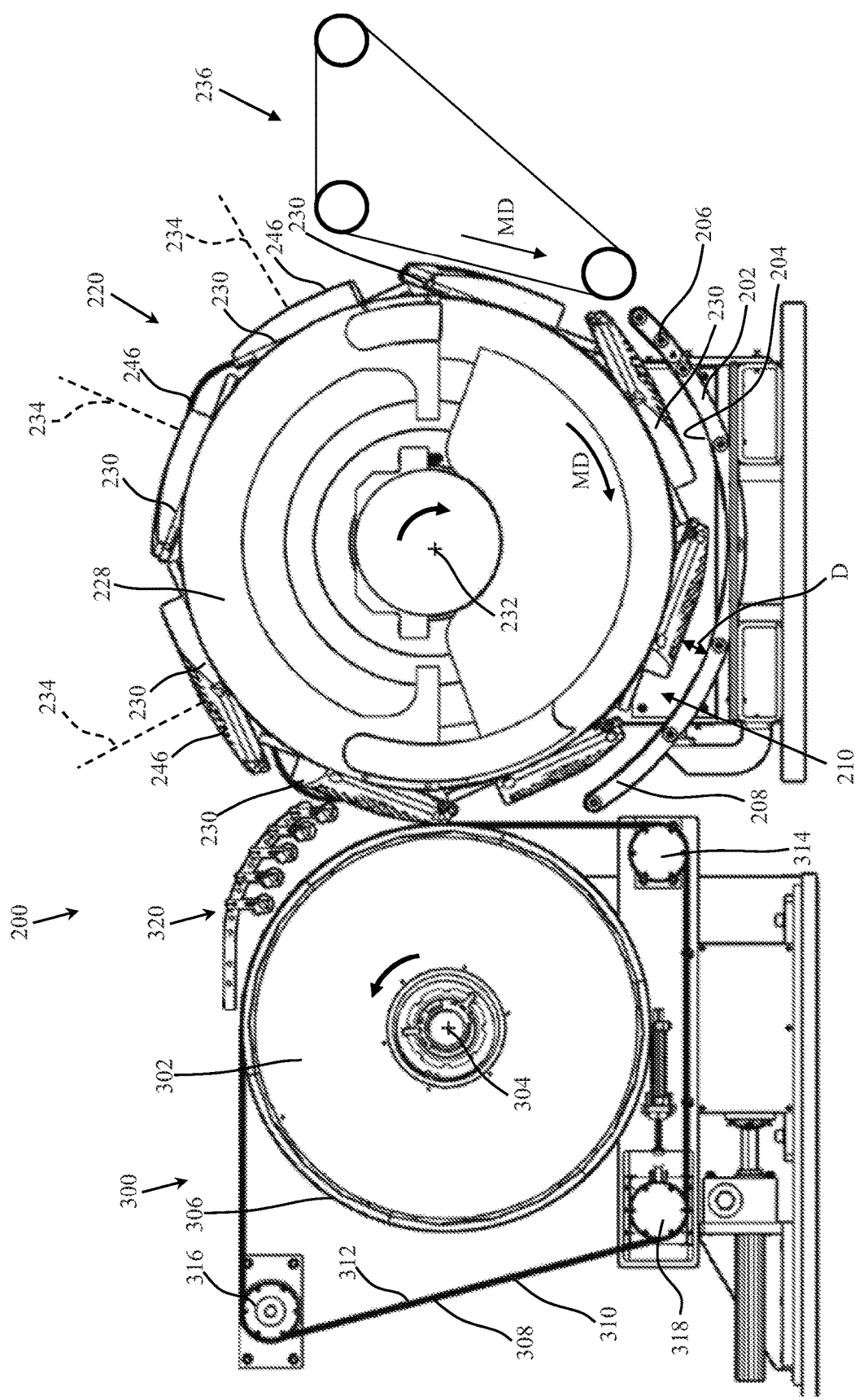
FIG. 5 is a schematic, side view of a converting apparatus including a transfer apparatus and a folding apparatus in accordance with one non-limiting embodiment of the present disclosure.

As discussed above, the methods and apparatuses disclosed herein may be used to guide and fold an advancing, partially folded diaper pant that is subjected to centrifugal and/or gravitational forces. FIG. 5 illustrates an exemplary converting apparatus 200 for guiding, orienting, and folding the absorbent article 100, which may be referred to herein as a diaper pant. The converting apparatus 200 may include a transfer apparatus 220 and a folding apparatus 300. The transfer apparatus 220 includes a frame 228 and a plurality of transfer members 230 rotatably connected with the frame 228. The frame 228 may be configured to rotate about a first axis of rotation 232 and the transfer members 230 may be configured to concurrently rotate about a second axis of rotation 234 that extends in a different direction than the first axis of rotation 232. Each transfer member 230 is defined by a receiving surface 246. Exemplary transfer apparatuses are described in U.S. Pat. No. 9,150,321 and US Patent Publication No. 2014/0113793. The converting apparatus 200 includes a first guide member 202 located adjacent to the frame 228 of the transfer apparatus 220 as to define a gap 210 there between. The guide member 202 includes a guide surface 204 that is positioned in a facing relationship with the receiving surfaces 246 of the transfer members 230. The guide member 202 may include a first end portion 206 and a second end portion 208, opposite the first end portion 206. The converting apparatus 200 may include a first carrier apparatus 236 positioned adjacent to the first end portion 206 of the guide member 202. The folding apparatus 300 may be positioned adjacent the second end portion 208 of the guide member 202.

The folding apparatus 300 may include a drum 302 configured to rotate about a central longitudinal drum axis of rotation 304. The drum 302 includes an outer circumferential drum surface 306. The folding apparatus 300 may also include a carrier member 308. The carrier member 308 may include a first surface 310 and a second surface 312. The first surface 310 may be configured to receive one or more absorbent articles. The second surface 312 may be in facing relationship with the outer circumferential drum surface 306. A portion of the second surface 312 of the carrier member 308 may be disposed about a portion of the outer circumferential drum surface 306. Further, the carrier member 308 may be disposed about a portion of one or more guide rollers. As illustrated in FIG. 5, in addition to being disposed about a portion of the outer circumferential drum surface 306, the carrier member 308 may traverse about a portion of a first guide roller 314, a second guide roller 316, and a third guide roller 318.

The folding apparatus 300 may also include a folding assembly 320. A folding assembly 320 may include one or more devices used to fold the absorbent article 100. The absorbent article 100 may be transferred from the transfer apparatus 200 to the folding apparatus 300. More specifically, the absorbent article 100 exits the second end portion 208 of the first guide member 202 while the absorbent article 100 is disposed on the receiving surface 246 of the transfer member 230. Air pressure may be used to aid in the removal of the absorbent article from the transfer member 230.

Upon removal from the transfer member 230, the absorbent article 100 is received by the first surface 310 of the carrier member 308. Vacuum may be used to aid in the transfer of the absorbent article onto the carrier member 308. The drum 302 and carrier member 308 traverse about the central longitudinal drum axis 304 causing the absorbent article 100 to advance to the folding assembly 320. The folding assembly 320 causes the first end region and the second end region to be disposed on the central body portion 196, which includes the chassis 102 and the central portion of the belt, of the absorbent article. The fold assembly 320 also aids in maintaining the absorbent article 100 in this folded configuration as the absorbent article continues to advance on the carrier member 308. The folding assembly 320 will be discussed in greater detail herein.

Each of the transfer apparatus 220, the folding apparatus 300, and the guide rollers may be driven by a motor. The motor may be any device that transmits rotational energy to the apparatus and/or roller. The motor may be operatively linked or operatively engaged with the apparatus and/or roller using any technique known to those skilled in the art such as, for example, a gear to gear connection, transmission belting and pulleys, gearboxes, direct couplings, and the like or any combination thereof. Each of the transfer apparatus 220, the folding apparatus 300, and the guide rollers may be driven by one or more motors.

Figure 6:
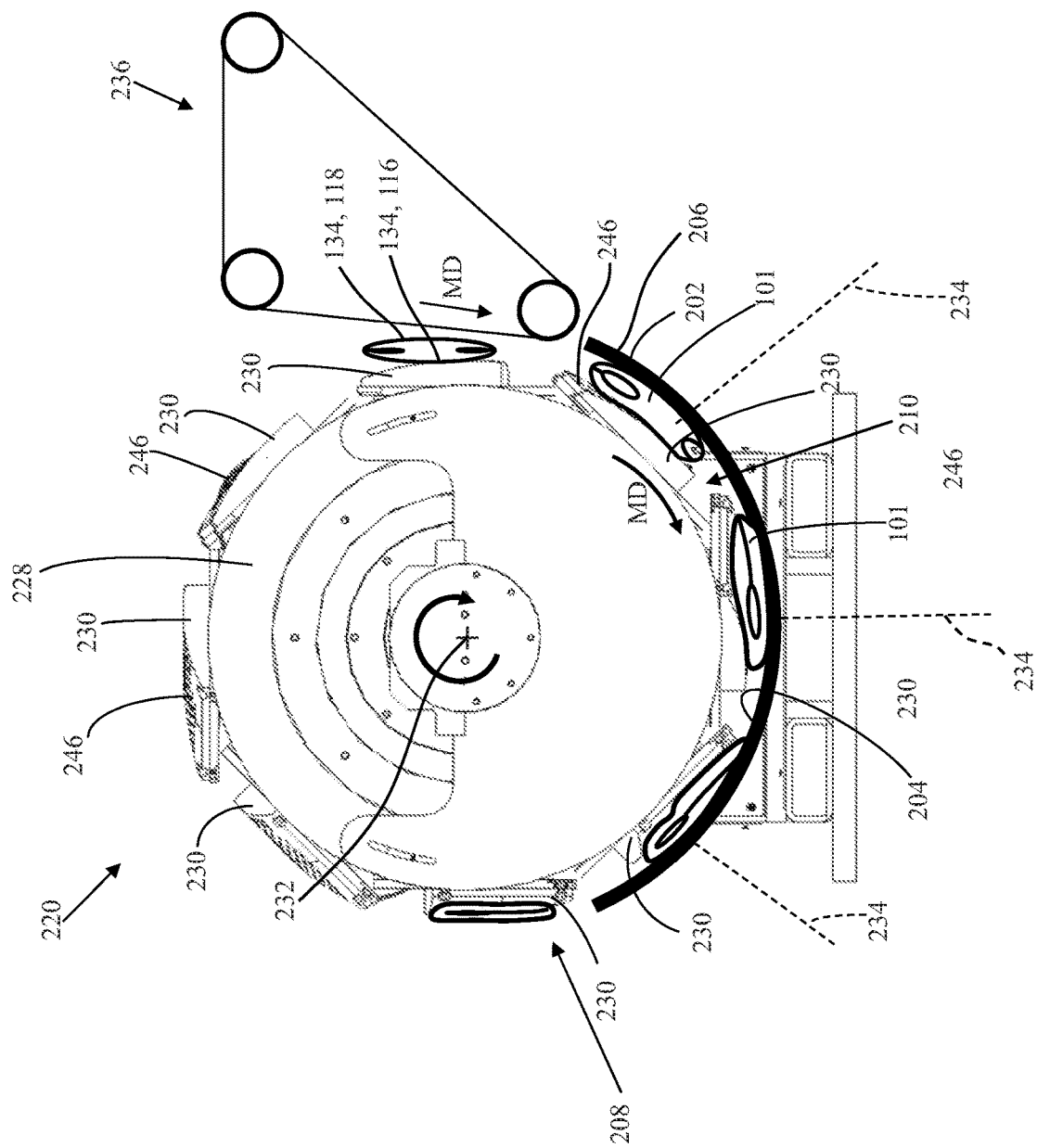
FIG. 6 is a schematic, side view of a transfer apparatus in accordance with one non-limiting embodiment of the present disclosure.

Referring to FIGS. 2A, 3, and 6, in operation, a partially folded diaper pant 101 may advance in a machine direction MD onto the first carrier apparatus 236. The outer surface 134 of the second waist region 118 of the folded diaper pant 101 may contact the first carrier apparatus 236 and the outer surface 134 of the first waist region 116 may face away from the first carrier apparatus 236. It is to be appreciated that the partially folded diaper pants 101 may be subjected to various methods and apparatuses of assembly and construction before being received by the first carrier apparatus 236. Examples of such upstream processes and apparatuses are disclosed in U.S. Pat. Nos. 8,820,513; 8,607,959; 8,833,542; and 8,720,666.

It is to be appreciated that the first carrier apparatus may be configured in various ways. For example, the first carrier apparatus 236 from and to which the partially folded diaper pants 101 are transferred may be rolls, drums, curved conveyors, linear conveyors, and/or discrete heads following a curvilinear path, for example. The first carrier apparatus 236 may be operated at variable speed. The first carrier apparatuses 236 may be moving at a different surface velocity or at the same surface velocity as the transfer apparatus. For example, the transfer apparatus 220 may pick up the partially folded diaper pant 101 from the first carrier apparatus 236 at the same velocity as is applied to the partially folded diaper pant 101 upon removal.

From the first carrier apparatus 236, the outer surface 134 of the first waist region 116 of the folded diaper pant 101 may advance onto a receiving surface 246 of a transfer member 230 as shown in FIG. 6. The partially folded diaper pant 101 may be folded such that the inner surface 132 of the first waist region 116 is in contact with the inner surface 132 of the second waist region 118 when the folded diaper pant 101 advances onto the receiving surface 246 of the transfer member 230. The transfer apparatus 220 may rotate the partially folded diaper pant 101 in the machine direction MD about a first axis of rotation 232. The transfer member 230 may advance the partially folded diaper pant 101 through the gap 210 between the transfer member 230 and the guide member 202.

Figure 6A:
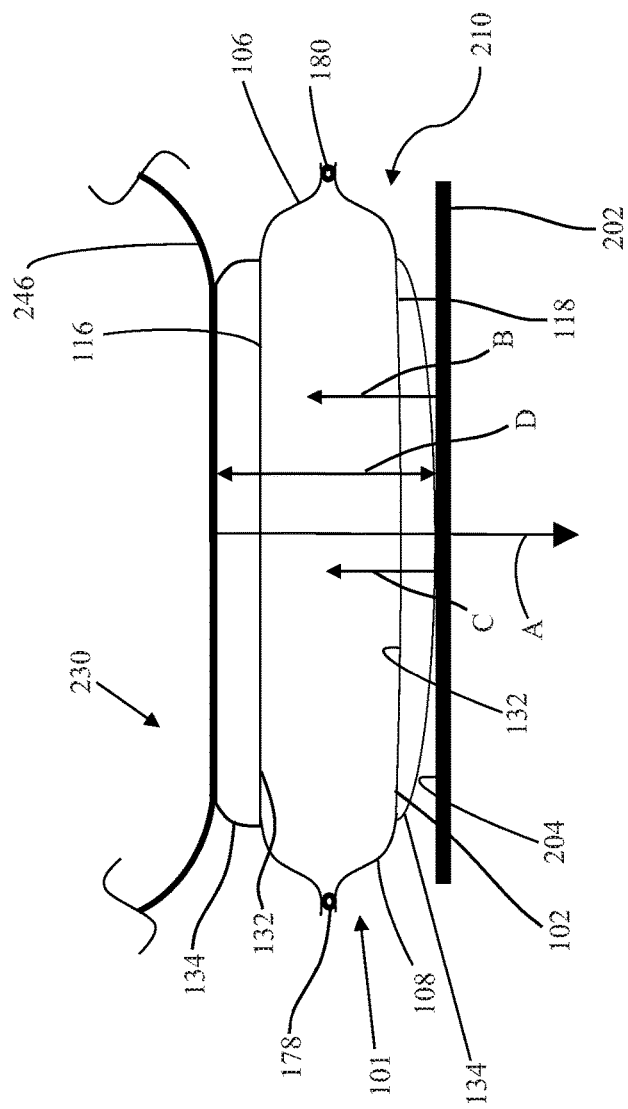
FIG. 6A is a schematic, sectional view of a folded diaper pant positioned in a gap between a guide member and a transfer member in accordance with one non-limiting embodiment of the present disclosure.

Referring to FIGS. 6 and 6A, as the transfer member 230 rotates about the first axis of rotation 232, centrifugal and/or gravitational forces may pull the second waist region 118 of the partially folded diaper pant 101 in a first direction, A, toward the guide surface 204. As the frame 228 rotates about the first axis of rotation 232, the transfer member 230 may concurrently rotate about the second axis of rotation 234. The guide surface 204 may converge towards the receiving surface 246 of the transfer member 230 such that the inner surface 132 of the second waist region 118 moves in a second direction, B, toward the first waist region 116 as the folded diaper pant 101 advances through the gap 210. As shown in FIG. 6A, the first and second side seams 178 and 180 extend away from the first waist region 116 and the second waist region 118. As the guide surface 204 converges toward the receiving surface 246, the second waist region 118 may move in the section direction, B, toward the first waist region 116. As shown in FIG. 5, the partially folded diaper pant 101 may advance from the gap 210 and onto the folding apparatus 300. Vacuum may be intermittently interrupted to remove the partially folded diaper pant 101 from the receiving surface 246 of the transfer member 230.

Figure 7A:
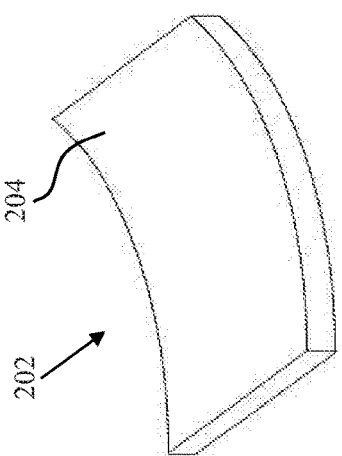
FIG. 7A is a schematic, perspective side view of an exemplary guide member in accordance with one non-limiting embodiment of the present disclosure.

As shown in FIG. 7A, the first guide member 202 includes a guide surface 204. With reference to FIGS. 5 and 6, the shape of the guide surface 204 may correspond with the shape of the receiving surface 246 of the transfer member 230. For example, the guide surface 204 may be curved, such as shown in FIG. 7A, to match the curved shape of the receiving surfaces 246. While it is shown that the guide surface 204 has a curved shape, it is to be appreciated that the guide surface 204 may be configured to have various other shapes. The first guide member 202 may be stationary relative to the frame 228. In some exemplary configurations, the first guide member 202 may be connected with the frame 228. It is to be appreciated that the first guide member 202 may be connected with to the frame 228 in various ways.

The guide surface 204 may be configured to minimize the coefficient of friction between the guide surface 204 and the partially folded diaper pant 101. Exemplary guide surfaces include low-coefficient of friction plasma coating, polished steel, and polytetrafluoroethylene. In some configurations, the coefficient of friction between the guide surface 204 and the partially folded diaper pant 101 may be in the range of about 0.2 to about 0.35.

Figure 7B:
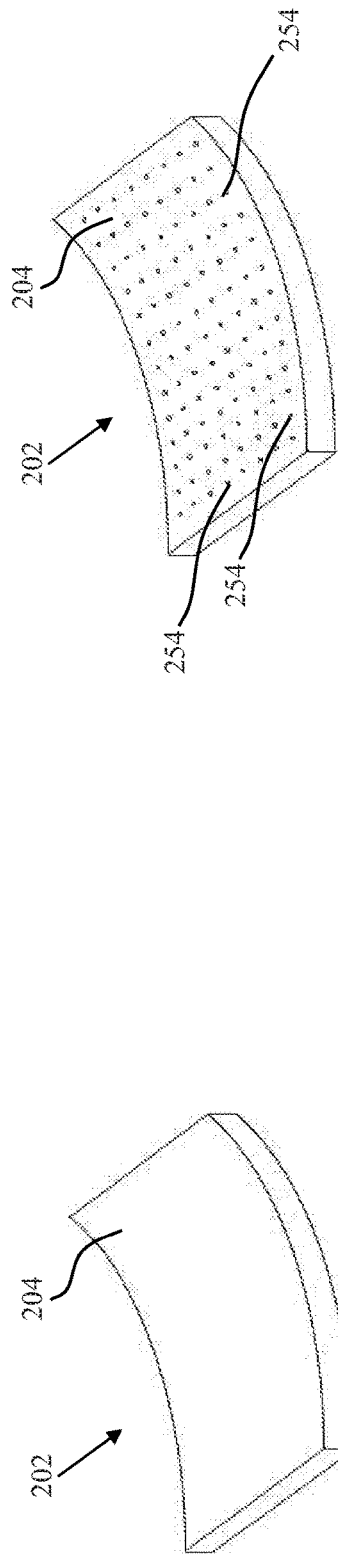
FIG. 7B is a schematic, perspective side view of an exemplary guide member having apertures in accordance with one non-limiting embodiment of the present disclosure.

In some exemplary configurations, with reference to FIG. 7B, the coefficient of friction between the guide surface 204 and the partially folded diaper pant 101 may be further reduced by applying a positive pressure to the outer surface 134 of the second waist region 118 of the folded diaper pant 101. As shown in FIG. 7B, the guide surface 204 may include a plurality of apertures 254. The apertures 254 may be used to apply a positive pressure to the folded diaper pant as the folded diaper pant advances adjacent to the guide member 202. The positive pressure helps to reduce the contact between the partially folded diaper pant 101 and the guide surface 204 as the partially folded diaper pant 101 advances in the machine direction MD. As a result of applying a positive pressure to the partially folded diaper pant 101, the coefficient of friction may be reduced between the partially folded diaper pant 101 and the guide surface 204. In turn, the first guide member 202 may limit the movement of the second waist region 118 in the first direction, A, without inhibiting the advancement of the folded diaper pant 101 in the machine direction MD. It is to be appreciated that the apertures 254 shown in FIG. 7B may be arranged in various configurations on the guide surface 204. Applying a positive pressure to the folded diaper pant 101 may result in a coefficient of friction between the folded diaper pant 101 and the guide surface 204 of less than about 0.35. It is also to be appreciated that the first guide member 202 may apply positive air pressure to the partially folded diaper pant 101 such that the partially folded diaper pant 101 moves in a direction C, which is opposite the direction A, toward the receiving surface 246.

As previously mentioned, the guide surface 204 may be configured or shaped to converge towards the receiving surface 246 of the transfer member 230. As such, the gap 210 between the receiving surface 246 and the guide surface 204 may become smaller as the transfer member 230 rotates around the first axis of rotation 232. For example, as illustrated in FIG. 5, the gap 210 may be defined by a minimum distance D between the receiving surface 246 and the guide surface 204. The receiving surface 246 may be located a first distance from the guide surface 204 when the transfer member 230 is relatively near the first end portion 206 of the guide member 202. Moreover, the receiving surface 246 may be located a second distance from the guide surface 204 when the transfer member 230 is relatively near the second end portion 208 of the guide member 202. The second distance may be less than, greater than, or equal to the first distance. In some exemplary configurations, the minimum distance D from the receiving surface 246 to the guide surface 204 may gradually decrease from the first end portion 206 of the guide member 202 to the second end portion 208 of the guide member 202. However, it is to be appreciated that in some exemplary configurations the minimum distance D between the receiving surface 246 to the guide surface 204 may be constant for a length of the guide member 202 and then may gradually decrease.

It is to be appreciated that, in some embodiments, the transfer apparatus 220 may not include a guide member 202. The transfer member 230 may provide sufficient vacuum pressure on the partially folded pant 101 to maintain the position of the partially folded pant 101 against the receiving surface 246 as the transfer member 230 traverses about the first axis of rotation 232 and the transfer member 230 traverse about the second axis of rotation 234.

Referring back to FIG. 6, the partially folded diaper pant 101 may transfer from the first carrier apparatus 236 to the transfer apparatus 220 in a first orientation. As shown in FIG. 8A, in the first orientation 222, the longitudinal centerline 124, also referred to herein as the longitudinal axis, of the partially folded diaper pant 101 extends in the cross direction CD. The transfer apparatus 220 advances the partially folded diaper pant 101 in the machine direction MD about the first axis of rotation 232 while the transfer member 230 rotates the partially folded diaper pant 101 about the second axis of rotation 234. The partially folded diaper pant 101 then advances through the gap 210 between the transfer member 230 and the guide member 202. Centrifugal and/or gravitational forces may pull the second waist region 118 of the folded diaper pant 101 in the first direction, A, toward the first guide member 202. The first guide member 202 limits movement of the second waist region 118 in the first direction, A, while allowing the folded diaper pant 101 to advance in the machine direction MD with minimal frictional resistance between the folded diaper pant 101 and the guide surface 204. As the frame 228 continues rotating about the first axis of rotation 232, the minimum distance D may decrease moving the second waist region in the second direction, B, and the folded diaper pant 101 may fold such that the first waist region contacts the second waist region before advancing from the gap 210 and onto the folding apparatus 300. The partially folded diaper pant 101 is in a second orientation 224 as the partially folded diaper pant 101 advances onto the folding apparatus 300. In the second orientation 224, the longitudinal centerline 124 of the folded diaper pant 101 extends in the machine direction MD as shown in FIG. 8B.

It is to be appreciated that the frame 228 of the transfer apparatus 220 may be configured in various different ways. For example, the frame 228 may be configured as a drum, a conveyor, and/or a series of rollers.

Is it also to be appreciated that the guide member may be configured in various ways. In some exemplary configurations, the transfer apparatus 220 may be configured to rotate the partially folded diaper pants before advancing the folded diaper pants through the gap 210 between the transfer member 230 and the guide member 202. As such, the guide member 202 may only extend along a portion of the frame 228 adjacent the folding apparatus 300. In some other exemplary configurations, the guide member 202 may be configured as a series of rollers or as a conveyor, such as disclosed in U.S. Patent Publication No. 2014/0113793. In a configuration where the guide member is configured as a series of rollers or as a conveyor, the guide surface 204 may be moveable in order to guide the partially folded diaper pants in the machine direction MD. The guide surface 204 may be configured such that the coefficient of friction between the guide surface 204 and the partially folded diaper pant is relatively low. The rollers and the conveyor may be configured to apply a positive pressure to the partially folded diaper pant advancing through the gap 210.

Figure 9:
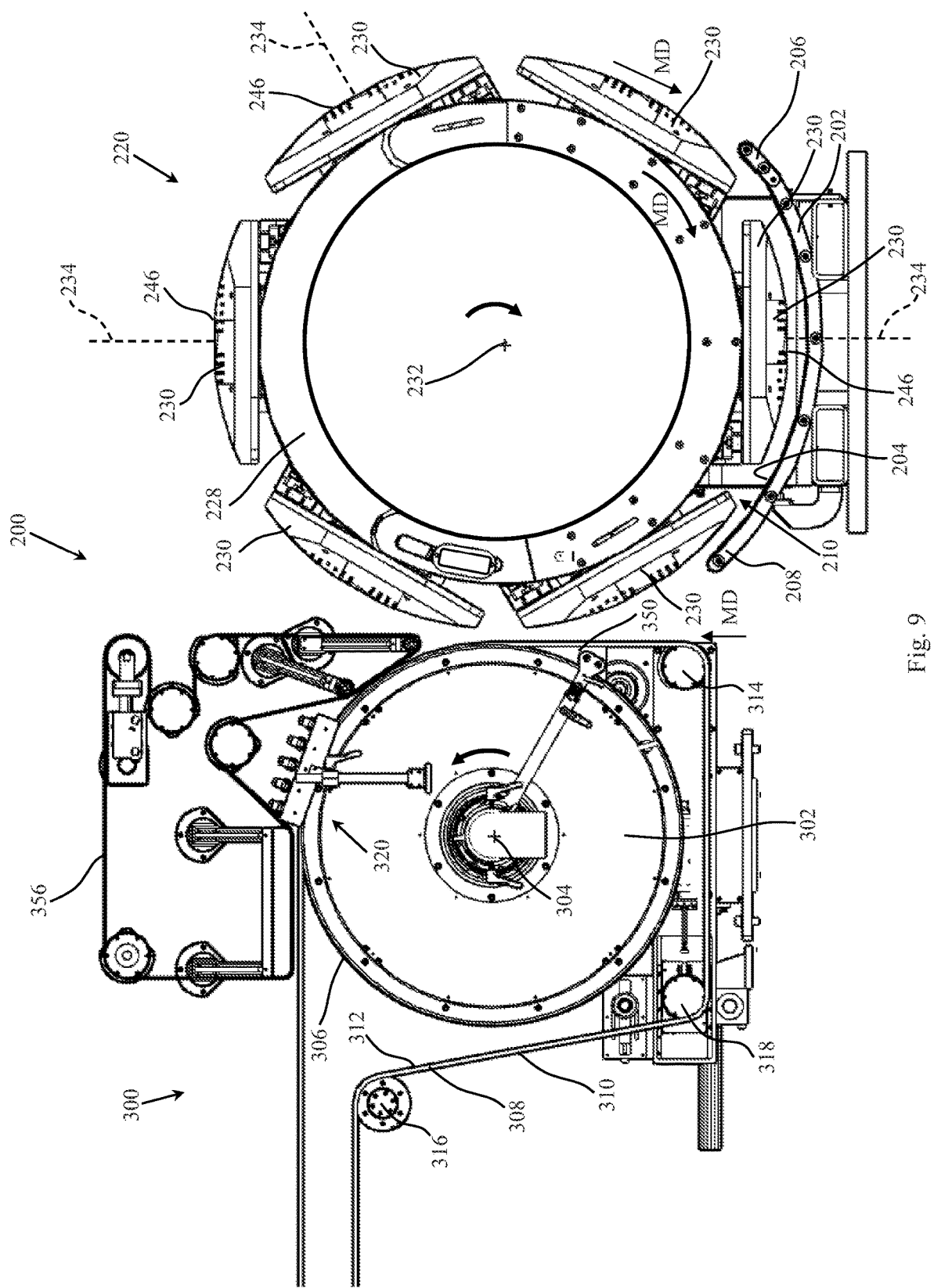
FIG. 9 is a schematic, side view of a converting apparatus including a transfer apparatus and a folding apparatus in accordance with one non-limiting embodiment of the present disclosure.

FIG. 9 illustrates the converting apparatus 200. As previously discussed, the absorbent article 100, or partially folded pant 101, may be transferred and oriented by the transfer apparatus 220. The partially folded pant 101 may be advanced such that the partially folded pant 101 may be transferred from the transfer apparatus 220 to the folding apparatus 300. The partially folded pant 101, also referred to herein as a partially folded absorbent article, may be removed from the receiving surface 246 of the transfer member 230 to the carrier member 308. Fluid pressure may be used to aid in transferring the partially folded pant 101. In some embodiments, the transfer member 230 may provide positive fluid pressure to push the partially folded pant 101 away from the receiving surface 246. The drum 302 may provide negative fluid pressure, or vacuum pressure, such that the partially folded pant 101 is drawn toward the carrier member 308. In some other embodiments, the transfer member 230 may provide no pressure. However, the transfer member 230 also may not provide any vacuum pressure. Thus, the partially folded pant 101 is free to leave the receiving surface 246. The drum 302 may provide vacuum pressure to pull the partially folded pant 101 to the carrier member 308 or the outer circumferential drum surface 306.

It is to be appreciated that the transfer apparatus 220 may be a device as disclosed in U.S. Pat. Nos. 8,820,513; 8,607,959; 8,833,542; and 8,720,666. More specifically, the device as described in the aforementioned U.S. patents may transfer the partially folded pant or another component of an absorbent article to the folding apparatus 300. The device may be configured to rotate the partially folded pant or other component at a constant speed or a variable speed. The device may repitch the partially folded pant or component to change the spacing between the partially folded pants or components. Further, the device may be used to rotate the partially folded pant or other component from a first orientation to a second orientation. Further still, the device may adjust radially such that the partially folded pant is accepted from a first carrier at a first position and the partially folded pant is transferred from the device to the folding apparatus 300 or a second carrier at a second position, which may be different than the first position.

As illustrated in FIGS. 10A and 10B, the partially folded pant 101 may be disposed on a portion of the carrier member 308. More specifically, the partially folded pant 101 may be disposed on the first surface 310 of the carrier member 308 and be positioned over one or more apertures 322 defined by the carrier member 308. The one or more apertures 322 may be any size or shape such that the one or more apertures 322 are able to provide adequate vacuum pressure on the partially folded pant 101. For example, the one or more apertures 322 may be circular, oval, square, rectangular, or any other regular or irregular shape. The one or more apertures 322 may be arranged in any manner such that adequate vacuum pressure is provided to hold and traverse the partially folded pant 101. In some embodiments, the one or more apertures 322 may extend substantially continuously in the machine direction MD along the carrier member 308. In some other embodiments, the one or more apertures 322 may be arranged into groups of one or more apertures, and these groups of one or more apertures may be spaced in the machine direction MD along the carrier member 308. The spacing of the group of apertures may be based upon the size of the absorbent article to be processed. Thus, the gap or spacing between the groups of apertures may correspond to the spacing between absorbent articles as they are transferred to the carrier member 308. Fluid may circulate through the one or more apertures 322 toward the central longitudinal drum axis 304 to provide the vacuum pressure on the partially folded pant 101. The partially folded pant 101 may be disposed on one or more of the apertures 322, as illustrated in FIG. 10B. The partially folded pant 101 may be positioned on the carrier member 308 such that the chassis 102 is positioned between a first carrier edge 324 and a second carrier edge 326, which is opposite the first carrier edge 324 in the cross direction CD. The belt 106, 108 may be positioned within the first carrier edge 324 and the second carrier edge 326, or portions of the belt 106, 108, such as the first end region and the second end region, may extend beyond the first carrier edge 324 and the second carrier edge 326, as illustrated in FIG. 10B.

It is to be appreciated that the carrier member 308 may be configured in various different ways. For example, the carrier member 308 may be configured as a conveyor, a mesh belt, and/or a screened belt. The carrier member 308 may include one or more conveyors or belts.

As previously discussed, the belt 106, 108 may include a first end region 106a, 108a, a second end region 106b, 108b, and a central region 106c, 108c that extends between the first end region and the second end region. Further, a portion of the first end regions 106a, 108a are joined at a first side seam 178 and a portion of the second end regions 106b, 108b are joined at a second side seam 180. The central region 106c, 108c may be disposed on the one or more apertures 322. The one or more apertures 322 may provide a vacuum pressure such that the central region 106c, 108c remains in contact with the carrier member 308 or the outer circumferential drum surface 306 as the partially folded pant 101 is advanced about the central longitudinal drum axis 304. It is to be appreciated that the one or more apertures 322 may be present in a portion of each of the first end regions 106a, 180a and second end regions 106b, 108b. However, the one or more apertures 322 may not create a vacuum force on the portions of the belt 106, 108 that are intended to be folded.

Figure 11B:
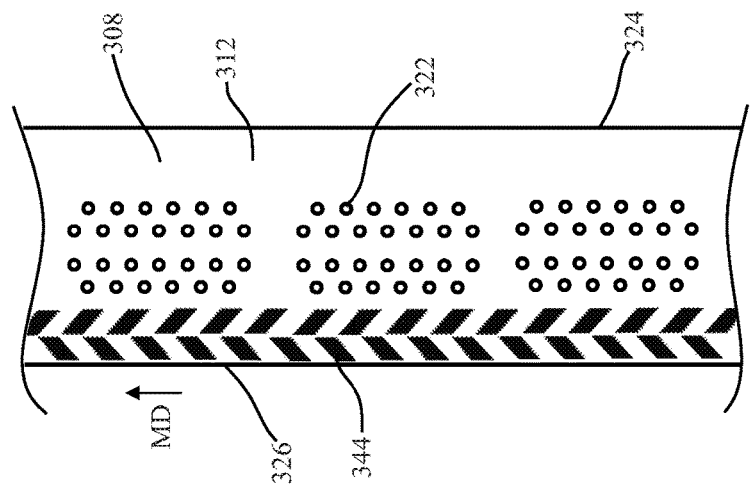
FIG. 11B is a schematic, top view of a portion of a carrier member in accordance with one non-limiting embodiment of the present disclosure.
Figure 11A:
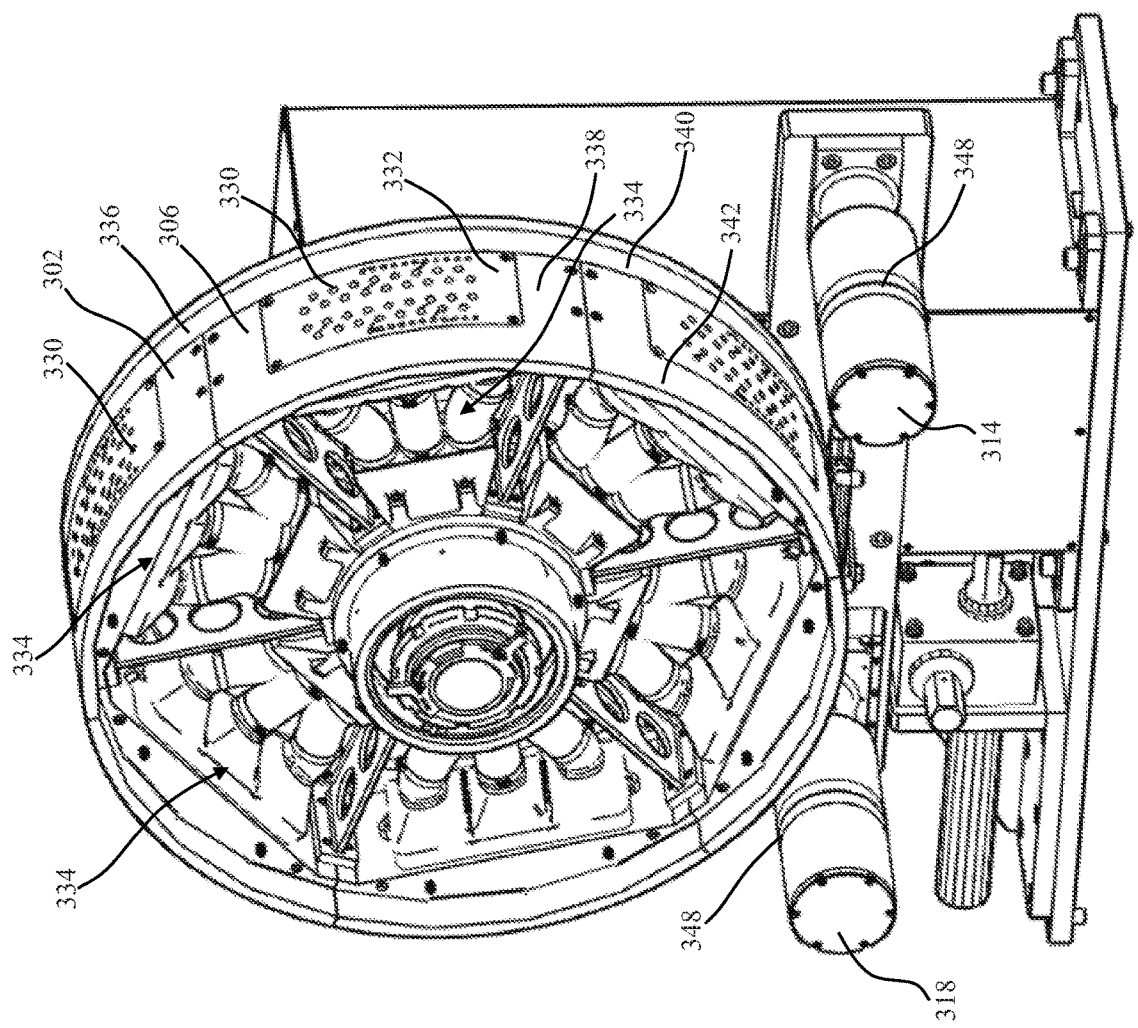
FIG. 11A is a schematic perspective view of a drum in accordance with one non-limiting embodiment of the present disclosure.

As illustrated in FIGS. 9 and 10A, the carrier member 308 may be disposed over a portion of the outer circumferential drum surface 306. Thus, to create the aforementioned vacuum pressure on the partially folded pant 101, fluid may flow through the one or more apertures 322 defined by the carrier member 308 and into the drum 302. As illustrated in FIG. 11A, the outer circumferential drum surface 306 may define one or more apertures 330. Similar to the above, the apertures may be any size and shape such that adequate vacuum pressure is maintained on the partially folded pant 101. The one or more apertures 330 may be positioned in any pattern such that adequate vacuum pressure is maintained on the partially folded pant 101. Further, the pattern, shape, and size of the apertures 330 defined by the outer circumferential drum surface 306 may be the same or different than the apertures 322 defined by the carrier member 308. For example, the apertures 330 defined by the outer circumferential drum surface 306 may be slot-shaped and the apertures defined by the carrier member 308 may be substantially circular shaped. In some embodiments, the one or more apertures 330 defined by the outer circumferential drum surface may be positioned on a removable plate 332. The plate 332 may be removed from the outer circumferential drum surface and a plate 332 comprising a different pattern, size, and/or number of apertures may be attached to a portion of the outer circumferential drum surface 306. The removable plates 332 may allow the same drum 302 to be used to manufacture various sized consumer products. It is to be appreciated that, in some embodiments, the drum 302 may not include a plate 332 and the apertures 330 may be defined by a fixed outer circumferential surface 306.

Each plate 332 or portion of apertures 330 may be in fluid communications with a fluid chamber 334. The fluid chamber 334 may pull fluid through the one or more apertures 330 toward the central longitudinal drum axis 304 or the fluid chamber 334 may push fluid through the one or more apertures 330 away from the central longitudinal drum axis 304. Each fluid chamber 334 may be fluidly connected to a fluid source, not shown. The fluid source may be used to generate the fluid flow through the fluid chamber 334. Each fluid chamber 334 may be controlled independently. Further, each fluid chamber 334 may include one or more fluid regions. Each fluid region within a fluid chamber 334 may be controlled independently. More specifically, a group of one or more apertures may be in fluid communication with a fluid chamber 334. For example, the fluid chamber 334 may be divided into three fluid regions. A portion of the group of one or more apertures may be in fluid communication with each of the three fluid regions such that the release of fluid may be controlled independently to each of the three fluid regions.

The drum may include a drive portion 336. The drive portion may be defined by the outer circumferential drum surface 306. The drive portion may extend about the central longitudinal drum axis 304. The drive portion 336 may be disposed in a first edge portion 340, a second edge portion 342 opposite the first edge portion 340, or a central portion 338 positioned between the first edge portion 340 and the second edge portion 242 of the outer circumferential surface 306. The central portion 338 may extend in the cross direction between the first edge portion 340 and the second edge portion 342. In some embodiments, the one or more apertures 330 and/or the plate 332 may be disposed in the central portion 338 of the outer circumferential drum surface 306 and the drive portion may be disposed in at least one of the first edge portion 340 and the second edge portion 342. The drive portion 336 may be positioned such that the apertures 330 may act on the chassis when the absorbent article is disposed on the outer circumferential drum surface 306. Further, by offsetting the drive portion 336 to either or both of the first edge portion 340 and the second edge portion 342, the drive portion 336 does not interfere with the apertures 330 and, thus, the position of the chassis of the absorbent article may be maintained against the outer circumferential drum surface 306 or the carrier member 308 as the drum traverses about the central longitudinal drum axis 304.

In some embodiments, the drive portion 336 may be positioned in the central portion 338. The one or more apertures may extend through the drive portion 336 so as to not interrupt the vacuum force or pressure force that may be applied to the absorbent article. In some embodiments, the drive portion 336 may extend across one or more of the first edge portion 340, the second edge portion 342, and the central portion 338. The one or more apertures may extend through the drive portion 336 to maintain adequate force on the absorbent article.

It is to be appreciated that in some embodiments, the drum 302 may include more than a single drive portion. For example, the drum 302 may include a first drive portion disposed in the first edge portion and a second drive portion disposed in the second edge portion. It is also to be appreciated that the one or more apertures may extend into the first edge portion 340 or the second edge portion 342. For example, if the drive portion 336 is positioned in the first edge portion 340, the one or more apertures may be disposed on the central portion 338 and the second edge portion 342.

The drive portion 336 may include a first plurality of teeth. The first plurality of teeth may extend about the drive portion 336 and include any number of tooth patterns, such as disclosed in U.S. Patent Publication No. 2015/0158672 and U.S. Patent Publication No. 2015/0158673. Similarly, the carrier member 308 may include a second plurality of teeth 344. The second plurality of teeth 344 may be disposed on the surface of the carrier member 308 that is in contact with outer circumferential drum surface 306. Thus, the second plurality of teeth 344 may be disposed on either the first surface 310 or the second surface 312 of the carrier member 308. For example, as illustrated in FIG. 11B, the second surface 312 of the carrier member 308 includes a second plurality of teeth 344. The carrier member 308 may be positioned about a portion of the drum 302 such that the second surface 312 of the carrier member is disposed on a portion of the outer circumferential drum surface 306 and the first plurality of teeth operatively engage, such as by interlinking or meshing, with the second plurality of teeth 344. The first plurality operatively engage with the second plurality of teeth 344 such that as the drum 302 rotates about the central longitudinal axis 304, the carrier member 308 is driven by the drive portion such that the carrier member 308 rotates with the drum about the central longitudinal axis. The first plurality of teeth interlinking or meshing with the second plurality of teeth 344 also aid in alignment of the carrier member 308 on the outer circumferential drum surface 306. Further, the teeth aid in maintaining alignment of the one or more apertures 322 defined by the carrier member 308 with the one or more apertures 330 defined by the drum 302.

As previously discussed, the drum 302 may include any number of drive portions. For example, the drum 302 may include a first drive portion 336 positioned in the first edge portion 340 of the outer circumferential drum surface 306 and a second drive portion (not shown) positioned in the second edge portion 342 of the outer circumferential drum surface 306. Similarly, the carrier member may include a second plurality of teeth 344, as previously discussed, and a third plurality of teeth (not show) configured to mesh with the first and second drive portions. Thus, the carrier member may include any number of toothed portions which are configured to mesh with the drive portions of the drum 302. The one or more apertures defined by the carrier member 308 may extend through the plurality of teeth, if necessary, such that adequate force is maintained on the absorbent article.

The drum 302 may be driven by a motor as previously discussed. The motor operatively engages the drum 302 causing the drum to rotate about the central longitudinal drum axis 304. As the driven drum 302 rotates about the central longitudinal drum axis 304, the drum 302 drives the carrier member 308 causing the carrier member 308 to traverse in the machine direction MD.

It is also to be appreciated that any one of the guide rollers may also include a roller drive portion 348. The roller drive portion 348 may operate such as previously described with respect to the drive portion 336. The roller drive portion 348 may be configured to operatively engage the plurality of teeth of the carrier member 308 or another carrier member. In some embodiments, the guide roller may be driven by a motor and the drum 302 may or may not be driven by a motor. In embodiments where the drum is not driven by a motor and the guide roller is driven by a motor, the driven guide roller may cause the carrier member 308 to traverse in the machine direction MD. Further, the carrier member 308 may engage the un-driven drum 308 such that the carrier member 308 operatively engages the drum 308, such as by intermeshing teeth, and causes the drum 308 to rotate about the central longitudinal drum axis 304.

It is also to be appreciated that the carrier member 308 may traverse with the drum 302 about the central longitudinal drum axis 304 by a frictional engagement between the carrier member 308 and the outer circumferential drum surface 306.

In some embodiments, it is to be appreciated that the partially folded pant 101 may be disposed directly onto the outer circumferential drum surface 306 of the drum 302 and the partially folded pant 101 may transfer to a downstream carrier member from the drum 302.

Referring to FIG. 9, in some embodiments, the drum 302 may include a transition portion 350. The transition portion 350 may be joined to and extend from the outer circumferential drum surface 306. The transition portion 350 may be disposed on the outer circumferential drum surface 306. The transition portion 350 includes an external surface defining one or more apertures. The pattern, shape, and size of apertures may be the same as or different than the apertures 322 defined by the carrier member 308 and/or the apertures 330 defined by the drum 302 so long as adequate vacuum pressure acts on the partially folded pant 101. Similar to the above, the apertures defined by the transition portion 350 may be used to create a vacuum pressure on the absorbent article or to create a positive pressure on the absorbent article. The external surface 350 may support a portion of the carrier member 308. The transition portion 350 extends from the outer circumferential drum surface 306 to aid in transitioning the absorbent article from the receiving surface 246 of the transfer member 230 onto the carrier member 308 and/or the outer circumferential drum surface 306.

Figure 12A:
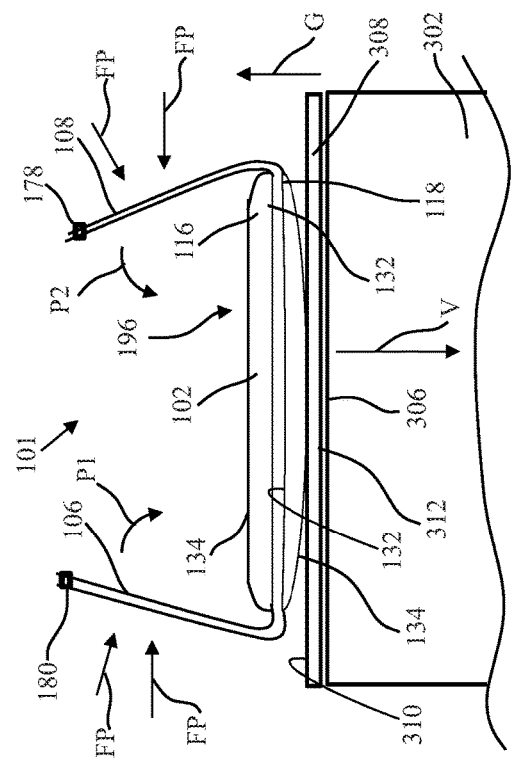
FIG. 12A is a schematic, sectional view of a partially folded diaper pant positioned on a carrier member in accordance with one non-limiting embodiment of the present disclosure.

The partially folded pant 101 may advance in the MD on the outer circumferential drum surface 306 or the carrier member 308. In some embodiments, the partially folded pant 101 may advance in the machine direction MD such that a folded region 328 advances first and the waist edge 121, 122 follows the folded region 328, as illustrated in FIG. 10B. However, it is to be appreciated that either the folded region 328 or the waist edge 121, 122 may be the first to advance in the machine direction MD. Referring to FIGS. 10B and 12A, the chassis 102 of the partially folded diaper pant 101 may be disposed on one or more apertures configured to create a vacuum pressure on the central body portion 196, which includes the chassis 102 and the central region 106c, 108c of the belt 106, 108, to hold the central body portion 196 in position as the drum 302 traverses about the central longitudinal axis 304. The vacuum pressure acts to pull the central body portion 196 in a direction V, toward the central longitudinal drum axis 304. As the drum 302 traverses about the central longitudinal drum axis 304, the centrifugal and/or gravitational forces may pull a portion of the first belt 106 and a portion of the second belt 108 of the partially folded diaper pant 101 in a direction G. Once the centrifugal and/or gravitational forces act to pull the first end region and the second end region of the first belt 106 and the second belt 108 in the direction G, a portion of the first belt 106 and a portion of the second belt 108 may each form an angle α with respect to the first surface 310 of the carrier member 308. The angle α is measured from the surface of the carrier member 308 to a plane P intersecting the proximal end 198 of the end region of the belt and the distal end 199 of the end region of the belt. The angle α may be from about 30 degrees to about 135 degrees and/or from about 60 degrees to about 110 degrees, including all 0.1 degree increments therebetween.

It is to be appreciated that one or more rigid guard members (not shown) may be positioned adjacent to or partially overlapping the drum 302 to prevent the first end region and the second end region of the belt from interfering with the rotation of the drum or any other process equipment placed adjacent the drum 302.

Figure 13:
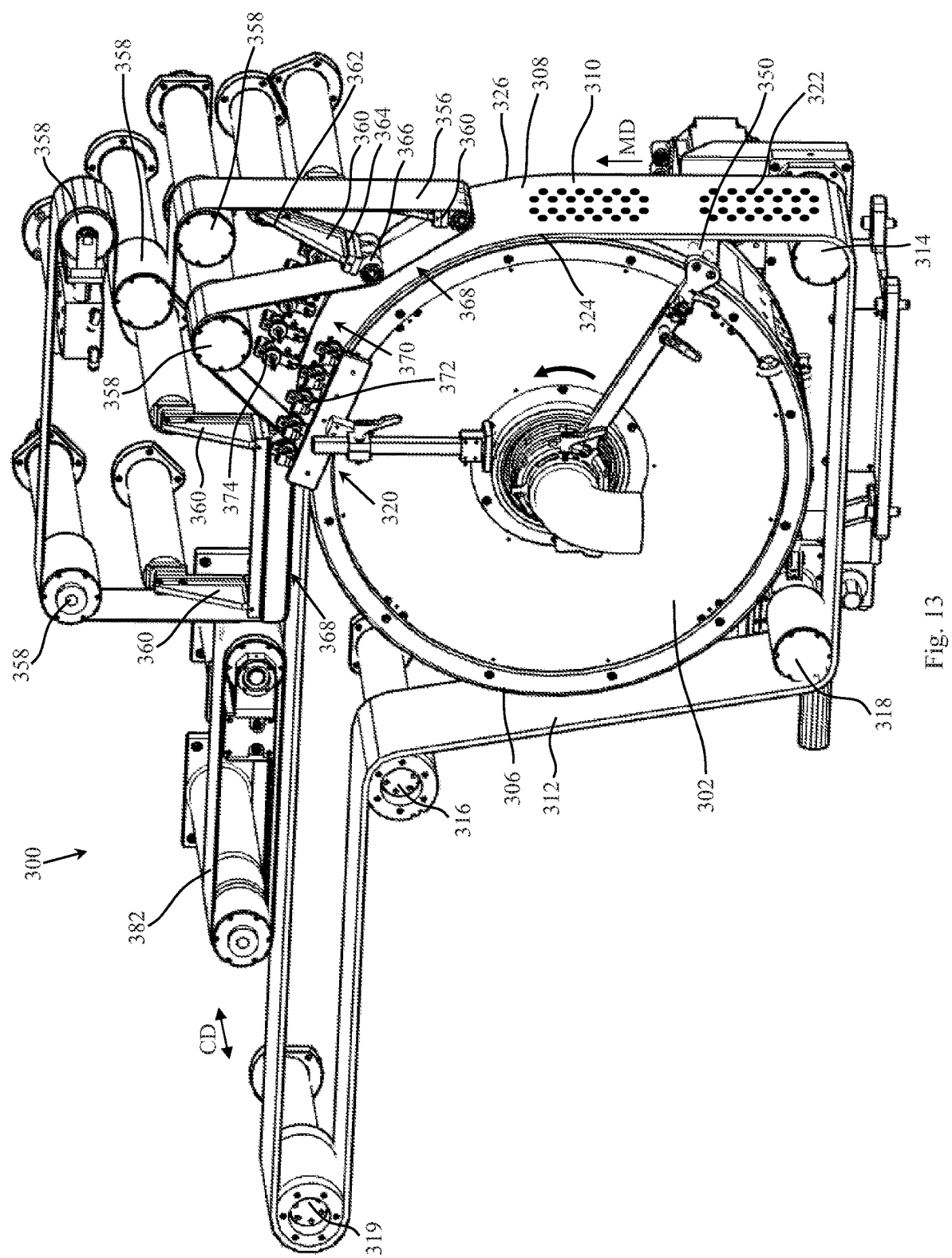
FIG. 13 is a schematic, perspective view of a folding apparatus in accordance with one non-limiting embodiment of the present disclosure.

In some embodiments, as illustrated in FIGS. 9, 10A, and 13, a second carrier member 356 may be used to aid in maintaining the position of the partially folded pant 101 against the carrier member 308 and/or the outer circumferential drum surface 306. The second carrier member 356 may be disposed about a portion of one or more guide rollers 358 and one or more guide arms 360. Each guide arm 360 may include a proximal end portion 362 and a distal end portion 364, opposite the proximal end portion 362. The proximal end portion 362 of the guide arm 360 may be fixed or adjustable and is joined to a fixed member. The distal end portion 364 of the guide arm 360 may include one or more rollers 366 configured to engage the second carrier member 356. Each roller may rotate about an axis of rotation as the second carrier member 356 traverses in the machine direction MD. The second carrier member 356 may be configured such that as the partially folded pant 101 traverses in the machine direction MD, the second carrier member 356 may include portions where the second carrier member 356 is in contact with a surface of the partially folded pant 101 and portions where the second carrier member 356 does not contact the partially folded pant 101. As illustrated in FIG. 13, the second carrier member 356 includes a contact portion 368 prior to the partially folded pant 101 advancing to the folding assembly 320 and upon the partially folded pant 101 leaving the folding assembly 320. Thus, the second carrier member 356 may include a noncontact portion 370 as the partially folded pant 101 is advanced through the folding assembly 320. The second carrier member 356 may be configured to engage the chassis 102 and the central region of the first belt 106c and the second belt 108c. By engaging only the chassis 102 and the central region of the belt, the first end regions 106a, 108a and the second end regions 106b, 108b of the first and second belts 106, 108 may be free to move as the partially folded pant 101 traverses on the drum 302 about the central longitudinal drum axis 304.

Figure 12B:
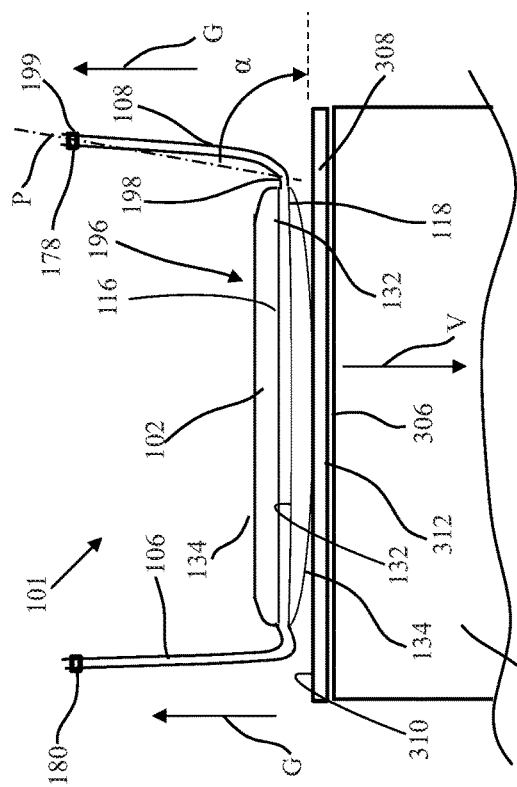
FIG. 12B is a schematic, sectional view of a partially folded diaper pant positioned on a carrier member in accordance with one non-limiting embodiment of the present disclosure.

In some embodiments, as illustrated in FIG. 13, the folding assembly 320 may include a first group of fluid nozzles 372 and a second group of fluid nozzles 374. The first group of fluid nozzles 372 may be positioned adjacent the first carrier edge 324 of the carrier member 308 and/or the second edge portion 342 of the outer circumferential drum surface 306. The second group of fluid nozzles 374 may be positioned opposite the first group of fluid nozzles in the cross direction CD. The second group of fluid nozzles 374 may be positioned adjacent the second carrier edge 326 of the carrier member 308 and/or the first edge portion 340 of the outer circumferential drum surface 306. The first group of fluid nozzles 372 may include one or more nozzles. Each nozzle may be configured to release fluid, such as ambient air. Each fluid nozzle may be directed at a portion of the partially folded pant 101. More specifically, each fluid nozzle may emit fluid such that a first fluid stream engages the first end region 106a, 108a of the first and second elastic belts. As illustrated in FIG. 12B, the fluid exerts a fluid pressure FP against the first end region 106a, 108a of the first and second belts 106, 108. The fluid pressure causes the first end region 106a, 108a to be pushed or guided in the direction indicated by arrow P1. Stated another way, the fluid pressure causes the first end region 106a, 108a to be pushed or guided toward the central body portion 196, which includes the chassis 102 and/or the central region 106c, 108c of the first and second belts 106, 108.

Similarly, the second group of fluid nozzles 374 may include one or more nozzles. Each nozzle may be configured to release fluid, such as ambient air. Each fluid nozzle may be directed at a portion of the partially folded pant 101. More specifically, each fluid nozzle may emit fluid such that a second fluid stream engages the second end region 106b, 108b of the first and second elastic belts. As illustrated in FIG. 12B, the fluid exerts a fluid pressure FP against the second end region 106b, 108b of the first and second belts 106, 108. The fluid pressure causes the second end region 106b, 108b to be pushed or guided in the direction indicated by arrow P2. Stated another way, the fluid pressure causes the second end region 106a, 108a to be pushed or guided toward the central body portion 196, which includes the chassis 102 and/or the central region 106c, 108c of the first and second belts 106, 108.

Figure 12C:
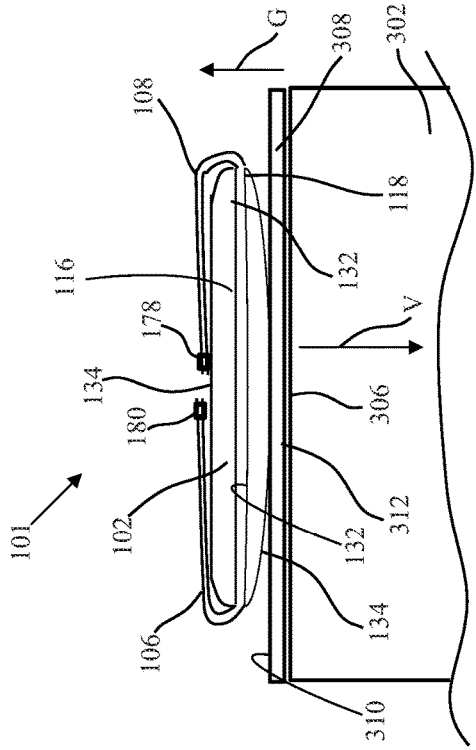
FIG. 12C is a schematic, sectional view of a folded diaper pant positioned on a carrier member in accordance with one non-limiting embodiment of the present disclosure.

The fluid pressure FP generated by a fluid stream from each of the first group of fluid nozzles 372 and the second group of fluid nozzles 374 engages the end regions of the belt resulting in folding the end regions of the first and second belts. Depending on the length of the end regions of the belts, the end regions may be folded such that the second end regions 106b, 108b overlaps the first end regions 106a, 108a and the second side seam 180 may overlap the first side seam 178, as illustrated in FIGS. 12C and 14A. More specifically, the second end regions 106b, 108b may be disposed on the chassis 102 and/or the central region 106c, 108c of one of the first and second belts 106, 108. Further, the first side seam 178 may be disposed on the chassis 102 and/or the central region 106c, 108c of one of the first and second belts 106, 108. A portion of the second end region 106b, 108b may be disposed on the chassis 102 and/or the central region 106c, 108c of one of the first and second belts 106, 108 and another portion of the second end region 106b, 108b may be disposed on the second end region of one of the first and second belts 106, 108. It is also to be appreciated that the end regions may be folded such that the first end regions 106a, 108a overlaps the second end regions 106b, 108b and the first side seam 178 180 overlaps the second side seam.

The fluid nozzles may be controlled such that the end regions are folded in the desired configuration. For example, the fluid nozzles may emit fluid in a sequential manner as the partially folded pant 101 traverses in the machine direction MD. In another example, the fluid nozzles may be controlled such that certain fluid nozzles emit fluid while other fluid nozzles remain off, or fail to emit fluid. It is also to be appreciated that a separation barrier, such as a plate, may be placed between the first fluid stream and the second fluid stream so that the first and second fluid streams do not interfere with one another during the folding process. It is also to be appreciated that the control of the fluid nozzles may be based on, for example, the position of the absorbent article, the manufacturing line speed, or the size of the absorbent article, which may be determined based on a signal generated upstream of the folding apparatus.

Figure 12D:
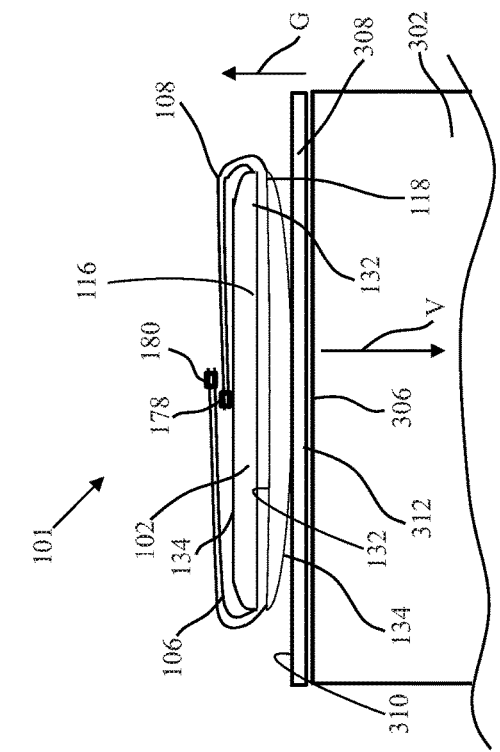
FIG. 12D is a schematic, sectional view of a folded diaper pant positioned on a carrier member in accordance with one non-limiting embodiment of the present disclosure.
Figure 14B:
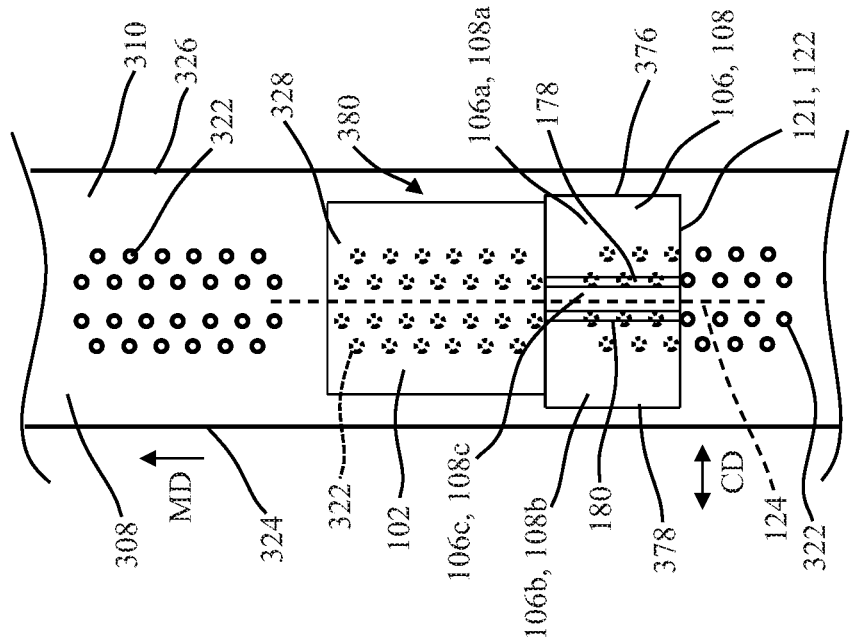
FIG. 14B is a schematic, top view a portion of a carrier member with an absorbent article disposed thereon in accordance with one non-limiting embodiment of the present disclosure.
Figure 14A:
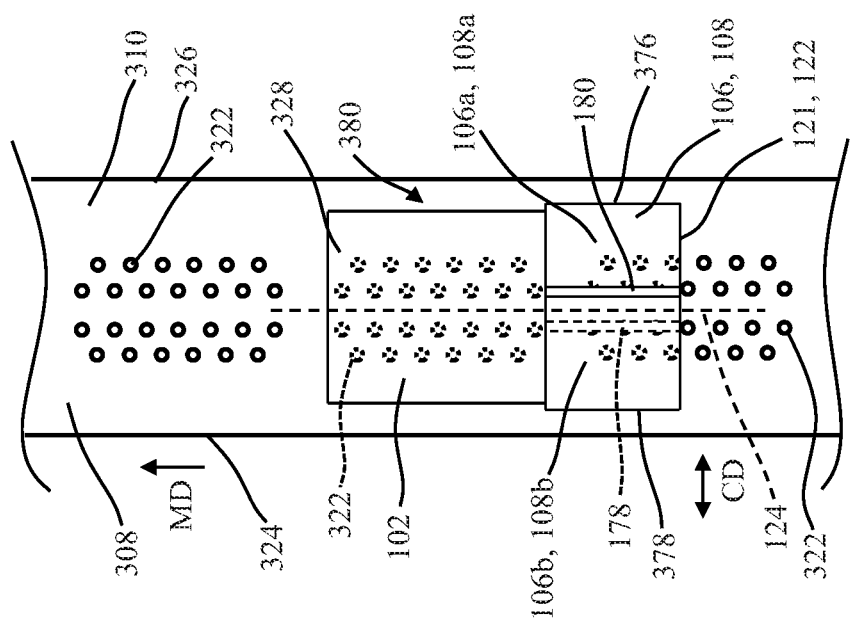
FIG. 14A is a schematic, top view a portion of a carrier member with an absorbent article disposed thereon in accordance with one non-limiting embodiment of the present disclosure.

In some embodiments, the length of the end regions may be such that when the belts are folded, the first end regions 106a, 108a do not overlap the second end regions 106b, 108b, as illustrated in FIGS. 12D and 14B. Thus, each of the first end regions 106a, 108b and the second end regions 106b, 108b may be disposed on the chassis 102 and/or the central region 106c, 108c of one of the first and second belts 106, 108.

Once the first end region of the first and second belts and the second end region of the first and second belts are folded, as previously discussed, a first fold line 376 extending parallel to the longitudinal axis 124 and a second fold line 378 extending parallel to the longitudinal axis 124 are formed. A partially folded pant 101 including folded first end regions and second end regions of the first and second belts may be referred to herein as a folded pant 380, as illustrated in FIGS. 14A and 14B.

Referring to FIGS. 12E and 12F, the partially folded pant 101 may also be folded such that the first side seam 178, the second side seam 180, at least a portion of the first elastic belt 106, and at least a portion of the second elastic belt 108 are positioned between the first waist region 116 and the second waist region 118. More specifically, as the folding apparatus 300 rotates about the central longitudinal axis of rotation 304, centrifugal and/or gravitational forces may pull the second waist region 118 of the partially folded diaper pant 101 in a first direction A, away from the outer circumferential drum surface 306, as illustrated, for example, in FIG. 12E. Vacuum may be used to hold a portion of the partially folded pant 101 against the outer circumferential drum surface 306. The second carrier member 356 may allow the waist region of the diaper pant farthest from the outer circumferential drum surface 306 to extend away from the outer circumferential drum surface 306 while the other portion of the waist region is held against the outer circumferential drum surface 306 as the partially folded pant 101 rotates. In some embodiments, the second carrier member 356 may be configured to converge towards the outer circumferential drum surface 306 such that the inner surface 132 of the second waist region 118 moves in a second direction, B, toward the first waist region 116 as the folded diaper pant 101 advances. It is to be appreciated that vacuum may be used to control the movement of the second waist region 118. For examples, in some embodiments, a vacuum force V may be supplied by the folding apparatus 300 that causes the waist region of the partially folded pant 101 to move toward the outer circumferential drum surface 306, which is in the direction illustrated by arrow B in FIG. 12F. The vacuum force may be varied as the partially folded pant 101 traverses about the folding apparatus 300. The vacuum force may increase as the partially folded pant 101 traverses such that the waist regions converge. As the second waist region 118 moves in the direction, B, toward the first waist region 116, the first and second side seams 178, 180 are held tucked into the chassis 102 of the folded diaper pant 101.

Fluid nozzles, side seam tuckers, such as rotating blades, or any other tucking apparatus discussed herein may be used to tuck the first and second side seams 178 and 180 as the second waist region 118 is positioned away from the first waist region 116.

Referring to FIG. 13, the folded pant 380 may advance from the folding assembly 320 to a second contact portion 368 of the second carrier member 356. The second carrier member 356 may aid in maintaining the folds in the folded pant 380. The folded pant 380 may transfer from the second carrier member 356 to a third carrier member 382, which also aids in maintaining the fold of the folded pant 380 and may allow additional processes to be performed on the folded pant 380. The folded pant 380 may advance to other additional processes such as additional folding processes and packaging processes. It is also to be appreciated that the carrier member 308 may create a closed loop such that the carrier member 308 traverses about a fourth guide roller 319 as the carrier member 308 advances toward the drum 302 to transfer another absorbent article.

The folding assembly 320 may include a number of different devices that can be used to fold the partially folded pant 101. For example, the folding assembly 320 may include one or more groups of nozzles, which are configured to release a fluid stream, one or more plows, such as planar plows and arced plows, and/or one or more folding devices. In some embodiments, the folding assembly 320 may be positioned adjacent the outer circumferential drum surface 306. In some other embodiments, the folding assembly 320 may include a portion positioned adjacent the outer circumferential drum surface 306 and a portion that is downstream of the drum 302 in the machine direction MD. Further, in yet some other embodiments, the folding assembly 320 may be positioned downstream of the drum 302 in the machine direction MD. The rotation of the drum 302 about the central longitudinal drum axis 304 may provide sufficient centrifugal and/or gravitational forces on the partially folded pant 101 so that the partially folded pant 101 may undergo folding by the folding assembly 320, such as previously discussed. The following is a discussion of folding assemblies 320 that may take advantage of the centrifugal and/or gravitational forces which act on the partially folded pant 101 to form a folded pant 380.

Figure 15:
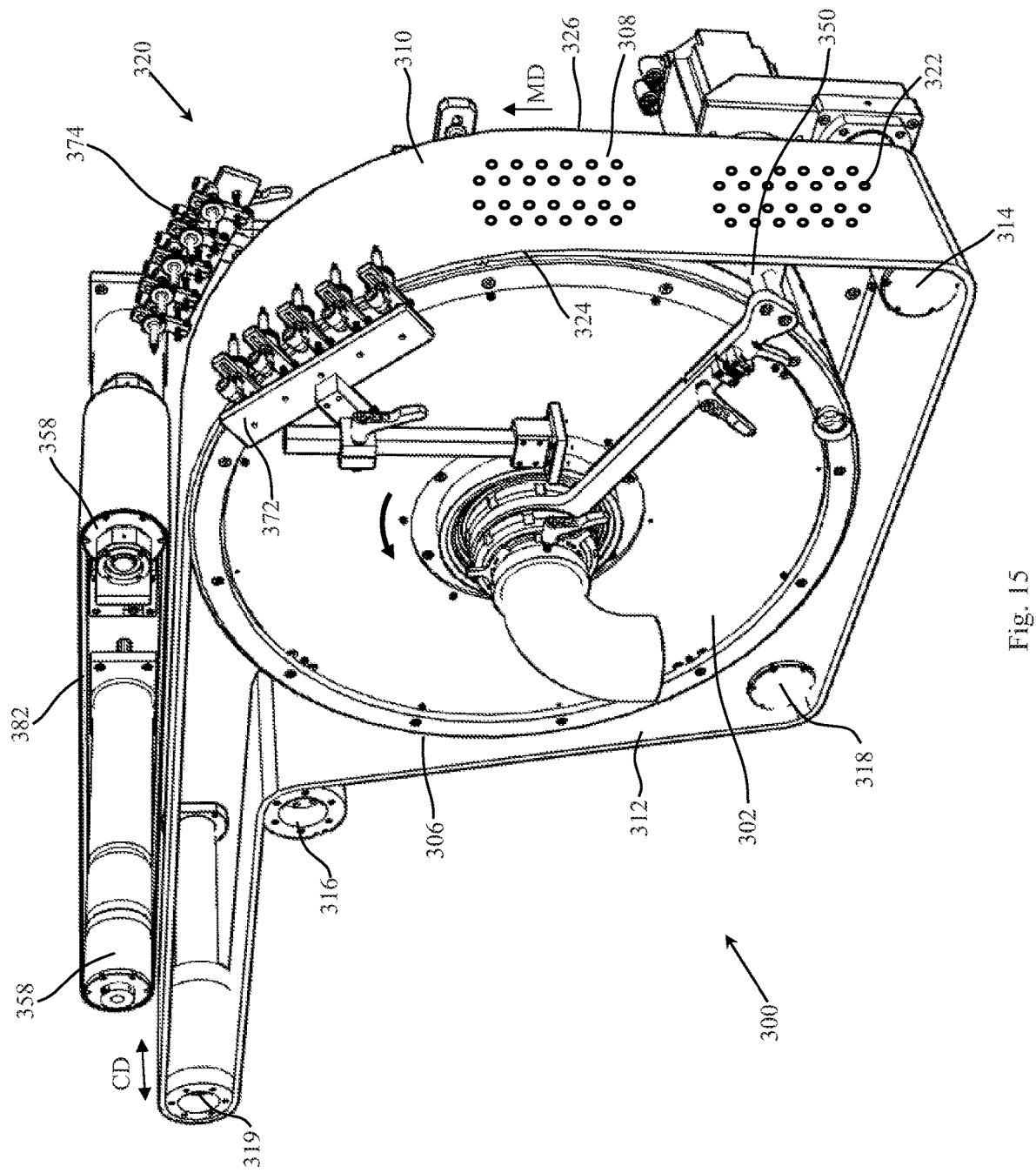
FIG. 15 is a schematic, perspective view of a folding apparatus in accordance with one non-limiting embodiment of the present disclosure.

Referring to FIG. 15, the folding assembly 320 may include a first group of fluid nozzles 372 and a second group of fluid nozzles 374. The first group of fluid nozzles 372 may be positioned adjacent the first carrier edge 324 of the carrier member 308 and/or the second edge portion 342 of the outer circumferential drum surface 306. A portion of the second group of fluid nozzles 374 may be positioned opposite a portion of the first group of fluid nozzles in the cross direction CD. The second group of fluid nozzles 374 may be positioned adjacent the second carrier edge 326 of the carrier member 308 and/or the first edge portion 340 of the outer circumferential drum surface 306. Further, the first group of fluid nozzles 372 may be offset from the second group of fluid nozzles 374 in the machine direction MD. The first group of fluid nozzles 372 and the second group of fluid nozzles 374 may each include one or more nozzles. Each nozzle may be configured to release fluid, such as ambient air. Each fluid nozzle may be directed at a portion of the partially folded pant 101. The offset arrangement of the first group of fluid nozzles 372 and the second group of fluid nozzles 374 may aid in folding the partially folded pant 101. For example, for those partially folded pants 101 including belts that overlap when folded, the offset of the fluid nozzles may allow the first end region of the belt to be folded without conflicting with the second edge region of the belt. Further, the offset arrangement may be another way prevent the fluid paths of the two groups of nozzles from interfering with one another during the folding process.

Figure 16:
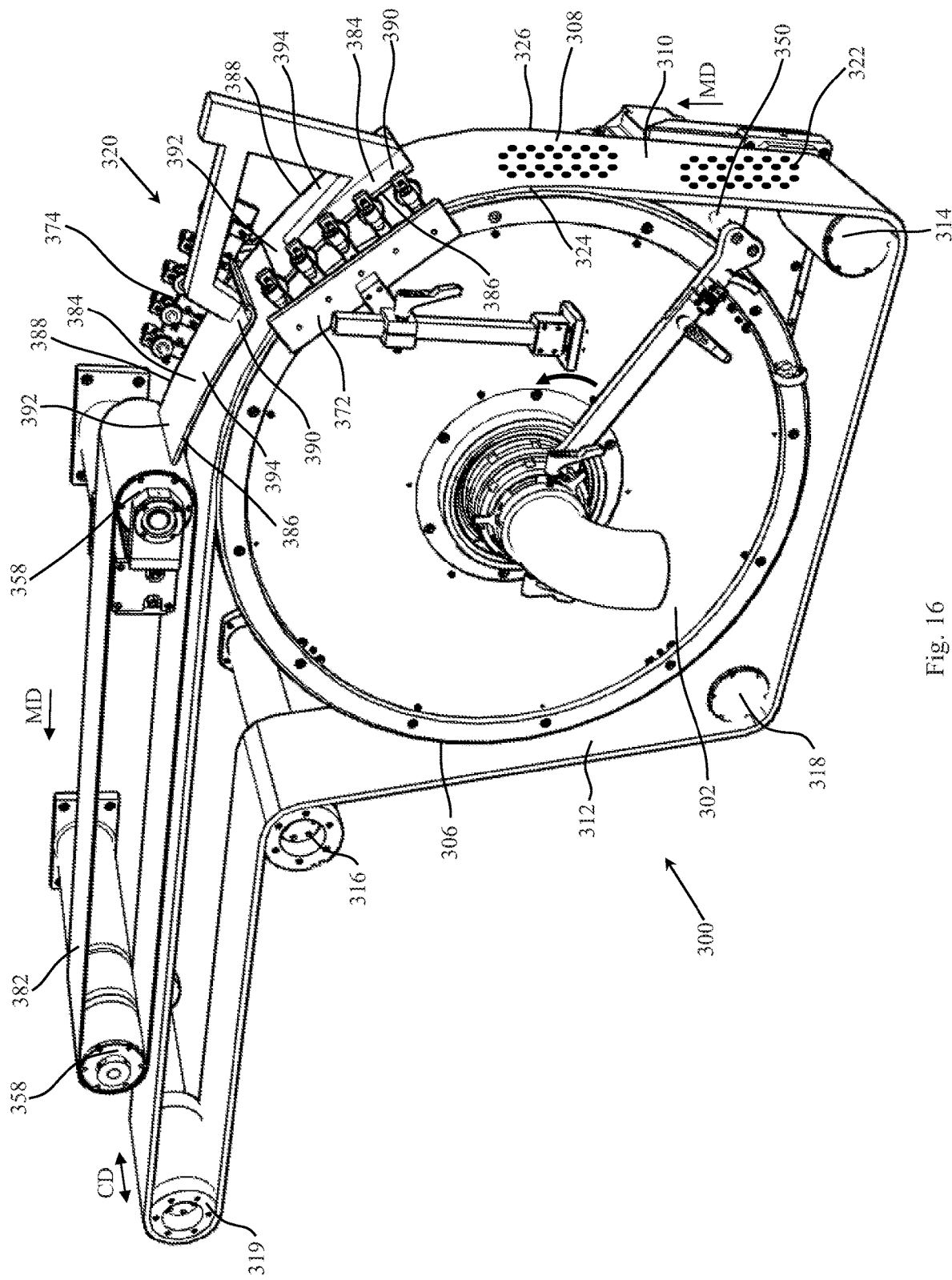
FIG. 16 is a schematic, perspective view of a folding apparatus in accordance with one non-limiting embodiment of the present disclosure.

In some embodiments, the folding assembly 320 may also include one or more folding plates 384, as illustrated in FIG. 16. The folding plate 384 may be positioned adjacent the outer circumferential drum surface 306 and/or the carrier member 308. The folding plate 384 may be a substantially rigid member that aids in folding the partially folded pant 101. The folding plate 384 may include a first surface in facing relationship with the outer circumferential drum surface 306 and/or the carrier member 308. The first surface may extend over a portion of the outer circumferential drum surface 306 and may be shaped similar to the outer circumferential drum surface 306. The folding plate 384 may also include a first folding edge 386 and a second folding edge 388, opposite the first folding edge 386 in the cross direction CD. The first folding edge 386 and the second folding edge 388 may each extend in a direction parallel to the machine direction MD. Each folding plate 384 may also include a leading edge portion 390 and a trailing edge portion 392. The leading edge portion 390 may be opposite the trailing edge portion 392 in the machine direction MD. Each of the leading edge portion 390 and the trailing edge portion 392 may extend in a direction parallel to the cross direction CD. The first surface of the folding plate 384 may be configured to engage the chassis 102 and the central region 106c, 108c of one of the first and second belts 106, 108. The first surface may aid in maintaining the position of the partially folded pant 101 against the outer circumferential drum surface 306 and/or the carrier member 308. The folding plate 384 may be configured such that the coefficient of friction between the first surface and the folded absorbent article is relatively low in order to assist or not inhibit the absorbent article in advancing in the machine direction. The coefficient of friction may be lowered by coating the first surface or applying positive pressure, which may be a fluid pressure, through apertures defined by the folding plate.

The folding plate 384 also includes a first folding edge 386 and a second folding edge 388. The first folding edge 386 may be adjacent the first carrier edge 324 and/or the second edge portion 342 of the drum 302. Similarly, the second folding edge 388 may be adjacent the second carrier edge and/or the first edge portion 340 of the drum 302. Each of the first folding edge 386 and the second folding edge 386 may be spaced from the fluid nozzles such that the end regions of the belt have sufficient clearance to extend away from the outer circumferential drum surface 306 and to continue to traverse in the machine direction MD. The first and second folding edges 386, 388 also aid in folding the partially folded pant 101. The first and second folding edge 386, 388 create an edge about which the end region of the belt folds. For example, as the partially folded pant 101 traverses in the machine direction MD, the first and second end regions of the belt extend away from the outer circumferential drum surface 306, as illustrated in FIG. 12A. The chassis 102 advances toward the leading edge portion 390 of the folding plate 384. The chassis 102 advances adjacent the first surface of the folding plate 384. The first end region of the belt is positioned between the first group of fluid nozzles 372 and the first folding edge 386. As the fluid nozzles of the first group of fluid nozzles 372 emit fluid, the first end region is pushed or guided onto a second surface 394 of the folding plate 384. The first end region wraps around a portion of the first folding edge 386, which aids in forming a fold line that extends parallel to the machine direction MD. As the partially folded pant 101 exits the trailing edge portion 392 of the folding plate 384, the first end region advances from the second surface 394 and is disposed on the chassis and/or central region of the belt. Similarly, the second folding edge 388 may aid in guiding the second end region as the partially folded pant 101 continues to traverse about the central longitudinal drum axis 304 and in forming a second fold line.

Further, the leading edge portion 390 of the subsequent folding plate 384 may be shaped such that the first end region, the chassis, and the central region of the belt are positioned between the first surface of the second folding plate 384 and the outer circumferential drum surface 306 and/or the carrier member 308. As illustrated in FIG. 16, the leading edge portion 390 may be curved in a direction away from the outer circumferential drum surface 306 to aid in transitioning the first region, chassis, and central region of the belt from the first folding plate to the first surface of the second folding plate 384. The second end region of the belt, while being subject to the centrifugal and/or gravitational forces, is positioned between the second group of fluid nozzles 374 and the second folding edge 388. As the fluid nozzles of the second group of fluid nozzles 374 emit fluid, the second end region is pushed or guided onto a second surface 394 of the folding plate 384. The second end region wraps around a portion of the second folding edge 388, which aids in forming a second fold line. As the partially folded pant 101 exits the trailing edge portion 392 of the folding plate 384, the second edge region is disposed on the chassis and/or central region of the belt or a portion of the first edge region of the belt forming a folded pant 380. The folded pant 380 may advance to a third carrier member 382. The folded pant 380 may be positioned between the carrier member 308 and the third carrier member 382 as the folded pant 380 advances in the machine direction MD.

It is to be appreciated that one or more folding plates may be used to fold the partially folded pant 101. Similarly, one or more groups of fluid nozzles may be used to fold the partially folded pant 101.

Figure 17A:
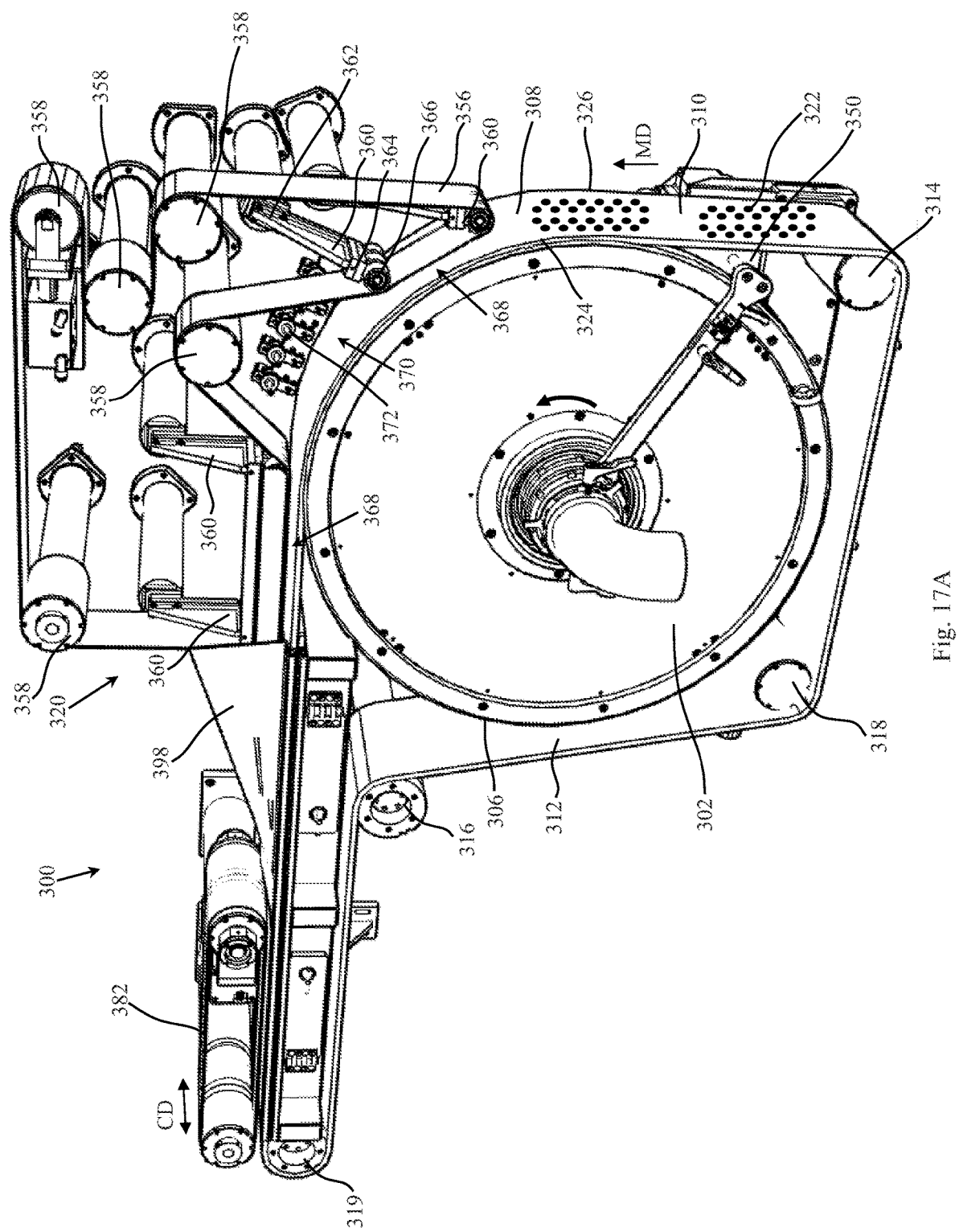
FIG. 17A is a schematic, perspective view of a folding apparatus in accordance with one non-limiting embodiment of the present disclosure.
Figure 17B:
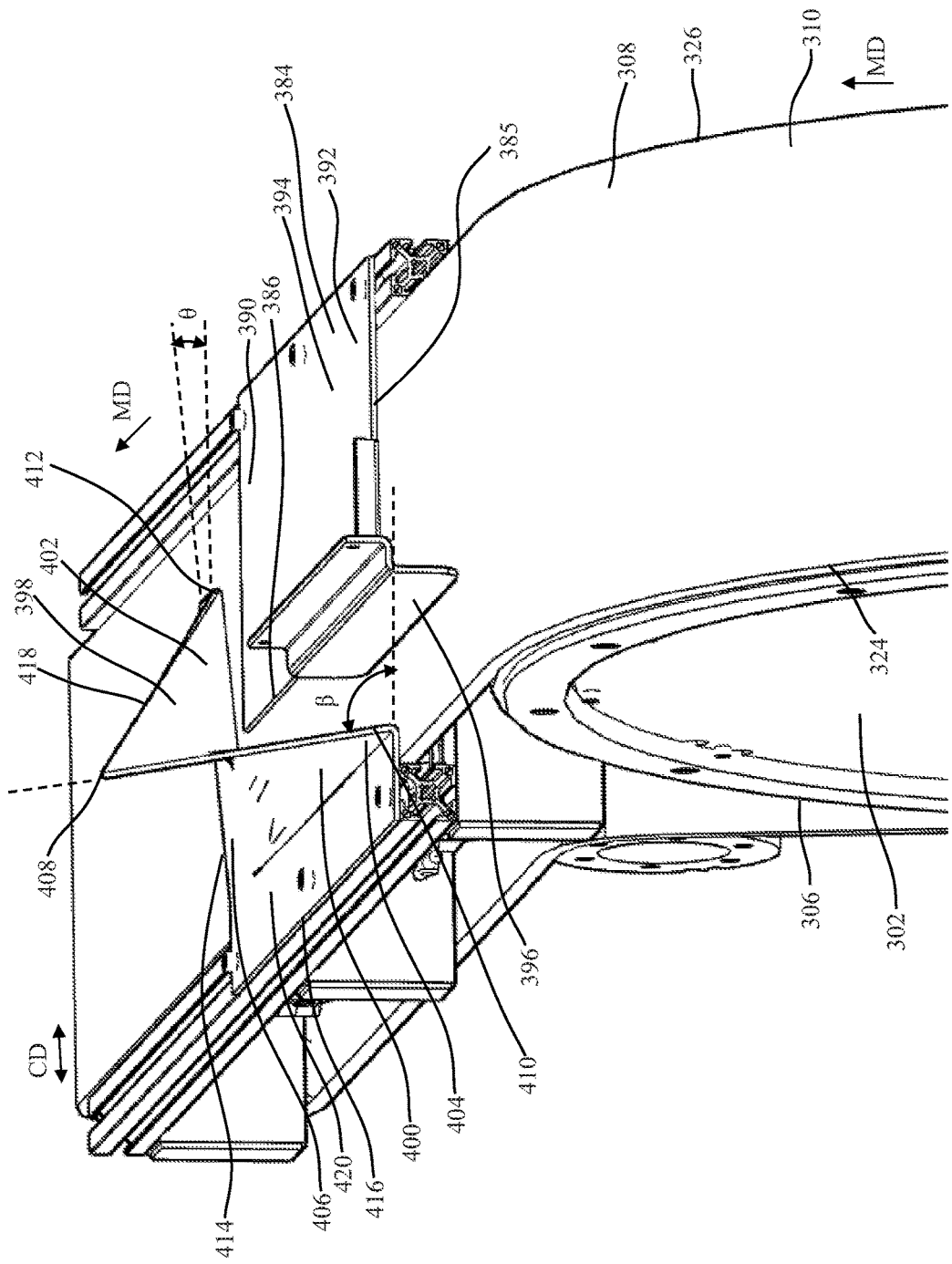
FIG. 17B is a schematic, perspective view of a first planar plow and a folding plate positioned adjacent the carrier member in accordance with one non-limiting embodiment of the present disclosure.

FIGS. 17A and 17B illustrate another folding assembly 320. In some embodiments, the folding assembly 320 may include a first group of fluid nozzles 372 and a first planar plow 398. As previously discussed, a second carrier member 356 may be used to aid in maintaining the position of the absorbent article. However, it is to be appreciated that the second carrier member 356 is not necessary. As illustrated in FIG. 17A, a portion of the partially folded pant 101 may engage the second carrier member 356. The second carrier member 356 engages the chassis and/or central region of the belt. The second carrier member 356 does not interfere with the first and second end regions of the belt. The first and second end regions of the belt move in a direction away from the outer circumferential drum surface 306 due to the centrifugal and/or gravitational forces generated, in part, by the traversing drum 302. Each of the first end region and the second end region extend in a direction G, as illustrated in FIG. 12A. The partially folded pant 101 continues to traverse about the central longitudinal drum axis 304 and may advance to a noncontact portion 370 of the second carrier member 356. The first group of fluid nozzles 372 may be positioned in the noncontact portion 370 and adjacent to the outer circumferential drum surface 306. The first group of fluid nozzles 372 may be configured to fold one of the first end region of the belt or the second end region of the belt. Thus, the fluid nozzles of the first group of fluid nozzles 372 may emit fluid and engage either the first end region of the belt or the second end region of the belt. The fluid may push or guide the first end region of the belt or the second end region of the belt against the central body portion 196, which includes the chassis 102 and/or the central region of the belt. The partially folded pant 101 advances to another contact portion 368 of the second carrier member 356. The partially folded pant 101 includes one end region that is disposed on the chassis and/or the central region of the belt and the other end region extending in a direction away from the outer circumferential drum surface 306. The second carrier member 356 engages the chassis, central region, and one of the end regions. The second carrier member 356 aids in maintaining the position of the end region on the chassis and/or the central region of the belt.

Referring to FIG. 17B, the partially folded pant 101 advances from the second carrier member 356 to a folding plate 384. The folding plate 384 may be a substantially rigid member, such as previously discussed. The folding plate 384 may include a first surface 385 in facing relationship with the outer circumferential drum surface 306 and/or the carrier member 308 and a second surface 394 opposite the first surface 385. The folding plate 384 may also include a first folding edge 386 extending in a direction parallel to the machine direction MD and a folding guide member 396 joined to a portion of the folding plate 384 adjacent the first folding edge 386. The partially folded pant 101 may transfer from the second carrier member 356 to the folding plate 384 such that the chassis 102, central region of the belt, and the folded end region are positioned adjacent to the first surface 385 of the folding plate 384. The other end region, or the end region that has not undergone folding, may be positioned between the folding guide member 396 and a first planar plow 398. The other end region may be the first end region or the second end region of the belt. The end region passes through a gap formed between the folding guide member 396 and the first planar plow 398.

The first planar plow 398 includes an outer surface 400 and an inner surface 402, opposite the outer surface 400. The inner surface 402 of the first planar plow 398 may be in facing relationship with the end region of the belt and may be configured to engage the end region of the belt. The first planar plow 398 may include a first end portion 404 and a second end portion 406 opposite the first end portion 404 in the machine direction MD. The partially folded pant 101 advances from the first end portion 404 to the second end portion 406 in the machine direction MD. The first planar plow 398 may also include a first side plow edge 416 and a second side plow edge 418 opposite the first side plow edge 416 in the cross direction. The first side plow edge 416 may extend in the machine direction MD and be positioned adjacent the first carrier edge 326. The second side plow edge 418 may be positioned over a portion of the carrier member 308 such that the second side plow edge 418 may be configured to guide a portion of the end region of the belt.

More specifically, the first end portion 404 includes a plow peak region 408 and a first end plow edge 410. The plow peak region 408 is the region of the first planar plow 398 that is farthest from the outer circumferential drum surface 306 in a direction perpendicular from the outer circumferential drum surface 306 and adjacent the first plow edge 410. The plow peak region 408 may form a portion of the second side plow edge 418. The first plow end edge 410 extends in a direction away from the outer circumferential drum surface 306. The first end plow edge 410 may form a first plow edge angle β with a plane that is parallel to the outer circumferential drum surface 306. The first plow edge angle β may be from about 30 degrees to about 160 degrees and/or from about 70 degrees to about 110 degrees, including all 0.1 increments therebetween. The first end plow edge 410 may be positioned with respect to the outer circumferential surface 306 and the folding guide member 396 such that the end region of belt is positioned between the first end plow edge 410 and the folding guide member 396. Further, the first end plow edge 410 directs the end region of the belt to the inner surface 400 of the first planar plow 398.

Opposite the first end portion 404 is the second end portion 406 of the first planar plow 398. The second end portion 404 may include a plow landing region 412 and a second end plow edge 414. The plow landing region 412 of the first planar plow 398 is the region along the second side plow edge 418 that is closest to the outer circumferential drum surface 306 in a direction perpendicular from the outer circumferential drum surface 306 and adjacent the second end plow edge 414. There may be a gap between the plow landing region 412 and the carrier member 308 and/or the outer circumferential drum surface 306 to allow clearance for the passing of the absorbent article. The second plow end edge 414 may gradually extend in a direction away from the outer circumferential drum surface 306 to allow for passage of the absorbent article and clearance to push or guide the end region of the belt onto the chassis and/or the central region of the belt. The second end plow edge 414 may form a second plow edge angle θ with a plane that is parallel to the outer circumferential drum surface 306. The second plow edge angle θ may be from about −45 degrees to about 60 degrees and/or from about −30 degrees to about 45 degrees and/or from about −10 to about 20 degrees, including all 0.1 increments therebetween. The second end plow edge 414 may be positioned with respect to the outer circumferential surface 306 and the folding plate 384 such that the end region of belt may be disposed on a portion of the chassis and/or central belt region or the end region that had been previously disposed on the chassis and/or central belt region.

The second side plow edge 418 may extend from the plow peak region 408 to the plow landing region 412. Thus, the second side plow edge 418 forms an arcuate or sloping shape that generally extends in the machine direction MD. Further, as the plow extends in the cross direction from the second side plow edge 418 toward the first side plow edge 416, the plow is shaped in an arcuate or sloping path until the planar plow forms a side end plow portion 420 that may be substantially planar to the surface of the carrier member 308.

The sloping or arcuate shape of the first planar plow 398 directs the end region of the belt into a folded configuration such that the end region is disposed on the chassis and/or central region of the belt or at least a portion of the opposite end region of the belt. The end region of the belt may follow the inner surface 402 of the first planar plow 398. The inner surface 402 guides or pushes the end region of the belt toward the chassis 102 of the absorbent article. At the position where the end region engages the plow landing region 412, the end region may be disposed on the chassis and/or the central region of the belt and/or at least a portion of the opposite end region of the belt. Once each end region is disposed on the chassis and/or the central region of the belt, and/or the opposing end region of the belt, the folded pant 380 may continue to advance to subsequent processes.

Figure 18:
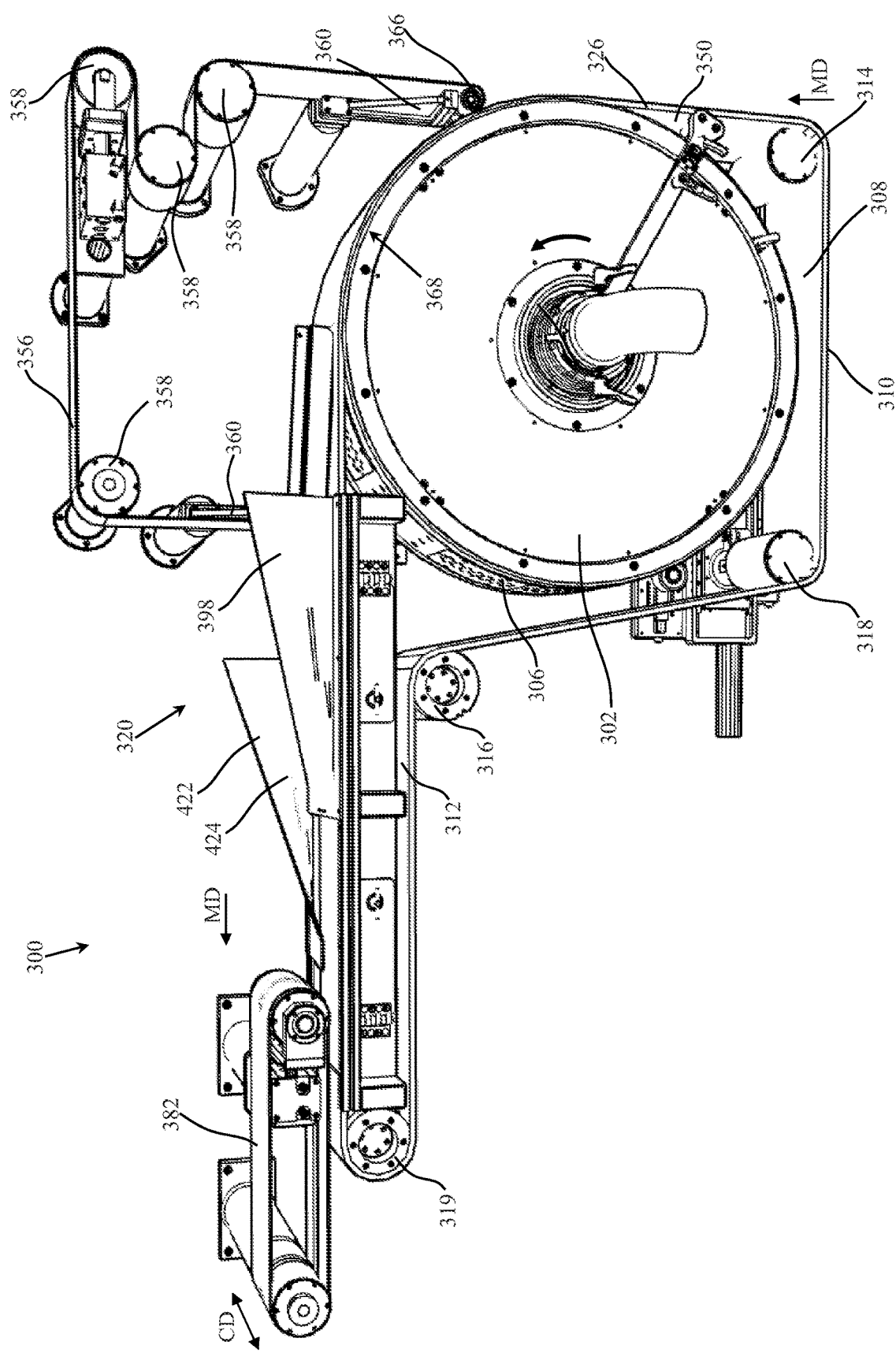
FIG. 18 is a schematic, side view of a folding apparatus in accordance with one non-limiting embodiment of the present disclosure.

In some other embodiments, the folding assembly 320 may be positioned such that folding of the partially folded pant 101 occurs after the partially folded pant 101 has been removed from the drum 302, as illustrated in FIG. 18. The folding assembly 320 may include a first planar plow 398 and a second planar plow 422. The first planar plow 398 may be offset from the second planar plow 422 in the machine direction MD. This configuration allows the folding of the two end regions not to interfere with one another and, in some embodiments, for one end region to be folded onto the other end region. The first planar plow 398 may overlap a portion of the second planar plow 422 in the machine direction MD, as illustrated in FIG. 18. The first planar plow 398 may be positioned adjacent the second carrier edge 326 and/or the second edge portion 342 of the outer circumferential surface 306. The second planar plow 422 may be positioned opposite a portion of the first planar plow 398 in the cross direction CD. The second planar plow 422 may be configured similar to the first planar plow 398, as described with respect to FIG. 17B. The second planar plow 422 may include an inner surface 424 and the first planar plow 398 may include an inner surface 402. The inner surface 424 of the second planar plow 422 may be in facing relationship with at least a portion of the inner surface 402 of the first planar plow 398. As the partially folded pant 101 advances from the outer circumferential drum surface 306, the second end region 106b, 108b of the belt and the first end region 106a, 108a of the belt may extend in a direction away from the carrier member 308. The inner surface 402 of the first planar plow 398 may be configured to engage the second end region 106b, 108b of the partially folded pant 101. The inner surface 402 of the first planar plow 398 guides the second end region 106b, 108b of the belt toward the chassis 102 as the partially folded pant advances in the machine direction. As the second end region 106, 108b engages the first planar plow 398, the inner surface 424 of the second planar plow 422 may be configured to engage the first end region 106a, 108a of the partially folded pant 101. The inner surface 424 of the second planar plow 422 guides the first end region 106a, 108a of the belt toward the chassis 102 and/or the central region of the belt, and/or the second end region of the belt. Once the partially folded pant 101 undergoes folding by the first planar plow 398 and the second planar plow 422, a folded pant 380 is formed. The folded pant 380 may advance to the third carrier member 382, positioned adjacent the second planar plow 422, and to subsequent processes.

Figure 19A:
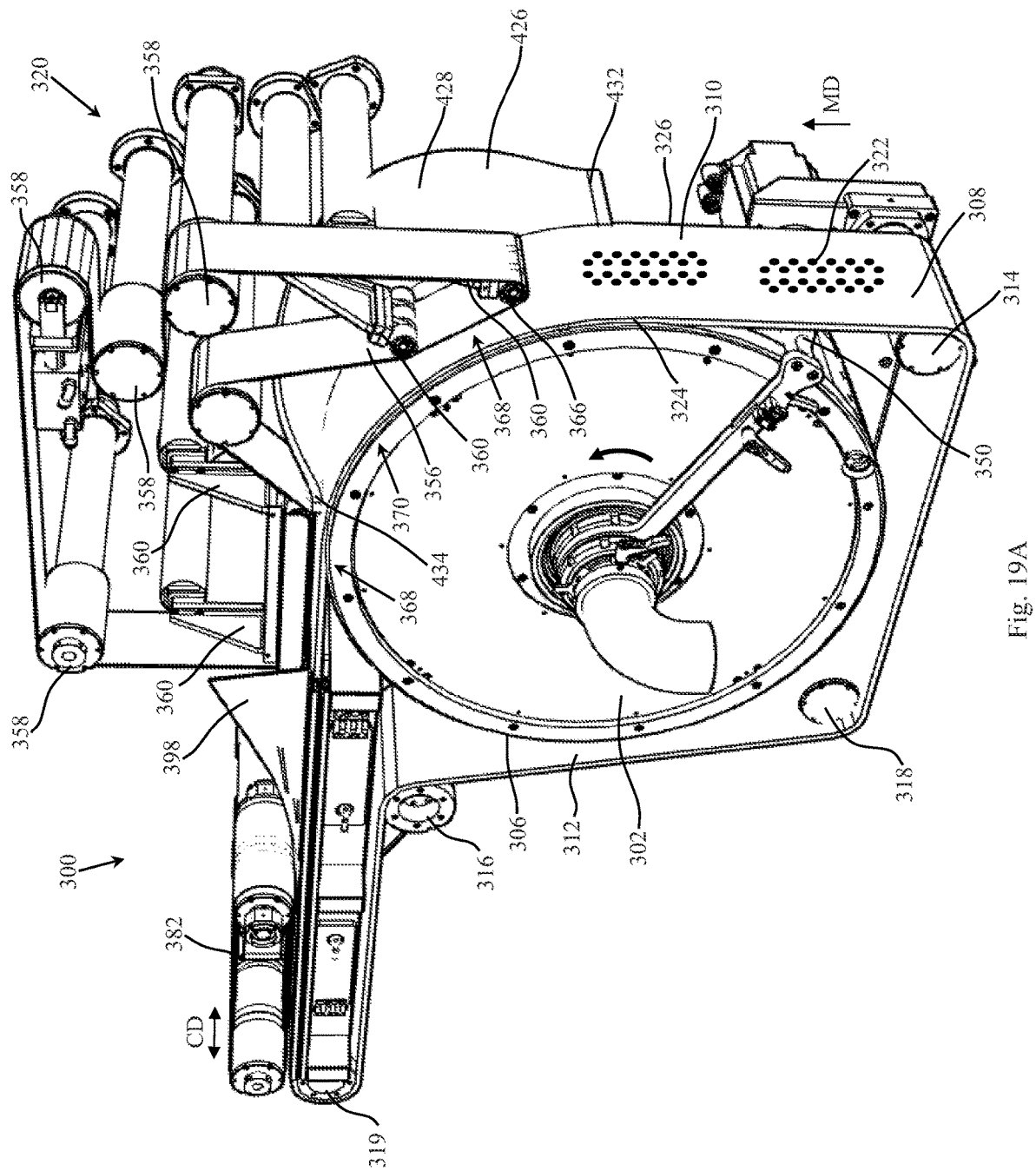
FIG. 19A is a schematic, perspective view of a folding apparatus in accordance with one non-limiting embodiment of the present disclosure.

In some embodiments, the folding assembly 320 may include a first arced plow 426 and a first planar plow 398, as illustrated in FIG. 19A. As previously discussed, a second carrier member 356 may be used to aid in maintaining the position of the absorbent article. However, it is to be appreciated that the second carrier member 356 is not necessary. The absorbent article may be held against the outer circumferential surface 306 and/or the carrier member 308 by a vacuum force generated as fluid is pulled through the one or more apertures defined by the drum 302 and/or the carrier member 308. As illustrated in FIG. 19A, the second carrier member 356 may be configured to engage a portion of the partially folded pant 101. The second carrier member 356 may engage the central body portion 196, which includes the chassis and/or central region of the belt. The second carrier member 356 does not interfere with the first and second end regions of the belt. The first and second end regions of the belt move in a direction away from the outer circumferential drum surface 306 due to the centrifugal and/or gravitational forces generated, in part, by the traversing drum 302. Each of the first end region and the second end region extend in a direction G, as illustrated in FIG. 12A. The first end region 106a, 108a may be folded by the first arced plow 426. The first arced plow 426 extends about a portion of the outer circumferential drum surface 306 and may be positioned adjacent to one of the first carrier edge 324 or the second carrier edge 326. Stated another way, the first arced plow 426 may be positioned adjacent one of the first edge portion 340 of the outer circumferential surface 306 or the second edge portion 342 of the outer circumferential surface 306. In some embodiments, the first arced plow 426 may extend from the contact portion 368 of the second carrier member 356 through the noncontact portion 370 of the second carrier member 356.

Referring to FIGS. 19A-19C, the first arced plow 426 may include an inner arced plow surface 428 and an outer arced plow surface 430. The inner arced plow surface 428 may be configured to engage and guide or push the end region of the belt onto the chassis and/or central region of the belt. The inner arced plow surface 428 may be shaped in any manner such that the end region of the belt may be accepted onto the inner arced plow surface and guided onto a portion of the central body portion 196. More specifically, the first arced plow 426 may include a first end portion 432 and a second end portion 434 opposite the first end portion 432 in the machine direction MD. Thus, the partially folded pant 101 while advancing in the machine direction MD first encounters the first end portion 432 of the first arced plow 426 and subsequently encounters the second end portion 434 of the first arced plow 426. The inner surface 428 of the first end portion 432 of the first arced plow 426 may form a first arced angle δ with the outer circumferential drum surface 306 or the first surface 310 of the carrier member 308, as illustrated in FIGS. 19B-19D. The first arced angle δ may be large enough to accept the partially folded pant 101 and/or to avoid adversely interfering with the transfer apparatus 220 and, more specifically, the transfer members 230, as illustrated in FIG. 9. The first arced angle δ may be an obtuse angle. The first arced angle δ may be from about 45 degrees to about 270 degrees and/or from about 160 degrees to about 220 degrees, including all 0.1 increments therebetween. The first arced plow 426 curves from the first end portion 432 to the second end portion 434. The inner surface 428 of the second end portion 434 may form a second arced angle γ with the outer circumferential drum surface 306 or the first surface 310 of the carrier member 308, as illustrated in FIGS. 19B, 19C, and 19E. The second arced angle γ may be an acute angle. The second arced angle α may be from about −45 degrees to about 60 degrees and/or from about −10 degrees to about 20 degrees, including all 0.1 increments therebetween. Further, there may be a gap between the inner surface 428 and the carrier member 308 and/or the outer circumferential drum surface 306 to provide clearance for the absorbent article traversing in the machine direction MD. The curve of the arced plow 426 causes the end region of the belt to be guided toward or pushed toward to the chassis and/or the central region of the belt. The first arced plow 426 may be any length such that the first arced plow 426 engages the end region while the end region of the belt extends in a direction away from the drum 302 and guides the end region into a fold. Further, the first arced plow 426 may be any height such that the first arced plow 426 controls the end region of the belt while guiding the end region toward the chassis.

Upon exiting the second end portion 434 of the arced plow 434, one of the first end region 106a, 108a or the second end region 106b, 108b of the belt 106, 108 may be disposed on the chassis 102 and/or the central region 106c, 108c, of the belt 106, 108. The partially folded pant 101 may advance to a second contact portion 368 of the second carrier member 356. It is to be appreciated that the second carrier member 356 is not necessary and may be replaced by some other mechanical device or vacuum force to hold the chassis 102, central region of the belt, and one of the first end region or the second end region of the belt in position. As illustrated in FIG. 19A, the partially folded pant 101 is advanced to the contacted portion 368 of the second carrier member 356. The second end region 106b, 108b may remain unaffected by the second carrier member 356 and the second end region of the belt may extend away from the carrier member 308 or the outer circumferential drum surface 306. The partially folded pant 101 may then advance to a first planar plow 398, such as previously discussed. The first planar plow 398 may engage the second end region 106b, 108b of the belt 106, 108 and push or guide the second end region toward the chassis 102. The second end region 106b, 108b of the belt may be disposed on a portion of the chassis 102, the central region 106c, 108c of the belt 106, 108, or the first end region 106a, 108a of the belt 106, 108 forming a folded pant 380. The folded pant 380 may advance to a third carrier member 382 and/or additional processes.

Figure 20:
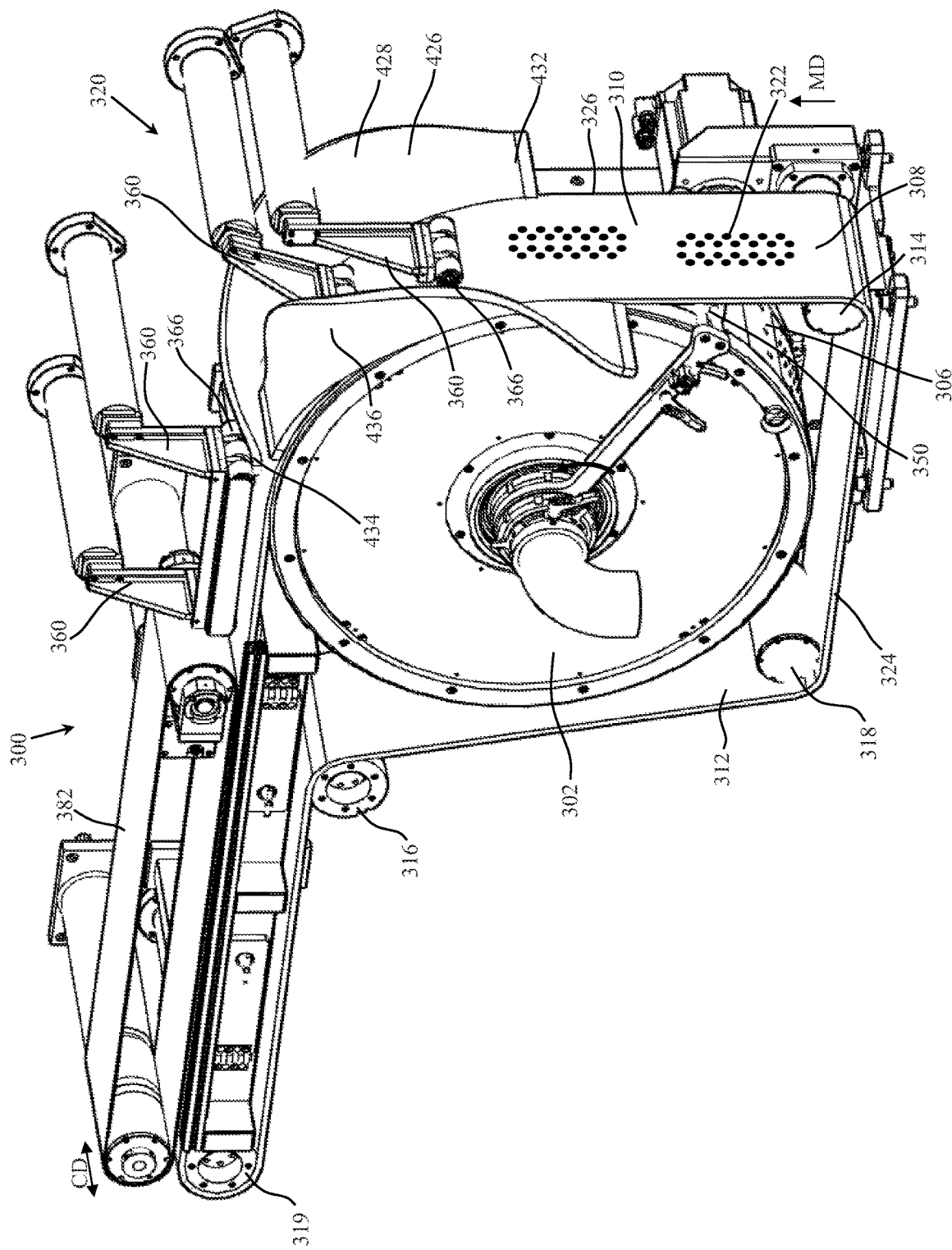
FIG. 20 is a schematic, perspective view of a folding apparatus in accordance with one non-limiting embodiment of the present disclosure.

In some embodiments, the folding assembly 320 may include a first arced plow 426 and a second arced plow 436, as illustrated in FIG. 20. The structure and function of the second arced plow 436 may be similar to the first arced plow as discussed with respect to FIGS. 19A-19E. The first arced plow 426 and the second arced plow 436 allow the absorbent article to be folded as the absorbent article traverses about the central longitudinal drum axis 304 and is disposed on the outer circumferential drum surface 306 and/or the carrier member 308. The first arced plow 426 may be offset from the second arced plow 436 in the machine direction MD, as illustrated in FIG. 20. The offset allows for the folding of the second end region of the belt not to interfere with the folding of the first end region of the belt, and vice versa. Further, in embodiments where the first end region overlaps the second end region of the belt, each region may be folded in an order with the offset configuration of the arced plows. A portion of first arced plow 426 may overlap with a portion of the second arced plow 436 in at least one of the machine direction MD and the cross direction CD. The second arced plow 436 may be configured to engage and guide or push the second end region 106b, 108b of the belt 106, 108 toward the chassis 102 and/or the central region 106c, 108c of the belt 106, 108. The first arced plow 426 may be configured to engage and guide or push the first end region 106a, 108a of the belt 106, 108 toward the chassis 102 and/or the central region 106c, 108c of the belt 106, 108. Each end region of the belt may be disposed on the chassis and/or the central region of the belt or the end regions may overlap at least a portion of one another, as illustrated in FIGS. 12D and 12C.

Figure 21:
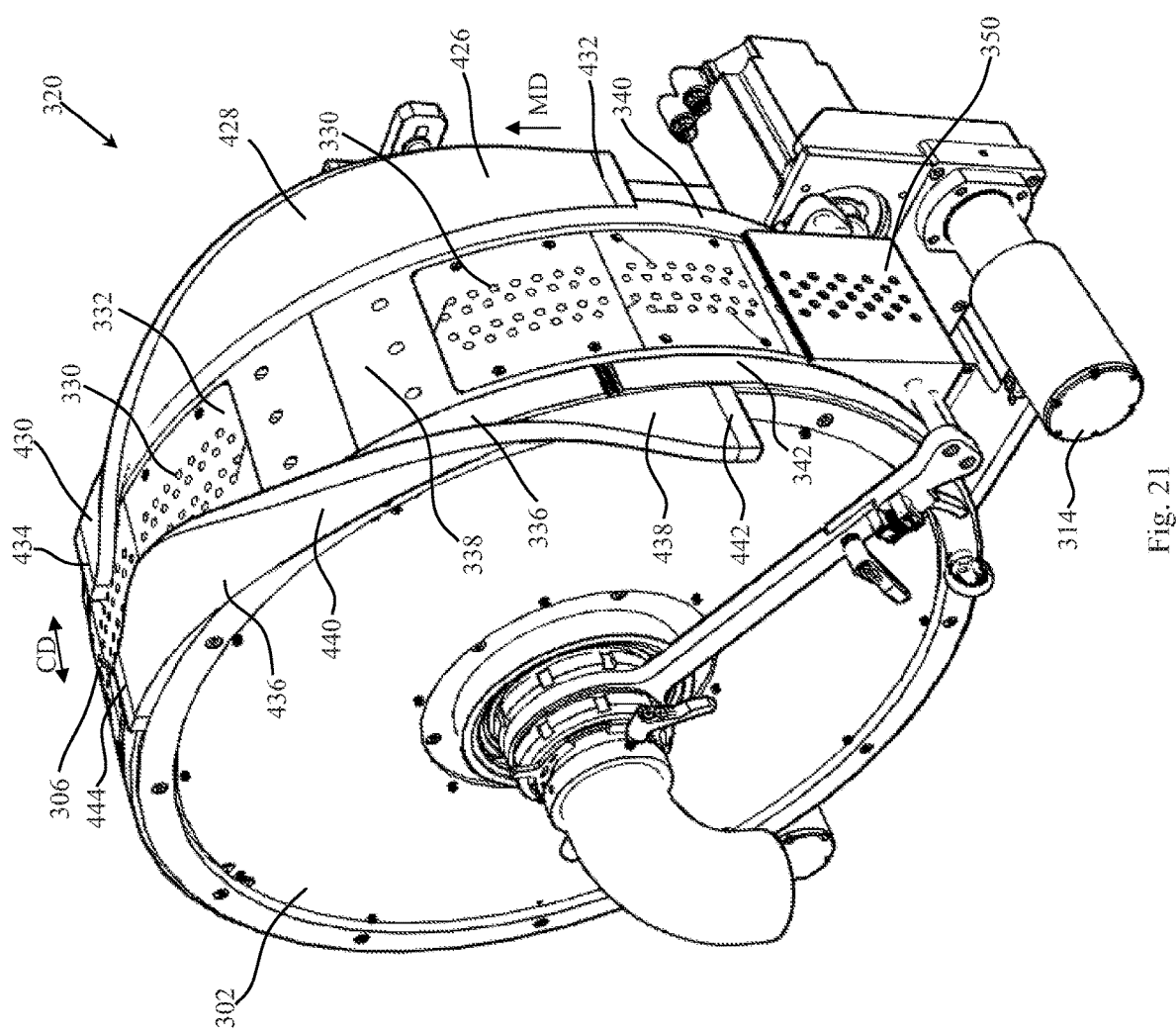
FIG. 21 is a schematic, perspective view of a first arced plow and a second arced plow positioned adjacent an outer circumferential drum surface in accordance with one non-limiting embodiment of the present disclosure.

In yet some other embodiments, the first arced plow 426 may be opposite the second arced plow 436 in the cross direction, as illustrated in FIG. 21. More specifically, the second arced plow 436 may include an inner surface 438 and an outer surface 440. The inner surface 438 of the second arced plow 436 may be in facing relationship with the inner surface 428 of the first arced plow 426. Further, the second arced plow 436 may include a first end portion 442 and a second end portion 444 opposite the first end portion 442 in the machine direction MD. The first end portion 442 of the second arced plow 436 may be opposite the first end portion 432 of the first arced plow 426 in the cross direction CD. Similarly, the second end portion 444 of the second arced plow 436 may be opposite the second end portion 434 of the first arced plow 426 in the cross direction CD. Thus, each of the first end region 106a, 108a, and the second end region 106b, 108b of the belt 106, 108 may be folded simultaneously or at substantially the same time, as the partially folded pant 101 advances in the machine direction MD.

Figure 22A:
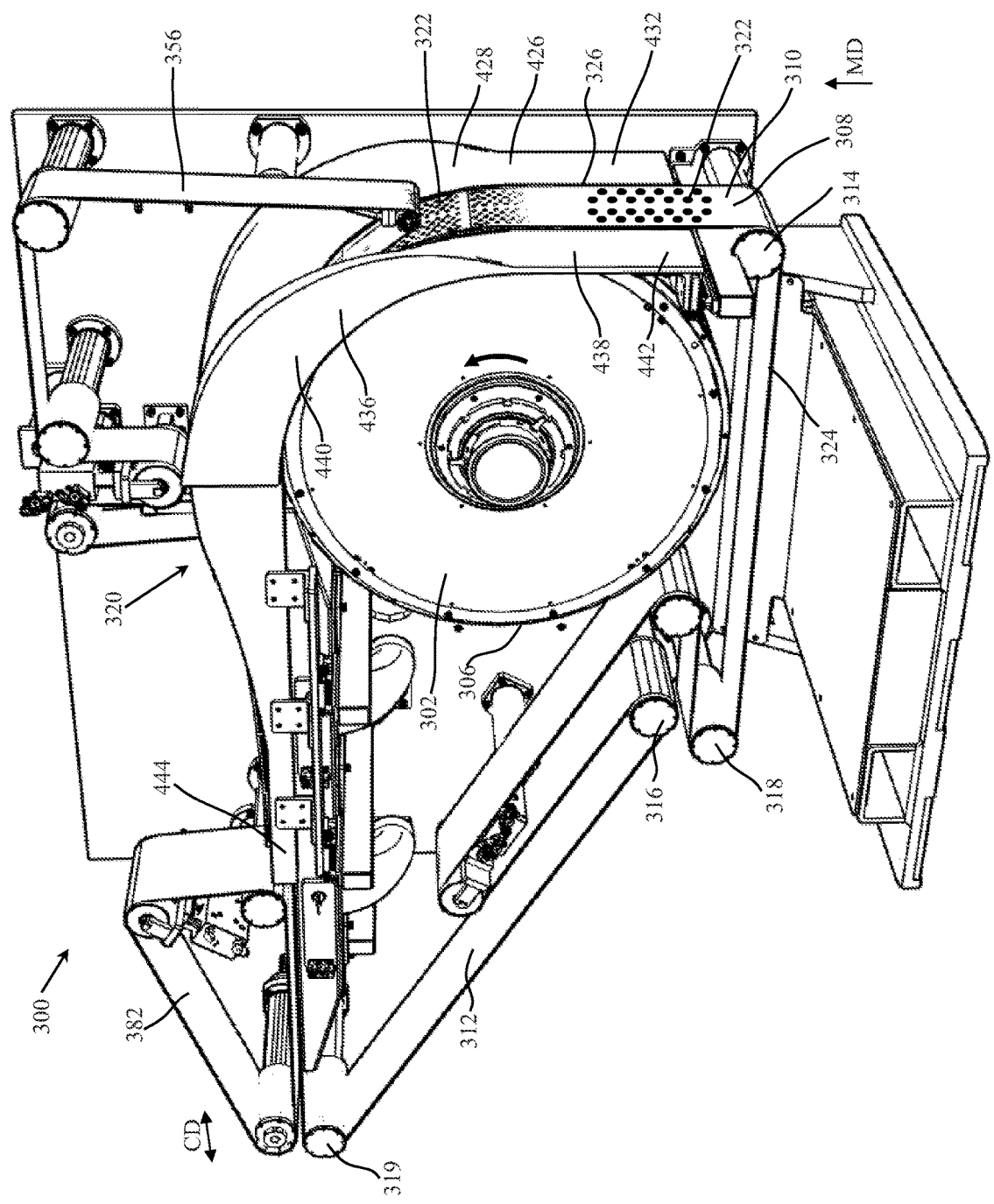
FIG. 22A is a schematic, perspective view of a folding apparatus in accordance with one non-limiting embodiment of the present disclosure.

In some embodiments, the folding assembly 320 may include a first arced plow 426 and a second arced plow 436, as illustrated in FIG. 22A. The structure and function of the second arced plow 436 may be similar to the first arced plow as discussed with respect to FIGS. 19A-19E. The first arced plow 426 and the second arced plow 436 allow the absorbent article to be folded as the absorbent article traverses about the central longitudinal drum axis 304 and is disposed on the outer circumferential drum surface 306 and/or the carrier member 308. Each of the first arced plow 426 and the second arced plow 436 may extend from about the position where the absorbent article is transferred to the folding apparatus 300 to a position downstream of the drum 306. More specifically, a portion of each of the first arced plow 426 and the second arced plow 436 may extend about a portion of the outer circumferential drum surface 306. The first arced plow 426 and the second arced plow 436 may be positioned adjacent the first edge portion and the second edge portion of the outer circumferential drum surface 306. The first arced plow 426 and the second arced plow 436 may be separated in the cross direction CD such that each plow does not interfere with the traversal of the drum 302 or the carrier member 308 and the absorbent article.

Figure 22B:
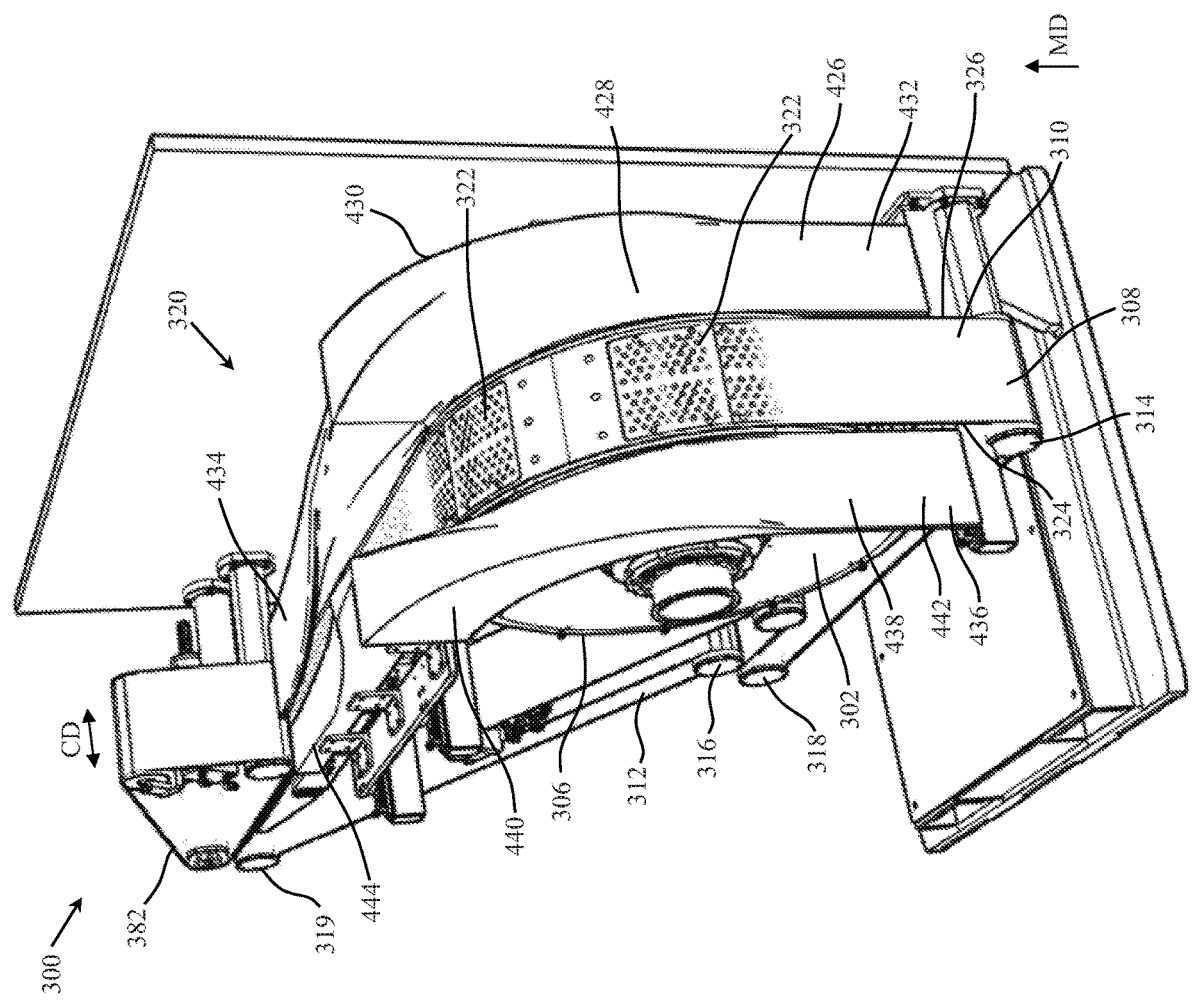
FIG. 22B is a schematic, perspective view of a folding device in accordance with one non-limiting embodiment of the present disclosure.

Referring to FIGS. 22A and 22B, the first arced plow 426 may include an inner arced plow surface 428 and an outer arced plow surface 430. Similarly, the second arced plow 436 may include an inner arced plow surface 438 and an outer arced plow surface 440. Each inner arced plow surface 428, 438 may be configured to engage and guide or push the end region of the belt onto the chassis and/or central region of the belt. Each inner arced plow surface 428, 438 may be shaped in a manner such that the end region of the belt may be accepted onto a portion of the inner arced plow surface and guided onto a portion of the central body portion 196. More specifically, the first arced plow 426 may include a first end portion 432 and a second end portion 434 opposite the first end portion 432 in the machine direction MD, and the second arced plow 436 may include a first end portion 442 and a second end portion 444 opposite the first end portion 442 in the machine direction MD. Thus, the partially folded pant 101 while advancing in the machine direction MD first traverses by the first end portion 432, 442 of each arced plow and subsequently encounters the second end portion 434, 444 of each arced plow. As described with respect to FIG. 19D, the inner surface of the first end portion of each arced plow may form a first arced angle δ with the outer circumferential drum surface 306 or the first surface 310 of the carrier member 308. The first arced angle δ may be large enough to accept the partially folded pant 101 and/or to avoid adversely interfering with the transfer apparatus 220 and, more specifically, the transfer members 230, as illustrated in FIG. 9. Further, the first end portion may be positioned to prevent the partially folded pant 101 from interfering with the traversing drum 302 or other equipment positioned adjacent the region where the absorbent article is transferred and traverses about the drum 302. The first arced angle δ may be an obtuse angle. The first arced angle δ may be from about 45 degrees to about 270 degrees and/or from about 160 degrees to about 220 degrees, including all 0.1 increments therebetween.

Each arced plow curves from the first end portion to the second end portion. The first end portion curves toward the second end portion such that as the partially folded pant advances from the first end portion to the second end portion, the end regions are guided onto the chassis and/or central region of the belt. For example, the arced plows may be helically shaped. The inner surface of the second end portion may form a second arced angle α with the outer circumferential drum surface 306 or the first surface 310 of the carrier member 308, similar to that illustrated in FIG. 19E. The second arced angle α may be an acute angle. The second arced angle α may be from about −45 degrees to about 60 degrees and/or from about −10 degrees to about 20 degrees, including all 0.1 increments therebetween. Further, there may be a gap between the inner surface and the carrier member 308 and/or the outer circumferential drum surface 306 to provide clearance for the absorbent article traversing in the machine direction MD. The curve of the arced plows cause the end regions of the belt to be guided toward or pushed toward the chassis and/or the central region of the belt. The arced plow may be any length such that arced plow engages the end region while the end region of the belt extends in a direction away from the drum 302 and guides the end region into a fold. Further, the arced plow may be any height such that the arced plow controls the end region of the belt while guiding the end region toward the chassis.

In some embodiments, the second end portion 444 of the second arced plow 436 and the second end portion 434 of the first arced plow 426 may be offset horizontally and/or vertically to allow sufficient clearance for each end region to be folded without interfering with the other end region. Further, during folding of the partially folded pant, the outer arced plow surface 430 of the first arced plow 426 may support the end region of the belt prior to being disposed on the central region and/or the chassis of the partially folded pant. Similarly, the outer arced plow surface 440 of the second arced plow 436 may support the end region of the belt prior to being disposed on the central region and/or the chassis of the partially folded pant.

It is also to be appreciated that the end regions of the partially folded pant may extend in a direction away from the drum 302 as the drum traverses about the central longitudinal drum axis 304. The end regions of the partially folded pant may engage only a portion of each of the inner plow surfaces. Thus, the end regions of the partially folded pant may not engage the inner plow surfaces as the partially folded pant traverses about the central longitudinal drum axis 304. More specifically, the inner arced plow surface may be at such an angle with the outer circumferential drum surface and/or the carrier member that the extended end regions fail to engage the inner arced plow surface.

Upon exiting the second end portion of each of the arced plows, the first end region 106a, 108a and/or the second end region 106b, 108b of the belt 106, 108 may be disposed on the chassis 102 and/or the central region 106c, 108c, of the belt 106, 108. The folded pant 380 may advance to a third carrier member 382 and/or additional processes.

The second end portion 434 of the first arced plow 426 may be offset from the second end portion 444 of the second arced plow 436 in the machine direction MD. Thus, the first arced plow 426 may be a different length than the second arced plow 436. The offset may allow for the folding of the second end region of the belt not to interfere with the folding of the first end region of the belt, and vice versa. Further, in embodiments where the first end region overlaps the second end region of the belt, each region may be folded in an order without interference. In some embodiments, a portion of first arced plow 426 may overlap with a portion of the second arced plow 436 in at least one of the machine direction MD and the cross direction CD. The second arced plow 436 may be configured to engage and guide or push the second end region 106b, 108b of the belt 106, 108 toward the chassis 102 and/or the central region 106c, 108c of the belt 106, 108. The first arced plow 426 may be configured to engage and guide or push the first end region 106a, 108a of the belt 106, 108 toward the chassis 102 and/or the central region 106c, 108c of the belt 106, 108. Each end region of the belt may be disposed on the chassis and/or the central region of the belt or the end regions may overlap at least a portion of one another, as illustrated in FIGS. 12D and 12C.

The first arced plow 426 and the second arced plow 436 may each be a single unit, which is placed about a portion of the drum 302 and extending beyond the drum 302 in the machine direction MD. The first arced plow 426 and the second arced plow 436 may include segments such that portions of each arced plow may be removed and replaced or removed without replacement. By segmenting the plow, the length of the arced plows may be adjusted or segments of the arced plow may be substituted for segments intended to produce, for example, different sized consumer products.

It is to be appreciated that each of the arced plow and planar plow may define one or more apertures. Fluid may be passed through the one or more apertures to create a vacuum force or a pressure force on the end region of the absorbent article. For example, fluid may be pulled through the one or more apertures in a direction from the inner surface towards the outer surface of the plow to create a vacuum force on the end region of the absorbent article. A fluid may be pushed through the one or more apertures in a direction from the outer surface towards the inner surface of the plow to create a pressure force on the end region of the absorbent article.

Figure 23A:
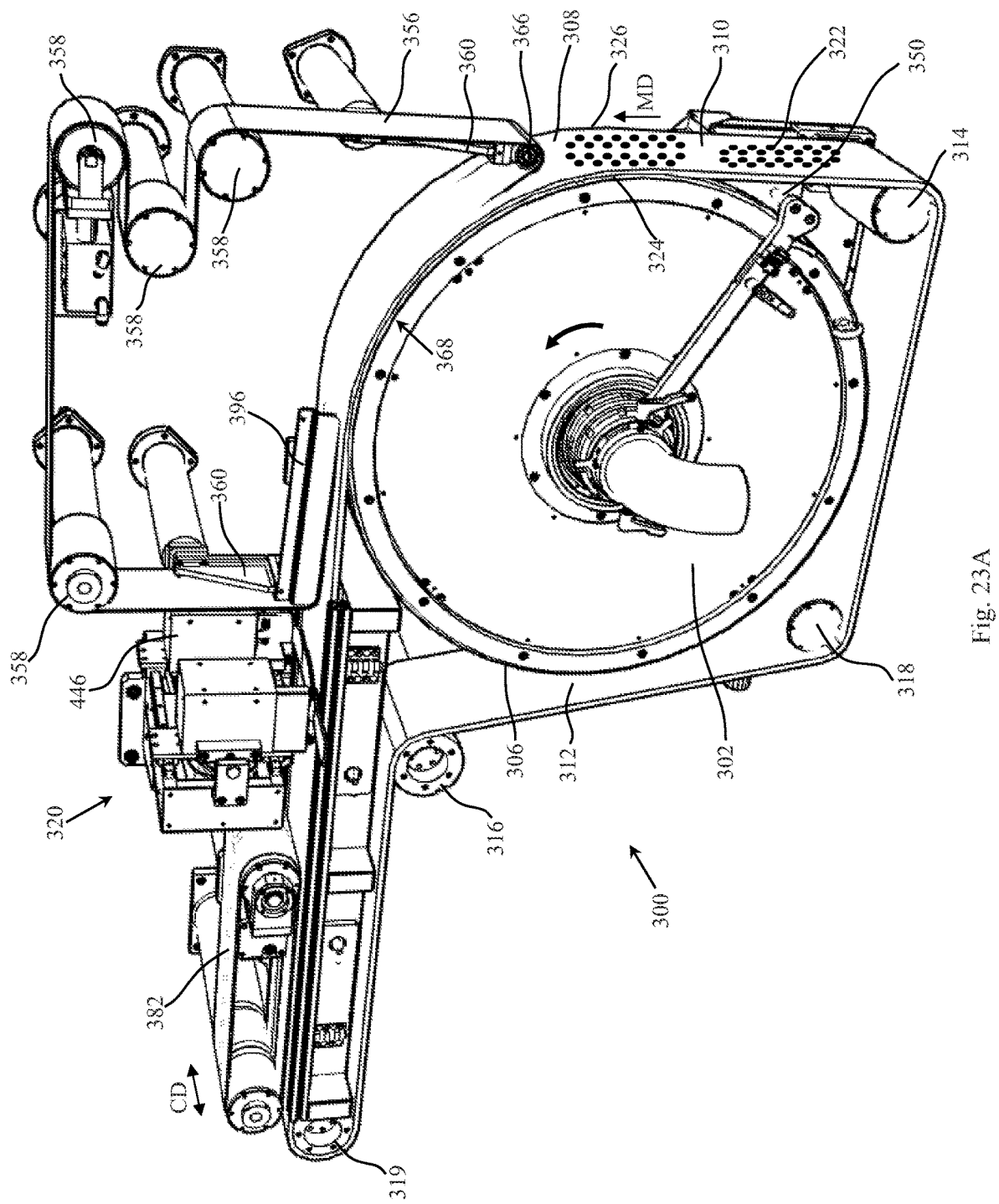
FIG. 23A is a schematic, perspective view of a folding apparatus in accordance with one non-limiting embodiment of the present disclosure.
Figure 23B:
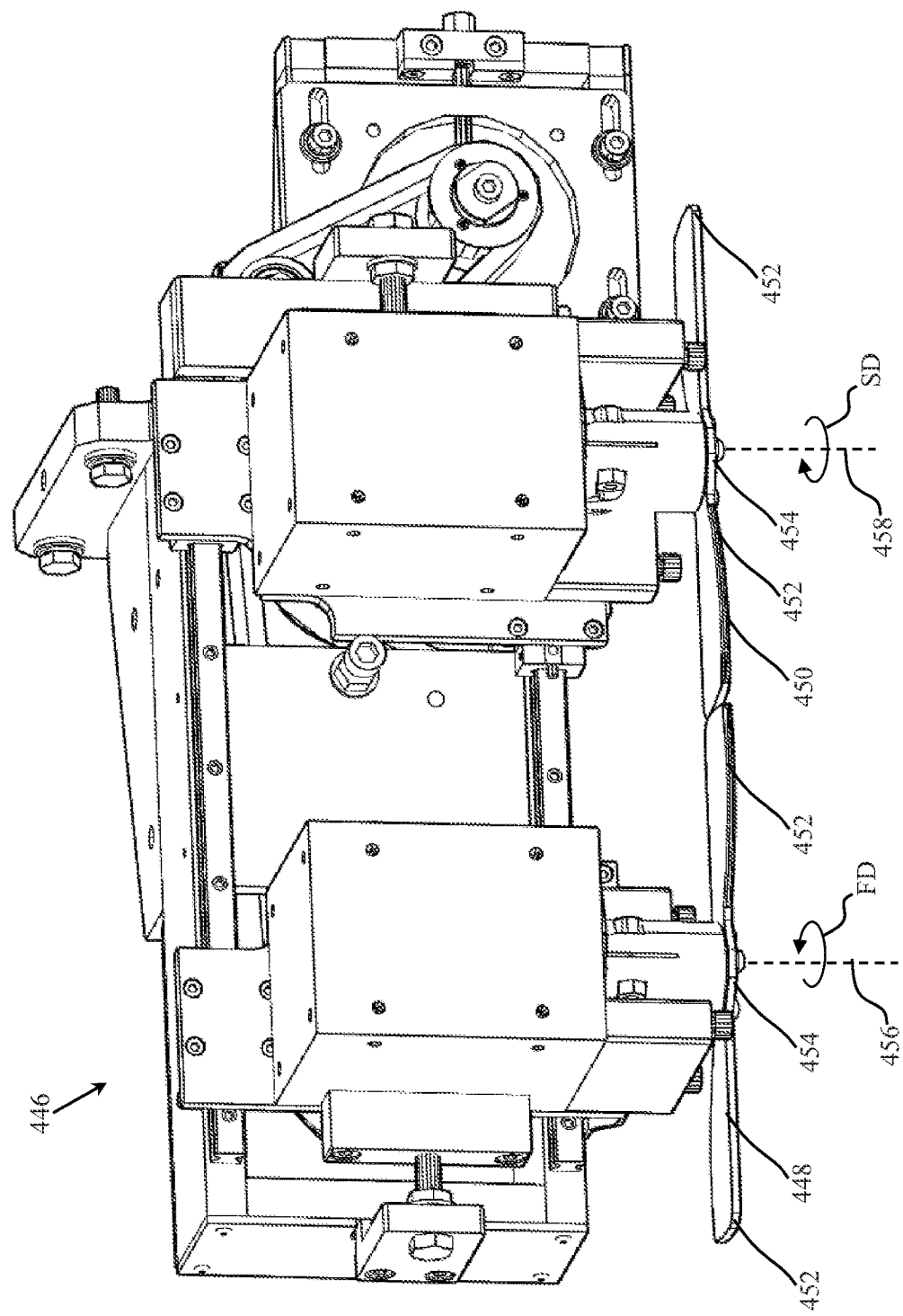
FIG. 23B is a schematic, perspective view of a folding device in accordance with one non-limiting embodiment of the present disclosure.

Referring to FIGS. 23A and 23B, the folding assembly 320 may include a folding device 446. The folding device 446 may be positioned adjacent the outer circumferential drum surface 306 such that the partially folded pant 101 may be folded as the partially folded pant traverses on the drum 302 or the folding device 446 may be positioned downstream of the drum 302 such that the partially folded pant 101 may be removed from the drum 302 before being folded by the folding device 446, as illustrated in FIG. 23A. The folding device 446 may include a first tucking member 448 and a second tucking member 450. Each of the first tucking member 448 and the second tucking member 450 may include one or more blades 452 disposed about a central plate 454, which may be a substantially rigid, planar member. The first tucking member 448 may be configured to rotate about a first central longitudinal axis 456 in a first direction FD. Similarly, the second tucking member 450 may be configured to rotation about a second central longitudinal axis 458 in a second direction SD. Each blade 452 may rotate at a constant velocity or a variable velocity about their respective central longitudinal axis. Each of the blades 452 may be configured to engage the end region of the belt as the blade 452 rotates about the axis of rotation. More specifically, as previously discussed, the first and second end regions of the partially folded pant 101 extend in a direction away from the carrier member 308 and/or the outer circumferential drum surface 306 as the partially folded pant 101 traverses on the drum 302 due the centrifugal and/or gravitational forces generated as the drum 302 rotates. The first and second end regions of the belt may continue to be in this extended orientation as the partially folded pant 101 is advanced to the folding assembly 320. Upon reaching the folding assembly 320, which, in some embodiments, is a folding device 446, the blade 452 of the first tucking member 448 may engage the outer surface of the second end region 106b, 108b of the belt 106, 108 causing the second end region to be pushed or guided toward the chassis 102 and/or the central region of the belt. In embodiments where the first tucking member 448 includes more than one blade, the additional blades may continue to rotate about the first central longitudinal axis 456 and engage the outer surface of the end region to push or guide the end region toward the chassis and/or central region of the belt. Similarly, the blade 452 of the second tucking member 450 may engage the outer surface of the first end region 106a, 108a of the belt 106, 108 causing the first end region to be pushed or guided toward the chassis 102, and/or the central region of the belt. In embodiments where the second tucking member 450 includes more than one blade, the additional blades may continue to rotate about the second central longitudinal axis 458 and engage the outer surface of the end region to push or guide the end region toward the chassis and/or central region of the belt. Upon exiting the folding device 446 the first end region may be disposed on at least a portion of the chassis 102 and/or the central region of the belt and the second end region may be disposed on at least a portion of the chassis 102 and/or the central region of the belt forming a folded pant 308. The folded pant 308 may be advanced to a third carrier member 382 and/or one or more additional processes. The first tucking member 448 may be offset from the second tucking member 450 in the machine direction MD. The first tucking member 448 may also be offset from the second tucking member 450 in the cross direction CD.

It is to be appreciated that the first and second end regions 106a, 108a and 106b, 108b of the first and second elastic belts 106, 108 may be folded using various techniques. Various methods and apparatuses for folding end regions of an absorbent article are disclosed in: U.S. Patent Publication No. 2011/0247747 A1, published on Oct. 13, 2011, U.S. Patent Publication No. 2011/0251038 A1, published Oct. 13, 2011; and U.S. Pat. Nos. 6,523,035 and 6,776,316. These methods and apparatuses may be combined with the aforementioned to form a folded absorbent article.

Figure 24A:
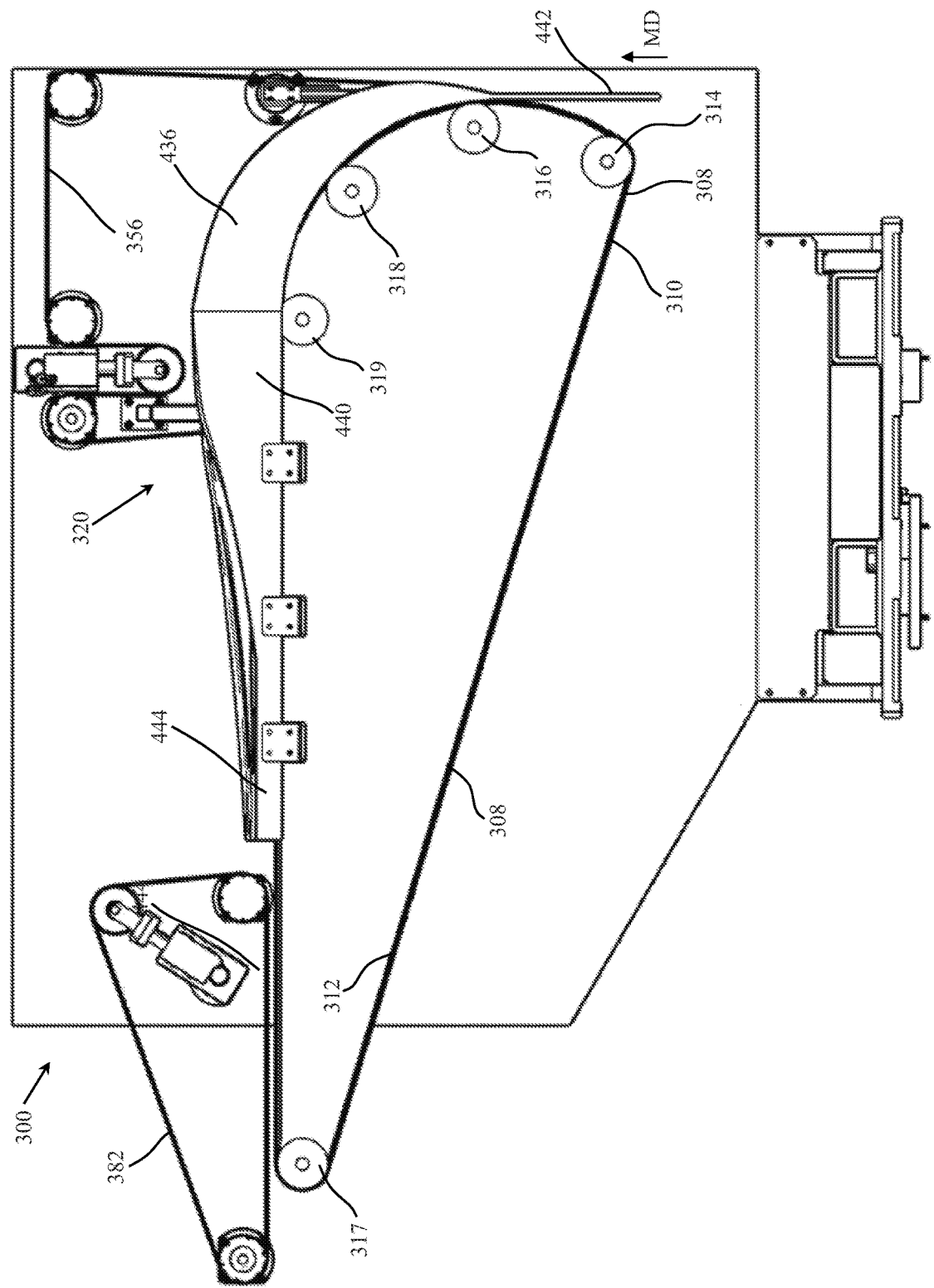
FIG. 24A is a schematic, side view of a folding apparatus in accordance with one non-limiting embodiment of the present disclosure.

It is to be appreciated that the folding apparatus 300 may be configured in various different ways. For example, a carrier member, and/or a series of rollers may replace the drum 302 as illustrated in FIGS. 24A and 24B. The carrier member 308 may traverse about one or more guide rollers, such as a first guide roller 314, a second guide roller 316, a third guide roller 318, a fourth guide roller 319, and a fifth guide roller 317. There may be any number of guide roller such that the carrier member 308 is in proper placement to receive and transfer the partially folded pant. More specifically, a portion of the guide rollers may be positioned such that as the carrier member traverses over the guide rollers an arcuate path is formed. This arcuate path allows the partially folded pant to be subject to centrifugal forces and/or gravitational forces causing the end regions of the belt to extend away from the surface of the carrier member as the partially folded pant traverses in the machine direction MD. Each of the guide rollers may be adjustable. For example the guide rollers may be adjusted horizontally and/or vertically to change the shape and/or path of the carrier member 308. As previously discussed, the carrier member 308 may define one or more apertures 322. The one or more apertures 322 may be in fluid communication with a fluid chamber which applies a vacuum force on the partially folded pant. The folding assembly 320 may be configured such as previously discussed.

This application claims the benefit of U.S. Provisional Application No. 62/310,007 filed on Mar. 18, 2016, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An apparatus for folding an absorbent article comprising:
- a drum comprising a fluid chamber and an outer circumferential drum surface surrounding a central longitudinal drum axis, wherein the drum is configured to rotate about the central longitudinal drum axis;
- a carrier member disposed on a portion of the outer circumferential drum surface, the carrier member having a first carrier edge and a second carrier edge opposite the first carrier edge, wherein the carrier member defines a plurality of apertures, wherein the plurality of apertures are disposed over the fluid chamber of the drum creating a vacuum pressure through the plurality of aperatures, and wherein a central body portion of an absorbent article is positioned over the plurality of aperatures and a first end region of a belt extends beyond the plurality of aperatures toward the first carrier edge and a second end region of the belt extends beyond the plurality of aperatures toward the second carrier edge, wherein as the absorbent article advances on the carrier member about the central longitudinal drum axis, the central body portion is held in postion over the plurality of aperatures by the vacuum pressure and the first end region of the belt and the second end region of the belt are deflected in a first direction away from and at an angle α to the central longitudinal drum axis, wherein the angle α is from 30 degrees to 135 degrees;
- a first plow positioned adjacent a first side of the drum, the first plow having a first side plow edge and a second side plow edge opposite the first side plow edge, wherein the first side plow edge is adjacent the first carrier edge and the second side plow edge is positioned over a portion of the carrier member;
- a second plow positioned adjacent a second side of the drum, the second plow having a third side plow edge and a fourth side plow edge opposite the third side plow edge, and wherein the third side plow edge is adjacent the second carrier edge and the fourth side plow edge is positioned over a portion of the carrier member;
- wherein the first plow is configured to engage the first end region of the belt of the absorbent article while the first end region of the belt is deflected in the first direction away from the central longitudinal drum axis,
- wherein the second plow is configured to engage the second end region of the belt of the absorbent article while the second end region of the belt is deflected in the first direction away from the central longitudinal drum axis,
- wherein the first end region of the belt is folded onto a central region of the absorbent article and the second end region of the belt is folded onto a central region of the absorbent article to form a folded absorbent article; and
- a second carrier member positioned in facing relationship with the carrier member, wherein the second carrier member configured to engage and transfer the folded absorbent article.

2. The apparatus of claim 1, wherein the first plow is positioned opposite the second plow in a cross direction.

3. The apparatus of claim 1, wherein the first plow is offset from the second plow in a machine direction.

4. The apparatus of claim 1, wherein the second plow extends about a portion of the outer circumferential drum surface.

5. The apparatus of claim 1, wherein the second plow extends from a first plow edge to a second plow edge such that the second plow has an arced shape causing the second end region of the belt to be pushed toward the central portion of the absorbent article.

6. The apparatus of claim 1, wherein the fluid chamber comprises a first fluid region and a second fluid region positioned adjacent the first fluid region, wherein each of the first fluid region and the second fluid region is controlled independently.

* * * * *